(12) United States Patent
Danter et al.

(10) Patent No.: US 8,420,643 B2
(45) Date of Patent: Apr. 16, 2013

(54) COMPOUNDS AND METHOD FOR TREATMENT OF CANCER

(75) Inventors: Wayne R. Danter, London (CA); Martyn Brown, Scarborough (CA); Franck LePifre, Olivet (FR)

(73) Assignee: Critical Outcome Technologies Inc., London-Ontario (CA)

( * ) Notice: Subject to any disclaimer, the term of this patent is extended or adjusted under 35 U.S.C. 154(b) by 0 days.

(21) Appl. No.: 13/310,506

(22) Filed: Dec. 2, 2011

(65) Prior Publication Data

US 2012/0077820 A1   Mar. 29, 2012

Related U.S. Application Data

(60) Continuation of application No. 13/190,230, filed on Jul. 25, 2011, which is a division of application No. 12/013,079, filed on Jan. 11, 2008, now Pat. No. 8,034,815.

(60) Provisional application No. 60/884,489, filed on Jan. 11, 2007, provisional application No. 60/884,504, filed on Jan. 11, 2007.

(51) Int. Cl.
*A61K 31/535*     (2006.01)
*A61K 31/497*     (2006.01)
*C07D 403/12*     (2006.01)
*C07D 417/12*     (2006.01)
*C07D 401/12*     (2006.01)

(52) U.S. Cl.
USPC ............. 514/236.8; 514/253.01; 514/253.03; 544/133; 544/361; 544/364

(58) Field of Classification Search ............... 514/236.8, 514/253.01, 253.03; 544/364, 133, 361
See application file for complete search history.

(56) References Cited

U.S. PATENT DOCUMENTS

| | | |
|---|---|---|
| 3,239,539 A | 3/1966 | Bartlett et al. |
| 3,250,791 A | 5/1966 | Webster et al. |
| 3,671,639 A | 6/1972 | Sasse et al. |
| 4,463,077 A | 7/1984 | Matsuura et al. |
| 4,537,844 A | 8/1985 | Hashimoto |
| 4,593,027 A | 6/1986 | Winklemann et al. |
| 4,619,878 A | 10/1986 | Hashimoto |
| 4,748,160 A | 5/1988 | Bennion et al. |
| 4,927,843 A | 5/1990 | Teitz |
| 4,977,051 A | 12/1990 | Ohno et al. |
| 4,978,670 A | 12/1990 | Rector et al. |
| 4,985,433 A | 1/1991 | Secrist, III et al. |
| 4,985,434 A | 1/1991 | Secrist, III et al. |
| 5,008,265 A | 4/1991 | Secrist, III et al. |
| 5,008,270 A | 4/1991 | Secrist, III et al. |
| 5,023,334 A | 6/1991 | Rector et al. |
| 5,135,928 A | 8/1992 | Reiter et al. |
| 5,155,110 A | 10/1992 | Connor et al. |
| 5,189,039 A | 2/1993 | Niwas et al. |
| 5,196,291 A | 3/1993 | Okada et al. |
| 5,292,756 A | 3/1994 | Duggan et al. |
| 5,328,914 A | 7/1994 | Hocquaux et al. |
| 5,334,748 A | 8/1994 | Buckley et al. |
| 5,344,836 A | 9/1994 | Hamanaka et al. |
| 5,358,946 A | 10/1994 | Wilde |
| 5,409,930 A | 4/1995 | Spada et al. |
| 5,441,847 A | 8/1995 | Fukawa et al. |
| 5,480,883 A | 1/1996 | Spada et al. |
| 5,521,184 A | 5/1996 | Zimmermann |
| 5,543,520 A | 8/1996 | Zimmermann |
| 5,604,210 A | 2/1997 | Nagaoka et al. |
| 5,612,340 A | 3/1997 | Zimmermann |
| 5,618,829 A | 4/1997 | Takayanagi et al. |
| 5,646,153 A | 7/1997 | Spada et al. |
| 5,656,643 A | 8/1997 | Spada et al. |
| 5,710,158 A | 1/1998 | Myers et al. |
| 5,714,493 A | 2/1998 | Myers et al. |
| 5,721,238 A | 2/1998 | Heiker et al. |

(Continued)

FOREIGN PATENT DOCUMENTS

| | | |
|---|---|---|
| CA | 2109975 | 5/1994 |
| CA | 2553242 | 8/2005 |
| CA | 2584179 | 4/2006 |
| CN | 1224005 | 7/1999 |
| CN | 1891701 | 1/2007 |
| CN | 1907970 | 2/2007 |
| DE | 3237649 | 4/1984 |
| DE | 4207400 | 9/1993 |
| DE | 4207400 A1 | 9/1993 |
| DE | 04400451 | 7/1994 |

(Continued)

OTHER PUBLICATIONS

Supplementary European Search Report for European Application No. 08865722 mailed Feb. 9, 2012.

(Continued)

*Primary Examiner* — James O Wilson
*Assistant Examiner* — Ebenezer O Sackey
(74) *Attorney, Agent, or Firm* — Swanson & Bratschun, LLC

(57) ABSTRACT

The present invention is directed to methods of use of a compound of Formula I:

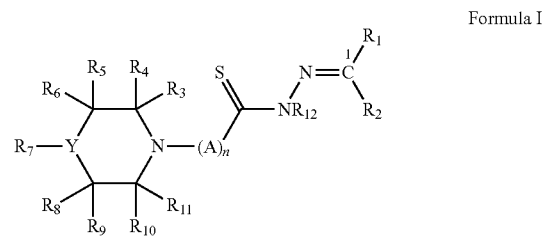

Formula I and/or a pharmaceutically-acceptable salt, hydrate, solvate, tautomer, optical isomer, or combination thereof, a composition comprising the thiosemicarbazone, a method of administration thereof, and use thereof to treat a cancer.

44 Claims, 8 Drawing Sheets

U.S. PATENT DOCUMENTS

| | | | |
|---|---|---|---|
| 5,736,534 | A | 4/1998 | Arnold |
| 5,750,088 | A | 5/1998 | Sworin et al. |
| 5,760,041 | A | 6/1998 | Wissner et al. |
| 5,763,470 | A | 6/1998 | Tang et al. |
| 5,795,889 | A | 8/1998 | Spada et al. |
| 5,798,451 | A | 8/1998 | Von Deyn et al. |
| 5,872,272 | A | 2/1999 | Yano et al. |
| RE36,256 | E | 7/1999 | Spada |
| 5,932,574 | A | 8/1999 | Baker |
| 5,948,819 | A | 9/1999 | Ohtsuka et al. |
| 5,958,935 | A | 9/1999 | Davis et al. |
| 5,977,146 | A | 11/1999 | Muller et al. |
| 6,057,320 | A | 5/2000 | Spada et al. |
| 6,069,134 | A | 5/2000 | Roth et al. |
| 6,103,728 | A | 8/2000 | Tang et al. |
| 6,127,374 | A | 10/2000 | Bridges |
| 6,153,617 | A | 11/2000 | Bridges |
| 6,156,617 | A | 12/2000 | Saitoh |
| 6,169,091 | B1 | 1/2001 | Cockerill et al. |
| 6,174,889 | B1 | 1/2001 | Cockerill et al. |
| 6,180,636 | B1 | 1/2001 | Traxler et al. |
| 6,184,377 | B1 | 2/2001 | Gao |
| 6,207,669 | B1 | 3/2001 | Cockerill et al. |
| 6,235,746 | B1 | 5/2001 | Davis et al. |
| 6,251,911 | B1 | 6/2001 | Bold et al. |
| 6,268,391 | B1 | 7/2001 | Dickerson et al. |
| 6,352,168 | B1 | 3/2002 | Lin |
| RE37,650 | E | 4/2002 | Myers et al. |
| 6,391,874 | B1 | 5/2002 | Cockerill et al. |
| 6,420,560 | B1 | 7/2002 | Numerof et al. |
| 6,432,963 | B1 | 8/2002 | Hisamichi et al. |
| 6,525,072 | B1 | 2/2003 | Tang et al. |
| 6,528,509 | B1 | 3/2003 | Hale et al. |
| 6,538,002 | B1 | 3/2003 | Finke et al. |
| 6,562,818 | B1 | 5/2003 | Bridges |
| 6,600,037 | B1 | 7/2003 | Davis et al. |
| 6,635,641 | B2 | 10/2003 | Bender et al. |
| 6,723,726 | B1 | 4/2004 | Cockerill et al. |
| 6,828,320 | B2 | 12/2004 | Cockerill et al. |
| 6,949,639 | B1 | 9/2005 | Hovinen et al. |
| 7,052,870 | B2 | 5/2006 | Sabatini et al. |
| 7,138,416 | B2 | 11/2006 | Sankaranarayanan |
| 7,175,844 | B2 | 2/2007 | King |
| 7,202,367 | B2 | 4/2007 | Cellier et al. |
| 2001/0021717 | A1 | 9/2001 | Potter et al. |
| 2001/0027205 | A1 | 10/2001 | Camden |
| 2001/0041964 | A1 | 11/2001 | Grass et al. |
| 2001/0044451 | A1 | 11/2001 | Fraley et al. |
| 2001/0047007 | A1 | 11/2001 | Fraley et al. |
| 2001/0047364 | A1 | 11/2001 | Proctor |
| 2001/0049092 | A1 | 12/2001 | Ekins et al. |
| 2001/0051628 | A1 | 12/2001 | Huang et al. |
| 2002/0010550 | A1 | 1/2002 | Grass et al. |
| 2002/0012641 | A1 | 1/2002 | Voorhees et al. |
| 2002/0013334 | A1 | 1/2002 | Robl et al. |
| 2002/0013662 | A1 | 1/2002 | Grass et al. |
| 2002/0014408 | A1 | 2/2002 | Schroeder |
| 2002/0018988 | A1 | 2/2002 | Klinck et al. |
| 2002/0028779 | A1 | 3/2002 | High et al. |
| 2002/0028826 | A1 | 3/2002 | Robl et al. |
| 2002/0042423 | A1 | 4/2002 | Richert et al. |
| 2002/0061901 | A1 | 5/2002 | Robl et al. |
| 2002/0072526 | A1 | 6/2002 | Fraley et al. |
| 2002/0086791 | A1 | 7/2002 | Iglesia et al. |
| 2002/0115858 | A1 | 8/2002 | Zimmermann et al. |
| 2002/0147214 | A1 | 10/2002 | Cockerill et al. |
| 2002/0151540 | A1 | 10/2002 | Lai et al. |
| 2003/0087881 | A1 | 5/2003 | Bridges |
| 2003/0125343 | A1 | 7/2003 | Gambacorti-Passerini et al. |
| 2003/0130286 | A1 | 7/2003 | Denny et al. |
| 2003/0153755 | A1 | 8/2003 | Moffat et al. |
| 2003/0176396 | A1 | 9/2003 | Shea et al. |
| 2003/0181495 | A1 | 9/2003 | Lai et al. |
| 2003/0212269 | A1 | 11/2003 | Davis et al. |
| 2003/0236413 | A1 | 12/2003 | Cellier et al. |
| 2004/0092747 | A1 | 5/2004 | Bender et al. |
| 2004/0102453 | A1 | 5/2004 | Buerger et al. |
| 2004/0171032 | A1 | 9/2004 | Baker et al. |
| 2004/0204477 | A1 | 10/2004 | Moll et al. |
| 2004/0224968 | A1 | 11/2004 | Seidelmann et al. |
| 2004/0235786 | A1 | 11/2004 | Orr |
| 2004/0235798 | A1 | 11/2004 | Murthi et al. |
| 2005/0010017 | A1 | 1/2005 | Blakely et al. |
| 2005/0014169 | A1 | 1/2005 | Latham et al. |
| 2005/0131022 | A1 | 6/2005 | Player et al. |
| 2005/0192884 | A1 | 9/2005 | Raines |
| 2006/0019831 | A1 | 1/2006 | Reinhard et al. |
| 2006/0217426 | A1 | 9/2006 | Eto et al. |
| 2007/0197495 | A1 | 8/2007 | Chibale |
| 2007/0280928 | A1 | 12/2007 | Buck et al. |
| 2008/0004274 | A1 | 1/2008 | Diaz et al. |
| 2008/0171744 | A1* | 7/2008 | Danter et al. ............... 514/236.8 |
| 2011/0281887 | A1 | 11/2011 | Danter et al. |

FOREIGN PATENT DOCUMENTS

| | | |
|---|---|---|
| EP | 0 106 284 | 10/1983 |
| EP | 0 142 740 | 10/1984 |
| EP | 0 225 726 | 11/1986 |
| EP | 00172031 | 5/1988 |
| EP | 0 361 645 | 6/1989 |
| EP | 0329108 | 8/1989 |
| EP | 0 420 005 | 9/1990 |
| EP | 0 452 848 | 4/1991 |
| EP | 0425282 | 5/1991 |
| EP | 0 512 420 | 4/1992 |
| EP | 0 554 856 | 2/1993 |
| EP | 0 580 374 | 7/1993 |
| EP | 00571857 | 12/1993 |
| EP | 0600 832 | 6/1994 |
| EP | 0631179 | 12/1994 |
| EP | 0 722 937 | 1/1996 |
| EP | 0 727 701 | 2/1996 |
| EP | 00727701 | 8/1996 |
| EP | 0 807 580 | 5/1997 |
| EP | 0 902 028 | 8/1998 |
| EP | 00902028 | 3/1999 |
| EP | 00807850 | 10/2000 |
| EP | 01103549 | 5/2001 |
| EP | 01325921 | 7/2003 |
| FR | 2013371 | 4/1970 |
| FR | 2879194 | 6/2006 |
| GB | 1026401 | 4/1966 |
| GB | 1231783 | 5/1971 |
| GB | 2304471 | 3/1997 |
| GB | 2357971 | 7/2001 |
| JP | 56-095161 | 8/1981 |
| JP | 59088468 | 5/1984 |
| JP | 60184254 | 9/1985 |
| JP | 3093767 | 4/1991 |
| JP | 05058894 | 3/1993 |
| JP | 1993241264 | 9/1993 |
| JP | 06-247990 | 9/1994 |
| JP | 07-072571 | 3/1995 |
| JP | 1995114195 | 5/1995 |
| JP | 7219256 | 8/1995 |
| JP | 9328463 | 12/1997 |
| JP | 11080131 | 3/1999 |
| JP | 11133545 | 5/1999 |
| JP | 2000143636 | 5/2000 |
| JP | 2001172217 | 6/2001 |
| JP | 2006-181940 | 7/2006 |
| JP | 2006181940 | 7/2006 |
| WO | WO 86/04582 | 8/1986 |
| WO | WO 91/06548 | 5/1991 |
| WO | WO 92/03421 | 3/1992 |
| WO | WO 92/06076 | 4/1992 |
| WO | WO 92/08464 | 5/1992 |
| WO | WO 93/02091 | 2/1993 |
| WO | WO 93/21187 | 10/1993 |
| WO | WO 94/18959 | 9/1994 |
| WO | WO 95/23796 | 2/1995 |
| WO | WO 95/17423 | 6/1995 |
| WO | WO 95/27693 | 10/1995 |
| WO | WO 96/05818 | 2/1996 |
| WO | WO 96/09294 | 3/1996 |

| | | |
|---|---|---|
| WO | WO 96/14295 | 5/1996 |
| WO | WO 96/37472 | 11/1996 |
| WO | WO 97/00894 | 1/1997 |
| WO | WO 97/02238 | 1/1997 |
| WO | WO 97/03069 | 1/1997 |
| WO | WO 97/13760 | 4/1997 |
| WO | WO 98/08492 | 3/1998 |
| WO | WO 98/55448 | 12/1998 |
| WO | WO 99/09016 | 2/1999 |
| WO | WO 99/18102 | 4/1999 |
| WO | WO 99/62486 | 12/1999 |
| WO | WO 00/09126 | 2/2000 |
| WO | WO 00/18737 | 4/2000 |
| WO | WO 00/18740 | 4/2000 |
| WO | WO 00/50032 | 8/2000 |
| WO | WO 00/61186 | 10/2000 |
| WO | WO 00/74702 | 12/2000 |
| WO | WO 00/74742 | 12/2000 |
| WO | WO 01/12227 | 2/2001 |
| WO | WO 01/16271 | 3/2001 |
| WO | WO 01/34585 | 5/2001 |
| WO | WO 01/47899 | 7/2001 |
| WO | WO 01/53274 | 7/2001 |
| WO | WO 01/25220 | 9/2001 |
| WO | WO 01/64650 | 9/2001 |
| WO | WO 01/64825 | 9/2001 |
| WO | WO 01/64828 | 9/2001 |
| WO | WO 01/64994 | 9/2001 |
| WO | WO 01/66709 | 9/2001 |
| WO | WO 01/70741 | 9/2001 |
| WO | WO 02/22597 | 3/2002 |
| WO | WO 02/49413 | 6/2002 |
| WO | WO 02/068574 | 9/2002 |
| WO | WO 02/068577 | 9/2002 |
| WO | WO 02/070541 | 9/2002 |
| WO | WO 02/083126 | 10/2002 |
| WO | WO 03/004489 | 1/2003 |
| WO | WO 03/051276 | 6/2003 |
| WO | WO 03/070241 | 8/2003 |
| WO | WO 03/093297 | 11/2003 |
| WO | WO 2004/004725 | 1/2004 |
| WO | WO 2004/011456 | 2/2004 |
| WO | WO 2004/063147 | 7/2004 |
| WO | WO 2004/066725 | 8/2004 |
| WO | WO2004/069801 | 8/2004 |
| WO | WO 2004/069801 | 8/2004 |
| WO | WO 2004/076640 | 9/2004 |
| WO | WO 2004/080492 | 9/2004 |
| WO | WO 2004/085382 | 10/2004 |
| WO | WO 2004/099371 | 11/2004 |
| WO | WO 2005/010017 | 2/2005 |
| WO | WO 2005/012252 | 2/2005 |
| WO | WO 2005/023183 | 3/2005 |
| WO | WO 2005/039489 | 5/2005 |
| WO | WO 2005/046604 | 5/2005 |
| WO | WO 2005/073189 | 8/2005 |
| WO | WO 2005/073216 | 8/2005 |
| WO | WO 2005/073217 | 8/2005 |
| WO | WO 2005/087211 | 9/2005 |
| WO | WO 2005/107463 | 11/2005 |
| WO | WO 2005/116039 | 12/2005 |
| WO | WO 2006/009765 | 1/2006 |
| WO | WO 2006/069080 | 6/2006 |
| WO | WO 2006/069807 | 7/2006 |
| WO | WO 2006/081425 | 8/2006 |
| WO | WO 2006/088919 | 8/2006 |
| WO | WO 2006/095542 | 9/2006 |
| WO | WO 2006/127379 | 11/2006 |
| WO | WO 2006/128129 | 11/2006 |
| WO | WO 2006/128172 | 11/2006 |
| WO | WO 2006/130462 | 12/2006 |
| WO | WO 2007/000432 | 1/2007 |
| WO | WO 2007/037898 | 4/2007 |
| WO | WO 2007/050980 | 5/2007 |
| WO | WO 2007/060404 | 5/2007 |
| WO | WO 2007/106503 | 9/2007 |
| WO | WO 2008/083491 | 7/2008 |
| WO | WO 2008/148074 | 12/2008 |
| WO | WO 2009/079797 | 7/2009 |

OTHER PUBLICATIONS

Sugimoto et al., "Activation of Dithiocarbamate by 2-Halothiazolium Salts", 1988, J. Org. Chem., 53, pp. 2263-2267.

Heinisch et al., "Synthesen und Reaktionen von Pyridazinderviaten", 1973, Monatshefte fur Chemie 104, pp. 1372-1382.

Braun et al., "4,5-Diacylpyridazine: Synthese und Umsetzung zu 1,4-Diaryl- bzw. 1,4-Dialkyl-pyridazino [4,5-d] pyridazinen" 1978, Monatshefte fur Chemie 109, pp. 63-71.

Rusinov et al., "New reaction of 3,6-bis(2-pyridyl)-1,2,4,5-tetrazine with anhydro base of 1,2,3-trimethylquinoxalinium and intramolecular aminolysis of the resulting azomethine", 1981, (abstract).

Suzuki et al., Preparation of diphenylmethylimine derivatives as antiinflammatories, *antitumors, and lipoxygenase and cyclooxygenase inhibitors, 1987 (abstract).

West et al., "Copper(II) complexes of 2-formyl-, 2-acetyl- and 2-benzoy-pyridine N(4)-phenyl-, N(4)-o-methoxyphenyl-, N(4)-p-methoxy-phenyl-and N(4)-p-nitrophenylthiosemicarbazones", 1996, Transition Met. Chem., 21, pp. 213-218.

West et al., "Copper(II) complexes of 2-formyl-, 2-acetyl- and 2-benzoylpyridine N(4)-o-, N(4)-m-, N(4)-p-chlorophenylthiosemicarbazones", 1996, Transition Met. Chem., 21, pp. 52-57.

Kalinowski et al., "Design, Synthesis, and Characterization of Novel Iron Chelators: Structure-Activity Relationships of the 2-Benzoylpyridine Thiosemicarbazone Series and Their 3-Nitrobenzoyl Analogues as Potent Antitumor Agents", 2007, J. Med. Chem., 50, pp. 3716-3729.

Wang et al., "Preparation of heteroaryl substituted hydrazinecarbothioamide compounds for treatment of cancer", 2007 (abstract).

West et al., "Copper(II) complexes of 2-formyl-, 6-methyl-2-formyl- and 2-benzoylpyridine N(4)-(2-methylpyridinyl)-,N(4)-(2-ethylpyridinyl)-and N(4)-methyl(2-ethylpyridinyl) thiosemicarbazones", 1996, Transition Met. Chem., 21, pp. 289-295.

Agrawal et al., "Potential Antitumor Agents. 11. Inhibitors of Alkaline Phosphatase, an Enzyme Involved in the Resistance of Neoplastic Cell to 6-Thiopurines", 1974, Journal of Medicinal Chemistry, vol. 17, No. 9, pp. 934-938.

Miller III, et al., "The Cytotoxicity of Copper(II) Complexes of 2-Acetyl-Pyridyl-N-Substituted Thiosemicarbazones", 1998, Anticancer Research 18, pp. 4131-4140.

Easmon et al., "Synthesis and Antiviral Activity of Thiosemicarbazone Derivatives of Pyridazinecarbaldehydes and Alkyl Pyridazinyl Ketones", 1989, Arzneim-Forsch/Drug Res. 39 (II), No. 10.

Europe Application No. 08700510.4-2117 Examination Report mailed Feb. 22, 2012.

CHEMCATS record, CAS Registry No. 903274-24-8, 903180-32-5, 901391-84-2, 901360-35-8, 901360-08-5, 901349-50-6, 901348-18-3, 901329-97-3, 90285-15-2, 847046-07-5, 802269-45-0, 733793-43-6, 732992-68-6, 732257-35-1, 519151-42-9, 501650-12-0, 500300-93-6 (10 pages).

Akashi et al. (2008) Br J Cancer 98: 749-755, "Enhancement of the antitumor activity of ionising radiation by nimotuzumab, a humanized monoclonal antibody to the epidermal growth factor receptor, in non-small cell lung cancer cell lines of differing epidermal growth factor receptor status" abstract.

Akcakanat et al. (2007) Biochem Biophys Res Commun 362: 330-333, "Rapamycin regulates the phosphorylation of rictor." abstract.

Alessi et al. (1997) Curr Biol 7: 261-269, "Characterization of a 3-phosphoinositide-dependent protein kinase which phosphorylates and activates protein kinase Balpha" abstract.

Alessi et al. (1997) Curr Biol 7: 776-789, "3-Phosphoinositide-dependent protein kinase-1 (PDK1): structural and functional homology with the Drosophila DSTPK61 kinase" abstract.

Al-Shahrour et al. (2007) Nucleic Acids Research 35:w91-w96, "FatiG01: a functional profiling tool for genomic data. Integration of functional annotation, regulatory motifs and interaction data with microarray experiments".

Altomare et al. (2004) Oncogene 23: 5853-5857, "AKT and mTOR phosphorylation is frequently detected in ovarian cancer and can be targeted to disrupt ovarian tumor cell growth" abstract.

Altomare et al. (2005) Oncogene 24: 7455-7464, "Perturbations of the AKT signaling pathway in human cancer" abstract.

Ananthanarayanan et al. (2007) J Biol Chem 282: 36634-36641, "Live-cell molecular analysis of Akt activation reveals roles for activation loop phosphorylation" abstract.

Anderson et al., "Some Heterocyclic Thiosemicarbazones", Oct. 1951, Journal of the American Chemical Society, vol. 73, p. 4967-4968.

Andes et al. (2002) International Journal of Antimicrobial Agents, 19:261-268, "Animal model pharmacokinetics and pharmacodynamics: a critical review".

Andrews et al. (1990) Cancer Communications 2(2):93-100, "Rapid emergence of acquired cis-Diamminedichloroplatinum(ll) Resistance in an in vivo model of human ovarian carcinoma".

Attoub et al. (2002) Cancer Research 62:4879-4883, "The c-kit tyrosine kinase inhibitor STI571 for colorectal cancer therapy".

Bain et al. (1997) Polyhedron 16(5):855-862, Synthetic and spectroscopic investigations of.

Banker et al. (2002) Journal of Pharmaceutical Sciences 92(5):967-974, "Development and validation of a 96-well equilibrium dialysis apparatus for measuring plasma protein binding".

Bastos et al., (2005) Tetrahedron, vol. 61, p. 7045-7053, "Structural analyses of 4-benzoylpyridine thiosemicarbazone using NMR techniques and theoretical calculations".

Bauer (1963) British Journal of Experimental Pathology, 44, 233-42, "The Chemotherapy of Ectromelia Infection with Isatin β-Dialkylthiosemicarbazones".

Beeram et al. (2005) J Clin Onco 23: 6771-6790, "Raf: a strategic target for therapeutic development against cancer" abstract.

Bellacosa et al. (2005) Adv Cancer Res 94: 29-86, "Activation of AKT kinases in cancer: implications for therapeutic targeting" abstract.

Beraldo et al., (2003) Journal of Molecular Structure, vol. 645, p. 213-220"Structural studies and spectral characteristics of 4-benzoylpyridine thiosemicarbazone and N(4')-phenyl-4-benzoylpyridine thiosemicarbazone".

Bernhardt et al. (2003) Journal of Biological Inorganic Chemistry pp. 866-880, "Cytotoxic iron chelators: characterization of the structure, solution chemistry and redox activity of ligands and iron complexes of the di-2-pyridyl ketone isonicotinoyl hydrazone (HPKIH) analogues" http://dx.doi.org/IO.IOO7/s00775-003-0486-z.

Bernhardt et al (2008) Journal of Biological Inorganic Chemistry 13:107-119, "Tuning the antiproliferative activity of biologically active iron chelators: characterization of the coordination chemistry and biological efficacy of 2-acetylpyridine and 2-benzoylpyridine hydrazone ligands".

Berns et al. (2007) Cancer Cell 12:395-402, "A Functional Genetic Approach Identifies the PI3K Pathway as a Major Determinant of Trastuzumab Resistance in Breast Cancer".

Bjornsson et al. (2003) Drug Metabolism and Disposition 31:815-832, "The conduct of in vitro and in vivo drug-drug interaction studies: a pharmaceutical research and manufacturers of america (phrma) perspective".

Bjornsti et al. (2004) Nat Rev Cancer 4: 335-348 Ref ID: 154, "The TOR pathway: a target for cancer therapy" abstract.

Bolen (1993) Oncogene 8:2025-2031, "Nonreceptor tyrosine protein kinases".

Bondar et al. (2002) Mol Cancer Ther 1: 989-997, "Inhibition of the phosphatidylinositol 3'-kinase-AKT pathway induces apoptosis in pancreatic carcinoma cells in vitro and in vivo" abstract.

Bose et al. (2009) Exp Cell Res 315: 649-658, "The ErbB kinase domain: structural perspectives into kinase activation and inhibition" abstract.

Bowery et al. (2005) Current Opinion in Pharmacology 5(4):341-448, "Cancer/Immunomodulation".

Braun (1978) Monatshefte fur Chemie 109:63-71, "4,5•Diacylpyridazine: Synthese und Umsetzung zu 1,4-Diaryl-bzw. 1,4-Dialkyl-pyridazino[4,5—d]pyridazinen" English Abstract.

Braun et al. (2008) Clin Cancer Res 14: 2249-2252, "Targeting Ras in myeloid leukemias" abstract.

Britten et al. (1999) Cancer Research 59:1049-1053, "Enhanced antitumor activity of 6-hydroxymethylacylfulvene in combination with irinotecan and 5-fluorouracil in the HT29 human colon tumor xenograft model".

Brognard et al. (2001) Cancer Res 61: 3986-3997, "Akt/protein kinase B is constitutively active in non-small cell lung cancer cells and promotes cellular survival and resistance to chemotherapy and radiation" abstract.

Brunn et al. (1996) The EMBO Journal 15(19):5256-5267, "Direct inhibition of the signaling functions of the mammalian target of rapamycin by the phosphoinositide 3-kinase inhibitors, wortmannin and LV294002".

Buck et al. (2006) Mol Cancer Ther 5: 2676-2684, "Rapamycin synergizes with the epidermal growth factor receptor inhibitor erlotinib in non-small-cell lung, pancreatic, colon, and breast tumors" abstract.

Canadian Intellectual Property Office acting as International Searching Authority, International Search Report and Written Opinion prepared Mar. 2, 2009 for International Application No. PCT/CA2008/002293, 12 pages.

Canadian Intellectual Property Office acting as International Searching Authority, International Search Report prepared Apr. 28, 2008 for International Application No. PCT/CA2008/000045, 5 pages.

Canadian Intellectual Property Office acting as International Searching Authority, International Search Report prepared Sep. 22, 2009 and Written Opinion prepared Oct. 28, 2009 for International Application No. PCT/CA2009/001004, 15 pages.

Canadian Intellectual Property Office acting as International Searching Authority, Written Opinion of the International Searching Authority prepared Apr. 28, 2008 for International Application No. PCT/CA2008/000045, 6 pages.

Caron et al. (2005) Mol Cancer Ther 4: 257-270, "Activated forms of H-RAS and K-RAS differentially regulate membrane association of PI3K, PDK-1, and AKT and the effect of therapeutic kinase inhibitors on cell survival" abstract.

CAS Registry No. 76780-41-1, 2 pages.

Castagnola et al. (2005) Biochim Biophys Acta 1756: 115-125, "Mutant KRAS, chromosomal instability and prognosis in colorectal cancer" abstract.

Castillo et al. (2004) Cancer Res 64: 2782-2792, "Preferential inhibition of Akt and killing of Akt-dependent cancer cells by rationally designed phosphatidylinositol ether lipid analogues."

Castro-Carpeno et al. (2008) Clin Transl Onco/1 0: 6-13, "EGFR and colon cancer: a clinical view" abstract.

Cespedes et al. (2006) Carcinogenesis 27: 2190-2200, "K-ras Asp12 mutant neither interacts with Raf, nor signals through Erk and is less tumorigenic than K-ras Val 12" abstract.

Chadha et al. (2006) Ann Surg Oncol 13: 933-939, "Activated Akt and Erk expression and survival after surgery in pancreatic carcinoma" abstract.

Chau et al. (2009) Br J Cancer 100:1704-1719, "Treatment in advanced colorectal cancer: what, when and how?" abstract.

Chen et al. (2001) J Biol Chem 276: 31858-31862, "Regulation of Akt/PKB activation by tyrosine phosphorylation" abstract.

Cheng et al. (1992) Proc Natl Acad Sci U S A 89: 9267-9271, "AKT2, a putative oncogene encoding a member of a subfamily of protein-serine/threonine kinases, is amplified in human ovarian carcinomas" abstract.

Cheng et al. (1996) Proc Natl Acad Sci U S A 93: 3636-3641, "Amplification of AKT2 in human pancreatic cells and inhibition of AKT2 expression and tumorigenicity by antisense RNA" abstract.

Cheng et al. (2005) Oncogene 24: 7482-7492, "The Akt/PKB pathway: molecular target for cancer drug discovery" abstract.

Chiang et al. (2007) Trends in Molecular Medicine 13:433-442, "Targeting the mTOR signaling network in cancer".

Chiang et al. (2007) Trends in Molecular Medicine 13:433-442, "Targeting the mTOR signaling network in cancer" abstract.

Chou et al. (1983) Trends in Pharm Sci 4:450-454, "Analysis of combined drug effects: a new look at a very old problem".

Chou (2006) Pharmacol Rev 58:621-681, "Theoretical Basis, Experimental Design, and Computerized Simulation of Synergism and Antagonism in Drug Combination Studies".

Choudhary et al. (1998) Journal of the Indian Chemical Society, 75, 392-394, "Structural Aspects of Morpholine-N-thiohydrazone Complexes with some Bivalent Metals".
Clark et al. (2002) Mol Cancer Ther 1: 707-717, "Constitutive and inducible Akt activity promotes resistance to chemotherapy, trastuzumab, or tamoxifen in breast cancer cells" abstract.
Copp et al. (2009) Cancer Res 69: 1821-1827, "TORC-specific phosphorylation of mammalian target of rapamycin (mTOR): phospho-Ser2481 is a marker for intact mTOR signaling complex 2" abstract.
Cully et al. (2006) Nature 6:184-192, "Beyond PTEN mutations: the PI3K pathway as an integrator of multiple inputs during tumorigenesis".
Dacic, S. (2008) Adv Anat Pathol 15: 241-247, "EGFR assays in lung cancer" abstract.
Datta et al. (1999) Genes Dev 13: 2905-2927, "Cellular survival: a play in three Akts" abstract.
Daunis et al. (1970) Bull. Soc. Chim. Fr., No. 6:2289-2291, "Semicarbazones et thiosemicarbazones N-4 substituees de l'isatine".
de Gunzburg, J. (1999) Cell Biol Toxicol 15: 345-358, "Proteins of the Ras pathway as novel potential anticancer therapeutic targets" abstract.
Decaudin (2005) Int. J. Cancer 113:849-856, "In vivo efficacy of STI571 in xenografted human small cell lung cancer alone or combined with chemotherapy".
Defeo-Jones et al. (2005) Mol Cancer Ther 4:271-279, "Tumor cell sensitization to apoptotic stimuli by selective inhibition of specific Akt/PKB family members" abstract.
DeGraffenried et al. M (2004) Ann Oncol 15: 1510-1516, "Reduced PTEN expression in breast cancer cells confers susceptibility to inhibitors of the PI3 kinase/Akt pathway" abstract.
Deramaudt T, Rustgi AK (2005) Biochim Biophys Acta 1756:97-101, "Mutant KRAS in the initiation of pancreatic cancer".
Dierks et al. (2001) Drug Metabolism and Disposition 29:23-29, "A method for the simultaneous evaluation of the activities of seven major human drug-metabolizing cytochrome P450S using an in vitro cocktail of probe substrates and fast gradient liquid chromatography tandem mass spectrometry".
Dobashi et al. (2009) Cancer 115: 107-118, "Critical and diverse involvement of Akt/mammalian target of rapamycin signaling in human lung carcinomas" abstract.
Doody et al. (2007) Mol Cancer Ther 6: 2642-2651, "Inhibitory activity of cetuximab on epidermal growth factor receptor mutations in non small cell lung cancers" abstract.
Dowling et al. (2009) BioDrugs 23: 77-91, "Current status and challenges associated with targeting mTOR for cancer therapy" abstract.
Downward, J. (2003) Nat Rev Cancer 3: 11-22, "Targeting RAS signalling pathways in cancer therapy" abstract.
Du K, Tsichlis PN (2005) Oncogene 24: 7401-7409, "Regulation of the Akt kinase by interacting proteins" abstract.
Duca et al., (1952) Antibiotics and Chemotherapy, II(1):16-20, "Studies in Experimental Tuberculosis in Vitro and in Vivo Activities of Thiosemicarbazones".
Dwivedi et al. (1995) J. Indian Chem. Soc. 72:403-405, "Donor Behaviour of some Motpholine-N-thiohydrazoneswith some Bivalent Metal Ions".
Dziadulewicz et al. (2001) Bioorganic and Medicinal Organic Letters, 11, 705-709, "Design of Non-Peptide $CCK_2$ and $NK_1$ Peptidomimetics Using 1-(2-Nitrophenyl)thiosemicarbazide as a Novel Common Scaffold".
El Rayes et al. (2006) Cancer Res 66: 10553-10559, "Potentiation of the effect of erlotinib by genistein in pancreatic cancer: the role of Akt and nuclear factor-kappaB" abstract.
Eliel et al. (1994) A Wiley-Interscience Publication: Stereochemistry of Organic Compounds, ch.14:1119-1190, "Chirality in molecilles devoid of chiral centers".
Ellis et al. (2000) Cell Signal 12: 425-434, "The importance of being K-Ras" abstract.
Engelman et al. (2008) Clin Cancer Res 14: 2895-2899, "Mechanisms of acquired resistance to epidermal growth factor receptor tyrosine kinase inhibitors in non-small cell lung cancer" abstract.

Engelman et al. (2008) Nat Med 14: 1351-1356, "Effective use of PI3K and MEK inhibitors to treat mutant Kras G12D and PIK3CA H1047R murine lung cancers" abstract.
Engelman, JA (2009) Nat Rev Cancer 9: 550-562, "Targeting PI3K signalling in cancer: opportunities, challenges and limitations" abstract.
Fakih M (2008) Curr Treat Options Oncol 9: 357-374, "The role of targeted therapy in the treatment of advanced colorectal cancer" abstract.
Feldman et al. (2009) PLoS Biol 7:e38, "Active-site inhibitors of mTOR target rapamycin-resistant outputs of mTORC1 and mTORC2" abstract.
Fischer et al. (2007) Cancer Treat Rev 33: 391-406, "Targeting receptor tyrosine kinase signalling in small cell lung cancer (SCLC): what have we learned so far?" abstract.
Fotiadou et al. (2007) Mol Cell Biol 27: 6742-6755, "Wild-type NRas and KRas perform distinct functions during transformation" abstract.
Franke et al. (2003) Oncogene 22: 8983-8998, "PI3K/Akt and apoptosis: size matters" abstract.
Franke et al. (2006) The American Journal of Human Genetics 78:1011-1025, "Reconstruction of a functional human gene network, with an application for prioritizing positional candidate genes".
French et al. (1966) J Med Chem 9(4):585-589, "The carcinostatic activity of thiosemicarhazones of formyl heteroaromatic compounds. III. Primary correlation".
Friday et al. (2005) Biochim Biophys Acta 1756: 127-144, "K-ras as a target for cancer therapy" abstract.
Fukui et al. (2008) Gen Thorac Cardiovasc Surg 56: 97-103, "Mutations in the epidermal growth factor receptor gene and effects of EGFR-tyrosine kinase inhibitors on lung cancers" abstract.
Furukawa, T. (2008) J Gastroenterol 43: 905-911, "Molecular targeting therapy for pancreatic cancer: current knowledge and perspectives from bench to bedside".
Gadducci et al. (2008) Gynecol Endocrinol 24: 239-249, "Molecular target therapies in endometrial cancer: from the basic research to the clinic" abstract.
Garassino et al. (2009) Anticancer Res 29: 2691-2701, "Biological and clinical features in predicting efficacy of epidermal growth factor receptor tyrosine kinase inhibitors: a systematic review and meta-analysis" abstract.
Gazdar, AF(2009) Oncogene 28 Suppll: S24-S31, "Activating and resistance mutations of EGFR in non-small-cell lung cancer: role in clinical response to EGFR tyrosine kinase inhibitors" abstract.
Granville et al. (2006) Clin Cancer Res 12(3):679-689, "Handicapping the race to develop inhibitors of the phosphoinositide 3-Kinase/Akt/Mammalian target of rapamycin pathway".
Gres et al. (1998) Pharmaceutical Research 15(5):726-733, "Correlation between oral drug absorption in humans, and apparent drug permeability in TC-7 cells, a human epithelial intestinal cell line: comparison with the parental caco-2 cell line".
Gridelli et al. (2008) Oncologist 13: 139-147, "The potential role of mTOR inhibitors in non-small cell lung cancer".
Guerrero et al. (2002) FASEB J 16: 1642-1644, "Codon 12 and codon 13 mutations at the K-ras gene induce different soft tissue sarcoma types in nude mice" abstract.
Guertin et al. (2007) Cancer Cell 12: 9-22, "Defining the role of mTOR in cancer" abstract.
Gururaj a et al. (2006) Clin Cancer Res 12(12)3831-3842, "R-253 disrupts microtubule networks in multiple tumor cell lines".
Guzeloglu et al. (2004) Biol Reprod 71: 714-721, "In vivo and in vitro regulation of Akt activation in human endometrial cells is estrogen dependent" abstract.
Hartmann et al. (2006) Clin Cancer Res 12: 3019-3027, "Phosphatidylinositol 3'-kinase/AKT signaling is activated in medulloblastoma cell proliferation and is associated with reduced expression of PTEN" abstract.
Hay, N. (2005) Cancer Cell 8: 179-183, "The Akt-mTOR tango and its relevance to cancer".
Heinemann et al. (2009) Cancer Treat Rev 35:262-271, "Clinical relevance of EGFR- and KRAS-status in colorectal cancer patients treated with monoclonal antibodies directed against the EGFR" abstract.

Heinisch et al. (1972) Journal fur Prakt. Chemie. Band 314, 682-698, "Synthesis und Struktur substituierter Isatinthiosemicarbazone und-isothiosemicarbazone".
Helfrich et al. (2006) Clin Cancer Res 12: 7117-7125, "Antitumor activity of the epidermal growth factor receptor (EGFR) tyrosine kinase inhibitor gefitinib (ZD1839, Iressa) in non-small cell lung cancer cell lines correlates with gene copy number and EGFR mutations but not EGFR protein levels" abstract.
Hennessy et al. (2005) Nat Rev Drug Discov 4: 988-1004, "Exploiting the PI3K/AKT pathway for cancer drug discovery" abstract.
Hennessy et al. (2005) Nat Rev Drug Discov 4: 988-1004, "Exploiting the PI3K/AKT pathway for cancer drug discovery".
Hirsch et al. (2006) J Clin Oncol 24: 5034-5042, "Molecular predictors of outcome with gefitinib in a phase III placebo-controlled study in advanced non-small-cell lung cancer" abstract.
Ho Sui et al. (2005) Nucleic Acids Research 33(10)3154-3164, "oPOSSUM: identification of over-represented transcription factor binding sites in co-expressed genes".
Holland et al. (2000) Nat Genet 25: 55-57, "Combined activation of Ras and Akt in neural progenitors induces glioblastoma formation in mice" abstract.
Houlston, RS (2001) Mol Pathol 54: 206-214, "What we could do now: molecular pathology of colorectal cancer" abstract.
Huang et al. (2004) Cancer Res 64: 5355-5362, "Dual-agent molecular targeting of the epidermal growth factor receptor (EGFR): combining anti-EGFR antibody with tyrosine kinase inhibitor" abstract.
Huang et al. (2006) Mol Cell Proteomics 5: 1045-1053, "Interdomain conformational changes in Akt activation revealed by chemical cross-linking and tandem mass spectrometry" abstract.
Huang et al. (2009) Biochem Soc Trans 37: 217-222, "A complex interplay between Akt, TSC2 and the two mTOR complexes" abstract.
Huang et al. (2009) J Formos Med Assoc 108: 180-194, "Induction of Akt activity by chemotherapy confers acquired resistance" abstract.
Hynes et al. (2009) Curr Opin Cell Biol 21: 177-184, "ErbB receptors and signaling pathways in cancer" abstract.
Ikeda et al. (2007) Pathol Int 57: 268-275, "Correlation between EGFR gene mutation pattern and Akt phosphorylation in pulmonary adenocarcinomas" abstract.
Itoh et al. (2002) Cancer 94: 3127-3134, "Phosphorylation of Akt/PKB is required for suppression of cancer cell apoptosis and tumor progression in human colorectal carcinoma" abstract.
Izzard et al. (1999) Cancer Research 59:2581-2586, "Competitive and noncompetitive inhibition of the DNA-dependent protein kinase".
Jacinto et al. (2006) Cell 127: 125-137, "SIN1/MIP1 maintains rictor-mTOR complex integrity and regulates Akt phosphorylation and substrate specificity" abstract.
Janmaat et al. (2003) Clin Cancer Res 9: 2316-2326, "Response to epidermal growth factor receptor inhibitors in non-small cell lung cancer cells: limited antiproliferative effects and absence of apoptosis associated with persistent activity of extracellular signal-regulated kinase or Akt kinase pathways" abstract.
Janmaat et al. (2006) Int J Cancer 118: 209-214, "Enhanced cytotoxicity induced by gefitinib and specific inhibitors of the Ras or phosphatidyl inositol-3 kinase pathways in non-small cell lung cancer cells" abstract.
Janne, PA (2008) Lung Cancer 60 Suppl 2: S3-S9, "Challenges of detecting EGFR T790M in gefitinib/erlotinib-resistant tumours" abstract.
Jetzt et al. (2003) Cancer Res 63: 6697-6706, "Adenoviral-mediated expression of a kinase-dead mutant of Akt induces apoptosis selectively in tumor cells and suppresses tumor growth in mice" abstract.
Ji et al. (2007) J Biol Chem 282: 14048-14055, "Oncogenic KRAS activates hedgehog signaling pathway in pancreatic cancer cells" abstract.
Jiang et al. (2000) Mol Cell Biol 20: 139-148, "The phosphoinositide 3-OH kinase/AKT2 pathway as a critical target for farnesyltransferase inhibitor-induced apoptosis" abstract.
Jiang et al. (2008) Drug Resist Updat 11: 63-76, "Role of mTOR in anticancer drug resistance: perspectives for improved drug treatment" abstract.

Jiang et al. (2009) Adv Cancer Res 102: 19-65, "PI3K/PTEN signaling in angiogenesis and tumorigenesis" abstract.
Jiang et al. (2009) Cancer 115: 3609-3617, "Assessment of K-ras mutation: a step toward personalized medicine for patients with colorectal cancer" abstract.
Jimeno et al. (2009) Cancer J 15: 110-113, "KRAS mutations and susceptibility to cetuximab and panitumumab in colorectal cancer" abstract.
Jimeno et al. (2009) J Clin Oncol 27: 1130-1136, "KRAS mutations and sensitivity to epidermal growth factor receptor inhibitors in colorectal cancer: practical application of patient selection" abstract.
John et al. (2009) Oncogene 28 Suppl 1: S14-S23, "Overview of molecular testing in non-small-cell lung cancer: mutational analysis, gene copy number, protein expression and other biomarkers of EGFR for the prediction of response to tyrosine kinase inhibitors" abstract.
Joshi et al., "Organic Pesticides. Part XIII. Synthesis of Some New Fluoro-ketones and their Thiosemicarbazones", 1963, Journal of Indian Chemical Society, vol. 40, No. 1, p. 42-44.
Kandasamy et al. (2002) Cancer Res 62: 4929-4937, "Role of the phosphatidylinositol 3'-kinase/PTEN/Akt kinase pathway in tumor necrosis factor-related apoptosis-inducing ligand-induced apoptosis in non-small cell lung cancer cells" abstract.
Kang et al. (2008) Int J Gynecol Cancer 18: 1339-1343, "Mutual exclusiveness between PIK3CA and KRAS mutations in endometrial carcinoma" abstract.
Kim et al. (2002) J Biochem Mol Biol 35: 106-115, "Akt: versatile mediator of cell survival and beyond" abstract.
Kimura et al. (2007) Cancer Sci 98: 12751280, "Antibody-dependent cellular cytotoxicity of cetuximab against tumor cells with wild-type or mutant epidermal growth factor receptor" abstract.
Klein et al. (2009) Curr Opin Cell Biol 21 : 185-193, "Targeting the EGFR and the PKB pathway in cancer" abstract.
Kobayashi et al. (2005) N Engl J Med 352: 786792, "EGFR mutation and resistance of non-small-cell lung cancer to gefitinib" abstract.
Konstantinopoulos et al. (2007) Nat Rev Drug Discov 6: 541-555, "Post-translational modifications and regulation of the RAS superfamily of GTPases as anticancer targets" abstract.
Krause et al (2005) New England Journal of Medicine 353(2):172-187 "Tyrosine kinases as targets for cancer therapy".
Kurman et al. (2008) Int J Gynecol Pathol 27: 151-160, "Pathogenesis of ovarian cancer: lessons from morphology and molecular biology and their clinical implications" abstract.
Labisbal et al. (2000) Polyhedron, 19, 1255-1262, "Spectral and structural studies of metal complexes of isatin 3-hexamethyleneiminylthiosemicarbazone prepared electrochemically".
Ladanyi et al. (2008) Mod Pathol 21 Suppl 2: S16-S22, "Lung adenocarcinoma: guiding EGFR-targeted therapy and beyond" abstract.
Laurent-Puig et al. (2008) Curr Opin Onco/20: 454-458, "Lessons from Tarceva in pancreatic cancer: where are we now, and how should future trials be designed in pancreatic cancer?" abstract.
Laurent-Puig et al. (2009) Clin Cancer Res 15: 1133-1139, "Mutations and response to epidermal growth factor receptor inhibitors" abstract.
le Coutre et al. (1999) Jrnl National Cancer Institute 91(2):163-168, In vivo eradication of human BCR/ABL-Positive leukemia cells with an ABL kinase inhibitor.
Lee et al. (2005) Clin Cancer Res 11: 6065-6074, "Response of non-small cell lung cancer cells to the inhibitors of phosphatidylinositol 3-kinase/Akt- and MAPK kinase 4/c-Jun NH2-terminal kinase pathways: an effective therapeutic strategy for lung cancer" abstract.
Lee et al. (2008) Int J Cancer 122: 2380-2384, "Akt1 inhibition by RNA interference sensitizes human non-small cell lung cancer cells to cisplatin" abstract.
Legrier et al. (2007) Cancer Res 67: 11300-11308, "Targeting protein translation in human non small cell lung cancer via combined MEK and mammalian target of rapamycin suppression" abstract.
Lev et al. (2005) Clinical Cancer Research 11:306-314, "Inhibition of platelet-derived growth factor receptor signaling restricts the growth of human breast cancer in the bone of nude mice".

Lievre et al. (2006) Cancer Res 66(8):3992-3995, "KRAS mutation status is predictive of response to cetuximab therapy in colorectal cancer".
Lin et al. (2005) Br J Cancer 93: 1372-1381, "Elevated phosphorylation and activation of PDK-1/AKT pathway in human breast cancer" abstract.
Linardou et al. (2008) Lancet Oneol 9: 962-972, "Assessment of somatic k-RAS mutations as a mechanism associated with resistance to EGFR-targeted agents: a systematic review and meta-analysis of studies in advanced non-small-cell lung cancer and metastatic colorectal cancer" abstract.
Liscovitch et al. (2002) IDrugs 5(4):349-355, "Cancer multidrug resistance: A review of recent drug discovery research".
Lister et al. (1970) Journal of the Chemical Society, 1313-1315, "Potentially Chemotherapeutic Purine Analogues, Part V. Some Hydrazone Derivatives of Pyrazole-4,5-diones and their Cyclisation to Pyrazolo [3,4-e][1,2,4]triazines".
Liu et al. (2007) Clin Cancer Res 13: 67886795, "Relationship of EGFR mutations, expression, amplification, and polymorphisms to epidermal growth factor receptor inhibitors in the NCI60 cell lines." abstract.
Liu et al. (2008) PLoS One 3: e2850, "K-ras/PI3K-Akt signaling is essential for zebrafish hematopoiesis and angiogenesis" abstract.
Liu et al. (2009) Nat Rev Drug Discov 8: 627-644, "Targeting the phosphoinositide 3-kinase pathway in cancer" abstract.
LoPiccolo et al. (2008) Drug Resist Updat 11: 32-50, "Targeting the PI3K/Akt/mTOR pathway: effective combinations and clinical considerations" abstract.
LoPiccolo et al. (2008) Drug Resist Updat 11: 32-50, "Targeting the PI3K/Akt/mTOR pathway: effective combinations and clinical considerations".
Mahoney et al. (2009) Br J Cancer 100: 370-375, "LKB1/KRAS mutant lung cancers constitute a genetic subset of NSCLC with increased sensitivity to MAPK and mTOR signalling inhibition" abstract.
Manning et al. (2007) Cell 129: 1261-1274 Ref ID: 125, "AKT/PKB signaling: navigating downstream" abstract.
Manning (2009) Biochem Soc Trans 37:217-222, "A complex interplay between Akt, TSC2 and the two mTOR complexes" abstract.
MAPK Antibody is used to control for loading and specificity of PTEN siRNA (data obtained from Cell Signaling Technology website, http://www.eellsignal.com/produets/6251.html) 3 pages.
Martelli et al. (2006) Leukemia 20: 911-928, "Phosphoinositide 3-kinase/Akt signaling pathway and its therapeutical implications for human acute myeloid leukemia" abstract.
Massion et al. (2004) Am J Respir Crit Care Med 170: 1088-1094, "Early involvement of the phosphatidylinositol 3-kinase/Akt pathway in lung cancer progression" abstract.
Masure et al. (1999) Eur J Biochem 265: 353-360, "Molecular cloning, expression and characterization of the human serine/threonine kinase Akt-3" abstract.
McCubrey et al. (2008) Adv Enzyme Regul 48: 113-135, "Alteration of Akt activity increases chemotherapeutic drug and hormonal resistance in breast cancer yet confers an achilles heel by sensitization to targeted therapy" abstract.
McNeill (1973) Antimicrobial Agents and Chemotherapy 4(2):105-108, "Inhibition of granulocyte-macrophage colony formation in vitro by substituted isatin thiosemicarbazones".
Memmott (2009) Cell Signal 21: 656-664, "Akt-dependent and -independent mechanisms of mTOR regulation in cancer" abstract.
Meric-Bernstam et al. (2009) J Clin Oncol 27: 2278-2287, "Targeting the mTOR signaling network for cancer therapy" abstract.
Minaguchi et al. (2007) Cancer Lett 248: 112-122, "Combined phospho-Akt and PTEN expressions associated with post-treatment hysterectomy after conservative progestin therapy in complex atypical hyperplasia and stage Ia, G1 adenocarcinoma of the endometrium" abstract.
Missbach (1996) Journal of Biological Chemistry 271, 13515-13522, "Thiazolidine Diones, Specific Ligands of the Nuclear Receptor Retinoid Z Receptor/Retinoid Acid Receptor-related Orphan Receptor α with Potent Antiarthritic Activity".

Monks et al. (1991) National Cancer Institute 83(11)757-766, "Feasibility of a high-flux anticancer drug screen using a diverse panel of cultured human tumor cell lines".
Morgan et al. (1983), International Journal of Applied Radiation and Isotopes, 34(11), 1501-1504, "Synthesis of [1-$^{14}$C]1,2-Cyclohexanedione bis(4-diethylenoxythiosemicarbazone) and Preliminary Biodistribution Studies of this Potential Antitumor Agent".
Morgensztern et al. (2005) Anticancer Drugs 16: 797-803, "PI3K/Akt/mTOR pathway as a target for cancer therapy" abstract.
Nelson et al. (2007) Prostate Cancer Prostatic Dis 10: 331-339, "Inhibition of Akt pathways in the treatment of prostate cancer".
Normanno et al. (2006) Gene 366: 2-16, "Epidermal growth factor receptor (EGFR) signaling in cancer" abstract.
Noske et al. (2007) Cancer Lett 246: 190-200, "Specific inhibition of AKT2 by RNA interference results in reduction of ovarian cancer cell prolifation: increased expression of AKT in advanced ovarian cancer" abstract.
NSC No. 84442-R, National Cancer Institute, 5 pages.
O'Sullivan et al. (1963), Chemotherapia, 7, 17-26, "A Study of the Chemotherapeutic Activity of Isatin β-4',4'-Dialkylthiosemicarbazones against Ectromelia Infection".
O'Sullivan et al. (1963), International Congress of chemotherapy, (1), 879-883, "A Study of Isatin β-Thiosemicarbazone Derivatives in Relation to the Cytopathic Changes Produced by Type 1 and Type 2 Poliovirus on Embryonic Rabbit Kidney Cells in Tissue-Culture".
Oehler-Janne et al. (2008) Biochem Biophys Res Commun 375: 399-404, "Temperature sensitivity of phosphoSer(473)-PKB/AKT" abstract.
Okudela et al. (2004) Am J Pathol 164: 91-100, "K-ras gene mutation enhances motility of immortalized airway cells and lung adenocarcinoma cells via Akt activation: possible contribution to non-invasive expansion of lung adenocarcinoma" abstract.
Ono et al. (2006) Clin Cancer Res 12: 7242-7251, "Molecular mechanisms of epidermal growth factor receptor (EGFR) activation and response to gefitinib and other EGFR-targeting drugs" abstract.
Pacifici et al. (1992) Clin Pharmacokinetics 23(6):449-468, "Methods of determining plasma and tissue binding of drugs. Pharmacokinetic consequences" abstract.
Pandyra et al. (2007) Jrnl Pharmacology and Experimental Therapeutics 322(1):123-132, "Combination silencer RNA (siRNA) targeting Bc1-2 antagonizes siRNA against thymidylate synthase in human tumor cell lines".
Pao et al. (2005) PLoS Med 2: e73, "Acquired resistance of lung adenocarcinomas to gefitinib or erlotinib is associated with a second mutation in the EGFR kinase domain" abstract.
Pao, W (2006) Cancer Chemother Pharmacol 58 Suppl: s11-s15, "Defining clinically relevant molecular subsets of lung cancer" abstract.
Papadimitrakopoulou et al. (2006) J Thorac Oncol 1: 749-751, "The Akt/mTOR and mitogen-activated protein kinase pathways in lung cancer therapy" abstract.
Parikh et al. (2007) Cancer Res 67: 7139-7146, "Oncogenic NRAS, KRAS, and HRAS exhibit different leukemogenic potentials in mice" abstract.
Peterson et al. (2000) Jrnl Biological Chemistry 275(10):7416-7423, FKBP12-Rapamycin-associated protein (FRAP) autophosphorylates at serine 2481 under translationally repressive conditions.
Plesec et al. (2009) Adv Anat Pathol 16: 196-203, "KRAS mutation testing in colorectal cancer" abstract.
Plowman et al. (1994) DN&P 7(6):334-339, "Receptor tyrosine kinases as targets for drug intervention".
Prakash et al. (1989) Indian Drugs 27(2), 106-110, "Synthesis and Screening of N-Morpholino/Piperidino Thiosemicarbazones as Potential Anitmicrobial Agents".
Pretlow et al. (2005) Biochim Biophys Acta 1756: 83-96, "Mutant KRAS in aberrant crypt foci (ACF): initiation of colorectal cancer?" abstract.
Raponi et al. (2008) Curr Opin Pharmacol 8: 413-418, "KRAS mutations predict response to EGFR inhibitors" abstract.

Rhodes et al. (2005) Nature Biotechnology 23(8):951-959, "Probabilistic model of the human protein-protein interaction network".
Riely et al. (2009) Proc Am Thorac Soc 6: 201-205, "KRAS mutations in non-small cell lung cancer" abstract.
Riely, GJ (2008) J Thorac Oncol 3: S146-S149, "Second-generation epidermal growth factor receptor tyrosine kinase inhibitors in non-small cell lung cancer" abstract.
Riely, GJ (2008) Lung Cancer 60 Suppl 2: S19-S22, "The use of first-generation tyrosine kinase inhibitors in patients with NSCLC and somatic EGFR mutations" abstract.
Riondel et al. (1988) Anticancer Research 8:387-390, "Antineoplastic activity of two taxol derivatives on an ovarian tumor xenografted into nude mice".
Rong et al. (2001) J Med Chem 44: 898-908, "Molecular modeling studies of the Akt PH domain and its interaction with phosphoinositides" abstract.
Rosner et al. (2008) Mutat Res 659: 284-292, "The mTOR pathway and its role in human genetic diseases" abstract.
Rosti et al. (2006) Ann Oncol 17 Suppl 5: v99-102, "Chemotherapy advances in small cell lung cancer" abstract.
Ruggeri et al. (1998) Mol Carcinog 21: 81-86, "Amplification and overexpression of the AKT2 oncogene in a subset of human pancreatic ductal adenocarcinomas" abstract.
Ruggero et al. (2005) Oncogene 24: 7426-7434, "The Akt of translational control" abstract.
Sabatini, DM (2006) Nat Rev Cancer 6: 729-734, "mTOR and cancer: insights into a complex relationship" abstract.
Saif et al. (2009) Clin Adv Hematol Onco/7: 45-53, 64, "K-ras mutations in colorectal cancer: a practice changing discovery" abstract.
Sambuy et al. (2005) Cell Biology and Toxicology 21:1-26, "The Caco-2 cell line as a model of the intestinal barrier: infuence of cell and culture-related factors on Caco-2 cell functional characteristics".
Sarbassov et al. (2004) Current Biology 14:1296-1302, "Rictor, a novel binding partner of mTOR, defines a rapamycin-insensitive and raptor-independent pathway that regulates the cytoskeleton".
Sarbassov et al. (2005) Science 307: 1098-1101, "Phosphorylation and regulation of Akt/PKB by the rictor-mTOR complex" abstract.
Schneider et al. (2003) Mol Cancer 2: 15, "Genetic alterations in pancreatic carcinoma" abstract.
Schubbert et al. (2007) Nat Rev Cancer 7: 295-308, "Hyperactive Ras in developmental disorders and cancer" abstract.
Scripture et al. (2006) Nature 6:546-558, "Drug interactions in cancer therapy".
Sebille (1990) Fundam Clin Pharmacol 4(S2):151s-161s, "Methods of drug protein binding determinations".
Seeliger et al. (2007) Cancer Metastasis Rev 26: 611-621, "Role of mTOR in solid tumor systems: a therapeutical target against primary tumor growth, metastases, and angiogenesis" abstract.
Seleem et al. (2002) Journal of the Serbian Chemical Society, 67(4), 243-256, "Thermodynamics of complexation of isatin-3-thiosemicarbazone (HIT) and other related derivatives with some metal ions".
Sequist et al. (2008) Annu Rev Med 59:429-442, "EGFR tyrosine kinase inhibitors in lung cancer: an evolving story" abstract.
Sequist, LV (2008) J Thorac Oncol 3: S143-S145, "First-generation epidermal growth factor receptor tyrosine kinase inhibitors in EGFR mutation: positive non-small cell lung cancer patients" abstract.
Several mutations that abolish PI3-K activity have been described and are catalogued in the human protein mutation database MutDB (http://mutdb.org/) 1 page.
Shaw et al. (2006) Nature 441: 424-430, "Ras, PI(3)K and mTOR signalling controls tumour cell growth" abstract.
She et al. (2008) PLoS One 3: e3065, "Breast tumor cells with PI3K mutation or HER2 amplification are selectively addicted to Akt signaling" abstract.
Sherman et al. (2007) BMC Bioinformatics 8:426-436, "DAVID Knowledgebase: a gene-centered database integrating heterogeneous gene annotation resources to facilitate high-throughput gene functional analysis".
Shridhar et al. (1987) Indian Journal of Chemistry 26B:596-598, "Synthesis & antiparasitic activity of some new 1-(6/7-Nitrobenzoxazin-3-yl)-4-substituted-3-thiosemicarbazides & 4-Disubstituted 3-(6-Acetylbenzoxazin3-one)thiosemicarbazones".
Shtilbans et al. (2008) Ann Diagn Pathol 12: 153-160, "Current overview of the role of Akt in cancer studies via applied immunohistochemistry" abstract.
Siegel-Lakhai et al. (2005) Oncologist 10: 579-589, "Current knowledge and future directions of the selective epidermal growth factor receptor inhibitors erlotinib (Tarceva) and gefitinib (Iressa)" abstract.
Simone (1996) Cecil Textbook of Medicine, 20$^{th}$ Edition 1:1004-1010, "Part XIV Oncology: 154 Introduction".
Smakman et al. (2005) Biochim Biophys Acta 1756: 103-114, "Control of colorectal metastasis formation by K-Ras" abstract.
Spano et al. (2008) Crit Rev Oncol Hematol 66: 21-30, "Potential predictive markers of response to EGFR-targeted therapies in colorectal cancer" abstract.
Steelman et al. (2008) Leukemia 22: 686-707, "Contributions of the Raf/MEK/ERK, PI3K/PTEN/Akt/mTOR and Jak/STAT pathways to leukemia" abstract.
Steiner et al. (2007) Clin Cancer Res 13: 1540-1551, "Tumor growth inhibition with cetuximab and chemotherapy in non-small cell lung cancer xenografts expressing Wild-type and mutated epidermal growth factor receptor" abstract.
Stintzing et al. (2009) Dtsch Arztebllnt 106: 202-206, "The treatment of colorectal carcinoma with monoclonal antibodies: the importance of KRAS mutation analysis and EGFR status" abstract.
Strimpakos et al. (2009) Cancer Treat Rev 35: 148-159, "The role of mTOR in the management of solid tumors: an overview" abstract.
Suda et al. (2009) J Thorac Oncol 4: 1-4, "N(4)-substituted isatin thiosemicarbazones and their copper(II) complexes"EGFR T790M mutation: a double role in lung cancer cell survival? abstract.
Szakács et al. (2006) Nature Reviews Drug Discovery 5:219-234, "Targeting multidrug resistance in cancer".
Szakács et al. (2008) Drug Discovery Today 13(9/10):379-393, "The role of ABC transporters in drug absorption, distribution, metabolism, excretion and toxicity (ADME—Tox)".
Tang et al. (2006) Oncol Rep 15: 855-859, "PTEN sensitizes epidermal growth factor-mediated proliferation in endometrial carcinoma cells" abstract.
Teachey et al. (2009) Br J Haematol 145: 569-580, "Mammalian target of rapamycin inhibitors and their potential role in therapy in leukaemia and other haematological malignancies" abstract.
Testa et al. (2005) Oncogene 24: 7391-7393, "AKT signaling in normal and malignant cells" abstract.
The intersection of common genes was determined using GeneVenn (http://mcbc.usm.edu/genevenn/genevenn.htm) 1 page.
Tomida et al. (2005) Cancer Sci 96: 63-68, "Throwing new light on lung cancer pathogenesis: updates on three recent topics" abstract.
Tzeng et al. (2007) J Surg Res 143: 20-26, "EGFR genomic gain and aberrant pathway signaling in pancreatic cancer patients" abstract.
Undevia et al. (2005) Nature Reviews 5:447-458, "Pharmacokinetic variability of anticancer agents".
Uramoto et al. (2007) Br J Cancer 96: 857-863, "Which biomarker predicts benefit from EGFR-TKI treatment for patients with lung cancer?" abstract.
Van den Bongard et al. (2000) Clinical Pharmacokinetics 39(5):345-367, "Pharmacokinetically Guided Administration of Chemotherapeutic Agents" abstract.
Vanhaesebroeck et al. (2000) Biochem J 346 Pt 3: 561-576, "The PI3K-PDK1 connection: more than just a road to PKB" abstract.
Varughese et al. (1984) Drugs under Experimental and Clinical Research 10(2), 67-74, "A Biodistribution Study of 1-$^{14}$C-1,2-Cyclohexanedione Bis(4-Diethylenoxythiosemicarbazone), A Potential Antitumour Agent".
Venkatakrishnan et al. (2001) J Clin Pharmacol 41:1149-1179, "Human drug metabolism and the cytochromes P450: application and relevance of in vitro models".
Vivanco et al. (2002) Nat Rev Cancer 2: 489-501, "The phosphatidylinositol 3-Kinase AKT pathway in human cancer" abstract.
Walther et al. (2009) Nat Rev Cancer 9: 489-499, "Genetic prognostic and predictive markers in colorectal cancer" abstract.

Wang et al. (2008) Cancer Res 68: 7409-7418, "Enhancing mammalian target of rapamycin (mTOR)-targeted cancer therapy by preventing mTOR/raptor inhibition-initiated, mTOR/rictor-independent Akt activation" abstract.
Weng et al. (2009) Cancer Lett 273: 257-265, "Implication of the Akt2/survivin pathway as a critical target in paclitaxel treatment in human ovarian cancer cells" abstract.
Winkelmann et al. (1987) Drug Res 37(1):647-661, "Antimalarial and Anticoccidial Activity of 3-Aryl-7-chloro-3,4-dihydroacridine-1,9-(2H, 1OH)-diones".
Wolber et al. (2006) Methods in Enzymology 410:28-57, "The agilent in situ-synthesized microarray platform".
Wong, KK (2008) Lung Cancer 60 Suppl 2: S10-S18, "Searching for a magic bullet in NSCLC: the role of epidermal growth factor receptor mutations and tyrosine kinase inhibitors".
Yamamoto et al. (2008) Cancer Res 68: 6913-6921, "PIK3CA mutations and copy number gains in human lung cancers" abstract.
Yang et al. (2002) Nat Struct Biol 9: 940-944, "Crystal structure of an activated Akt/protein kinase B ternary complex with GSK3-peptide and AMP-PNP" abstract.
Yap et al. (2008) Curr Opin Pharmacol 8: 393-412, "Targeting the PI3K-AKT-mTOR pathway: progress, pitfalls, and promises" abstract.
Yuan et al. (2000) Oncogene 19: 2324-2330, "Frequent activation of AKT2 and induction of apoptosis by inhibition of phosphoinositide-3-OH kinase/Akt pathway in human ovarian cancer" abstract.
Yuan et al. (2004) Blood 104:1450-1458, "Novel di-2-pyridyl-derived iron chelators with marked and selective antitumor activity: in vitro and in vivo assessment".
Zhang et al. (2005) Proc Natl Acad Sci U S A 102: 14605-14610, "Identification of K-ras as the major regulator for cytokine-dependent Akt activation in erythroid progenitors in vivo" abstract.
Zhang et al. (2007) J Med Genet 44: 166-172, "Somatic mutations of the epidermal growth factor receptor and non-small-cell lung cancer" abstract.
Zhang et al. (2007) Nat Med 13: 1114-1119, "Molecular imaging of Akt kinase activity" abstract.
Zhou (2008) Xenobiotica 38(7-8):802-832, "Structure, function and regulation of P-glycoprotein and its clinical relevance in drug disposition".
Zwick et al (2002) Trends in Molecular Medicine 8(1):17-23, "Receptor tyrosine kinases as targets for anticancer drugs" abstract.
European Supplemental Search Report for EP Application No. 09797322 mailed Dec. 20, 2011.
McNeill, "Inhibition of Granulocyte-Macrophage Colony Formation in Vitro by Substituted Isatin Thiosemicarbazones", Aug. 1, 1973, vol. 4, No. 2, pp. 105-108.
Pectasides, et al., "Systemic therapy in metastatic or recurrent endometrial cancer", Mar. 3, 2007, Cancer Treatment Reviews, Saunders, US, vol. 33, No. 2, pp. 177-190.
International Search Report for International Application No. PCT/US2005/021253 mailed Mar. 29, 2006.
Sequence Listing for International Application No. PCT/US2005/021253.
U.S. Appl. No. 13/363,558, filed Feb. 1, 2012 entitled "Inhibitor Compounds and Cancer Treatment Methods" by Wayne R. Danter.
Byrn et al., Solid-State Chemistry of Drugs, 516 (2nd ed., 1999). "Hydrates are a subset of solvates wherein the solvent is water", id. at 233-247, pp. 233-234.
Easmon et al., "Pyridazines 47,1 The Configuration of Novel Thiosemicarbazone Derivatives of Pyridazinecarbaldehydes and Alkyl Pyridazinyl Ketones", 1989, Heterocycles, vol. 29, No. 7, pp. 1399-1408.
CAS Registry No. 868364-38-9, Nov. 18, 2005.
CAS Registry No. 868364-43-6, Nov. 18, 2005.
CAS Registry No. 901285-15-2, Aug. 15, 2006.
CAS Registry No. 901329-97-3, Aug. 15, 2006.
CAS Registry No. 901348-18-3, Aug. 15, 2006.
CAS Registry No. 901349-50-6, Aug. 15, 2006.
CAS Registry No. 901360-08-5, Aug. 15, 2006.
CAS Registry No. 901391-84-2, Aug. 15, 2006.
CAS Registry No. 903180-32-5, Aug. 22, 2006.
CAS Registry No. 903274-24-8, Aug. 26, 2006.
CAS Registry No. 91189-95-6, Nov. 16, 1984.
CAS Registry No. 500300-93-6, Mar. 24, 2003.
CAS Registry No. 518299-22-4, May 21, 2003.
CAS Registry No. 519151-42-9, May 23, 2003.
CAS Registry No. 549530-64-5, Jul. 17, 2003.
CAS Registry No. 732257-35-1, Aug. 25, 2004.
CAS Registry No. 732992-68-6, Aug. 26, 2004.
CAS Registry No. 733793-43-6, Aug. 27, 2004.
CAS Registry No. 802269-45-0, Dec. 23, 2004.
CAS Registry No. 847046-07-5, Mar. 23, 2005.
CAS Registry No. 852401-92-4, Jun. 16, 2005.
CAS Registry No. 852401-95-7, Jun. 16, 2005.
Office Action for CA 2,673,683 mailed Jan. 28, 2013, 8 pages.

* cited by examiner

COMPOUNDS AND METHOD FOR TREATMENT OF CANCER

STATEMENT OF RELATED APPLICATIONS

The present application is a continuation of pending U.S. application Ser. No. 13/190,230 filed on Jul. 25, 2011, which is a divisional of U.S. application Ser. No. 12/013,079, filed Jan. 11, 2008, (now U.S. Pat. No. 8,034,815), which claims the benefit of U.S. provisional application U.S. Ser. No. 60/884,489, filed Jan. 11, 2007, which also claims benefit of U.S. provisional application U.S. Ser. No. 60/884,504, filed Jan. 11, 2007, each of which are incorporated herein by reference in their entireties.

FIELD OF THE INVENTION

The present invention relates generally to compounds, compositions and methods for treatment of cancer.

BACKGROUND OF THE INVENTION

Cancer, irrespective of its pathogenesis, is characterized by uncontrolled growth and survival of cells. Common to most forms of cancer is an error in the cellular mechanism responsible for balancing cell survival and cell death.

According to the American Cancer Society, lung cancer is the leading cause of cancer death for both men and women. Small cell lung cancer (SCLC) accounts for approximately 20% of all lung cancers. The 5-year survival rate for small cell lung cancer is about 15%.

Certain thiosemicarbazones, such as those disclosed in British Patent No. 1,026,401, International Patent Application No. WO2004/066725, Japanese Patent No. 56-95161 and U.S. Pat. No. 4,927,843, have been used to treat, for example, a variety of viruses. Other thiosemicarbazones, however, may be used to treat cancer. French Patent No. 2,879,194 is directed to certain thiosemicarbazones that may be used in the treatment or prevention of cancer, in dermatological treatment, in the treatment of cardiovascular and immune diseases, lipid-metabolism related diseases and modulate PPAR's. International Patent Application No. WO 2006/009765 is directed to specific thiosemicarbazones that may be used in anti-cancer therapy that mitigates the development of drug resistance. U.S. Pat. No. 4,593,027 is directed to hydrazone derivatives that may be used as a chemotherapeutic.

There is a need, however, for new therapeutic drug treatments to treat cancers more efficiently, and lung cancer in particular. Current treatment regimes for small cell lung cancer involve surgery, radiation and chemotherapy. While timely surgery can be curative, new therapies are necessary when timely surgery is not an option.

All patents and patent applications referenced herein are incorporated by reference herein in their entireties.

SUMMARY OF THE INVENTION

In accordance with an aspect, there is provided a compound of Formula I:

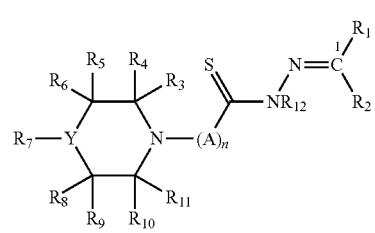

Formula I and/or a pharmaceutically-acceptable salt, hydrate, solvate, tautomer, optical isomer, or combination thereof; wherein:

$R_1$ and $R_2$ together form a substituted or unsubstituted polycyclic ring comprising at least two ring systems, said at least two ring systems comprising a first ring system bonded to C1 and a second ring system fused to the first ring system, wherein:

the first ring system is a substituted or unsubstituted aromatic group, the second ring system is a substituted or unsubstituted aromatic group, a substituted or unsubstituted heteroaromatic group, a substituted or unsubstituted carbocyclic group, or a substituted or unsubstituted heterocyclic group; or the first ring system is a substituted or unsubstituted heteroaromatic group, the second ring system is a substituted or unsubstituted aromatic group, a substituted or unsubstituted heteroaromatic group, a substituted or unsubstituted carbocyclic group, or a substituted or unsubstituted heterocyclic group; or the first ring system is a substituted or unsubstituted saturated carbocyclic group, the second ring system is a substituted or unsubstituted aromatic group, a substituted or unsubstituted unsaturated carbocyclic group, a substituted or unsubstituted heterocyclic group, or a substituted or unsubstituted ring B:

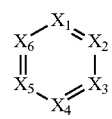

Ring B wherein $X_1$ to $X_6$ are each independently selected from carbon or a heteroatom; or the first ring system is a substituted or unsubstituted unsaturated carbocyclic group, the second ring system is a substituted or unsubstituted aromatic group, a substituted or unsubstituted carbocyclic group, a substituted or unsubstituted heterocyclic group, or a substituted or unsubstituted ring B:

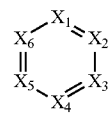

Ring B wherein $X_1$ to $X_6$ are each independently selected from carbon or a heteroatom; or the first ring system is a substituted or unsubstituted heterocyclic group, the second ring system is a substituted or unsubstituted heteroaromatic group, a substituted or unsubstituted carbocyclic group, or a substituted or unsubstituted heterocyclic group; and $R_3$ to $R_{11}$ are each independently selected from H, a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic;

$R_{12}$ is selected from H or a hydrocarbyl group;

Y is selected from a heteroatom or a carbon atom;

A is selected from a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic; and n is an integer.

In a further aspect, there is provided a composition comprising the compound of Formula I.

In another aspect, there is provided a method of administration of the compound of Formula I or composition thereof to treat a cancer.

In yet another aspect, there is provided use of the compound of Formula I or composition thereof to treat a cancer.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from the detailed description.

BRIEF DESCRIPTION OF THE DRAWINGS

Embodiments of the present invention will now be described, by way of example only, with reference to the attached Figures.

DETAILED DESCRIPTION

Figure 1:
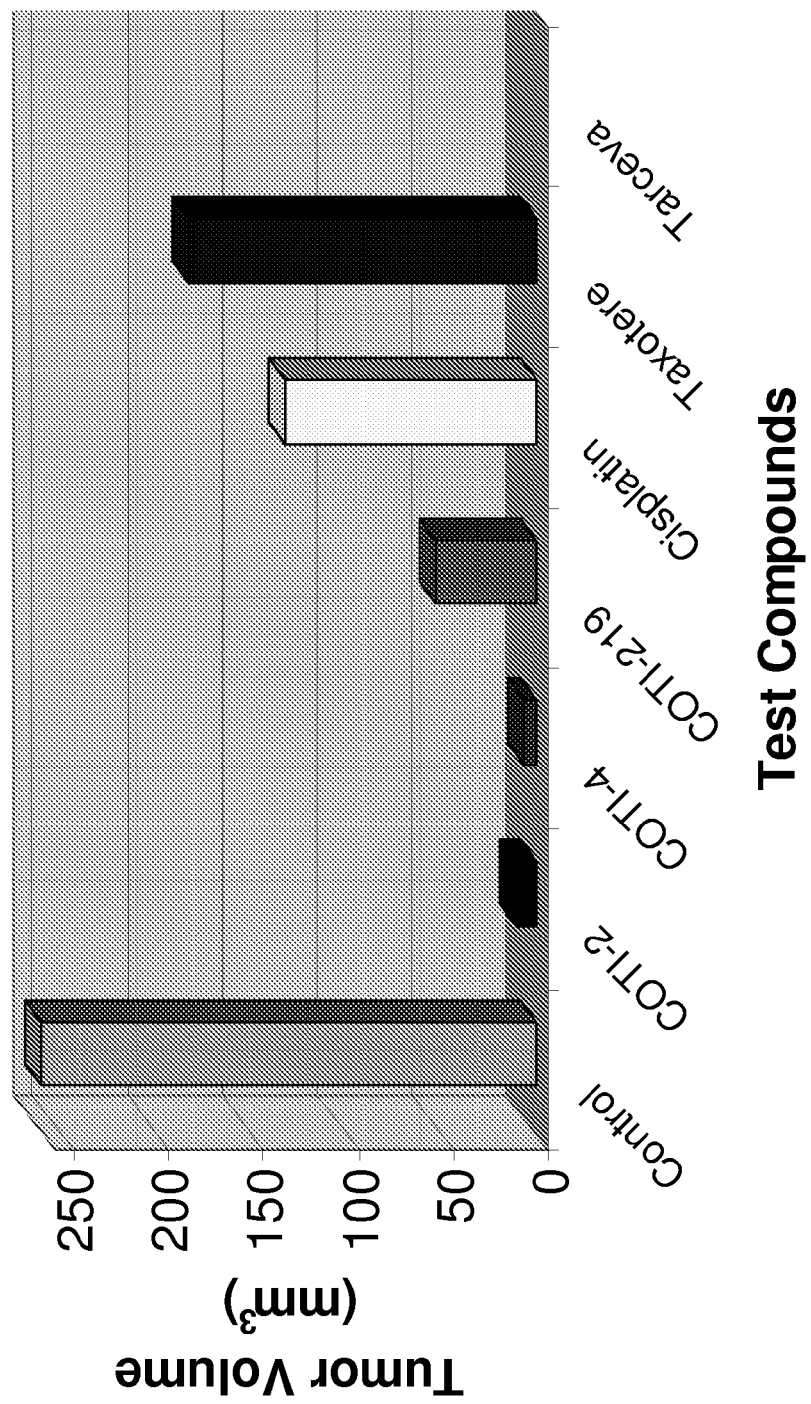
FIG. 1 shows the volume of SHP77 human SCLC tumour in nude mice treated with test compounds.

The present invention is directed to a thiosemicarbazone, a composition comprising the thiosemicarbazone, a method of administration thereof, and use thereof to treat a cancer.

Definitions

When describing the compounds, compositions, methods and uses of this invention, the following terms have the following meanings unless otherwise indicated.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The compounds of the present invention may have asymmetric centers, chiral axes, and chiral planes (as described, for example, in: E. L. Eliel and S. H. Wilen, Stereo-chemistry of Carbon Compounds, John Wiley & Sons, New York, 1994, pages 1119-1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure may be depicted.

Generally, reference to a certain element such as hydrogen or H is meant to, if appropriate, include all isotopes of that element.

Where the term "alkyl group" is used, either alone or within other terms such as "haloalkyl group" and "alkylamino group", it encompasses linear or branched carbon radicals having, for example, one to about twenty carbon atoms or, in specific embodiments, one to about twelve carbon atoms. In other embodiments, alkyl groups are "lower alkyl" groups having one to about six carbon atoms. Examples of such groups include, but are not limited thereto, methyl, ethyl, n-propyl, isopropyl, n-butyl, isobutyl, sec-butyl, tert-butyl, pentyl, iso-amyl, hexyl and the like. In more specific embodiments, lower alkyl groups have one to four carbon atoms.

The term "alkenyl group" encompasses linear or branched carbon radicals having at least one carbon-carbon double bond. The term "alkenyl group" can encompass conjugated and non-conjugated carbon-carbon double bonds or combinations thereof. An alkenyl group, for example and without being limited thereto, can encompass two to about twenty carbon atoms or, in a particular embodiment, two to about twelve carbon atoms. In embodiments, alkenyl groups are "lower alkenyl" groups having two to about four carbon atoms. Examples of alkenyl groups include, but are not limited thereto, ethenyl, propenyl, allyl, propenyl, butenyl and 4-methylbutenyl. The terms "alkenyl group" and "lower alkenyl group", encompass groups having "cis" and "trans" orientations, or alternatively, "E" and "Z" orientations.

The term "alkynyl group" denotes linear or branched carbon radicals having at least one carbon-carbon triple bond. The term "alkynyl group" can encompass conjugated and non-conjugated carbon-carbon triple bonds or combinations thereof. Alkynyl group, for example and without being limited thereto, can encompass two to about twenty carbon atoms or, in a particular embodiment, two to about twelve carbon atoms. In embodiments, alkynyl groups are "lower alkynyl" groups having two to about ten carbon atoms. Some examples are lower alkynyl groups having two to about four carbon atoms. Examples of such groups include propargyl, butynyl, and the like.

The term "halo" means halogens such as fluorine, chlorine, bromine or iodine atoms.

The term "haloalkyl group" encompasses groups wherein any one or more of the alkyl carbon atoms is substituted with halo as defined above. Specifically encompassed are monohaloalkyl, dihaloalkyl and polyhaloalkyl groups including perhaloalkyl. A monohaloalkyl group, for one example, may have either an iodo, bromo, chloro or fluoro atom within the group. Dihalo and polyhaloalkyl groups may have two or more of the same halo atoms or a combination of different halo groups. "Lower haloalkyl group" encompasses groups having 1-6 carbon atoms. In some embodiments, lower haloalkyl groups have one to three carbon atoms. Examples of haloalkyl groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl.

The term "hydroxyalkyl group" encompasses linear or branched alkyl groups having, for example and without being limited thereto, one to about ten carbon atoms, any one of which may be substituted with one or more hydroxyl groups. In embodiments, hydroxyalkyl groups are "lower hydroxyalkyl" groups having one to six carbon atoms and one or more hydroxyl groups. Examples of such groups include hydroxymethyl, hydroxyethyl, hydroxypropyl, hydroxybutyl and hydroxyhexyl.

The term "alkoxy group" encompasses linear or branched oxy-containing groups each having alkyl portions of, for example and without being limited thereto, one to about ten carbon atoms. In embodiments, alkoxy groups are "lower alkoxy" groups having one to six carbon atoms. Examples of such groups include methoxy, ethoxy, propoxy, butoxy and tert-butoxy. In certain embodiments, lower alkoxy groups have one to three carbon atoms. The "alkoxy" groups may be further substituted with one or more halo atoms, such as fluoro, chloro or bromo, to provide "haloalkoxy" groups. In other embodiments, lower haloalkoxy groups have one to three carbon atoms. Examples of such groups include fluoromethoxy, chloromethoxy, trifluoromethoxy, trifluoroethoxy, fluoroethoxy, and fluoropropoxy.

The term "aromatic group" or "aryl group" means an aromatic group having one or more rings wherein such rings may be attached together in a pendent manner or may be fused. In particular embodiments, an aromatic group is one, two or three rings. Monocyclic aromatic groups may contain 4 to 10 carbon atoms, typically 4 to 7 carbon atoms, and more typically 4 to 6 carbon atoms in the ring. Typical polycyclic aromatic groups have two or three rings. Polycyclic aromatic groups having two rings typically have 8 to 12 carbon atoms, preferably 8 to 10 carbon atoms in the rings. Examples of aromatic groups include, but are not limited to, phenyl, naphthyl, tetrahydronaphthyl, indanyl, biphenyl, phenanthryl, anthryl or acenaphthyl.

The term "heteroatom" means an atom other than carbon. Typically, heteroatoms are selected from the group consisting of sulfur, phosphorous, nitrogen and oxygen atoms. Groups containing more than one heteroatom may contain different heteroatoms.

The term "heteroaromatic group" or "heteroaryl group" means an aromatic group having one or more rings wherein such rings may be attached together in a pendent manner or may be fused, wherein the aromatic group has at least one heteroatom. Monocyclic heteroaromatic groups may contain 4 to 10 member atoms, typically 4 to 7 member atoms, and more typically 4 to 6 member atoms in the ring. Typical polycyclic heteroaromatic groups have two or three rings. Polycyclic aromatic groups having two rings typically have 8 to 12 member atoms, more typically 8 to 10 member atoms in the rings. Examples of heteroaromatic groups include, but are not limited thereto, pyrrole, imidazole, thiazole, oxazole, furan, thiophene, triazole, pyrazole, isoxazole, isothiazole, pyridine, pyrazine, pyridazine, pyrimidine, triazine, indole, benzofuran, benzothiophene, benzimidazole, benzthiazole, quinoline, isoquinoline, quinazoline, quinoxaline and the like.

The term "carbocyclic group" means a saturated or unsaturated carbocyclic hydrocarbon ring. Carbocyclic groups are not aromatic. Carbocyclic groups are monocyclic or polycyclic. Polycyclic carbocyclic groups can be fused, spiro, or bridged ring systems. Monocyclic carbocyclic groups may contain 4 to 10 carbon atoms, typically 4 to 7 carbon atoms, and more typically 5 to 6 carbon atoms in the ring. Bicyclic carbocyclic groups may contain 8 to 12 carbon atoms, typically 9 to 10 carbon atoms in the rings.

The term "heterocyclic group" means a saturated or unsaturated ring structure containing carbon atoms and 1 or more heteroatoms in the ring. Heterocyclic groups are not aromatic. Heterocyclic groups are monocyclic or polycyclic. Polycyclic heterocyclic groups can be fused, spiro, or bridged ring systems. Monocyclic heterocyclic groups may contain 4 to 10 member atoms (i.e., including both carbon atoms and at least 1 heteroatom), typically 4 to 7, and more typically 5 to 6 in the ring. Bicyclic heterocyclic groups may contain 8 to 18 member atoms, typically 9 or 10 member atoms in the rings. Representative heterocyclic groups include, by way of example, pyrrolidine, imidazolidine, pyrazolidine, piperidine, 1,4-dioxane, morpholine, thiomorpholine, piperazine, 3-pyrroline and the like.

The term "heterogeneous group" means a saturated or unsaturated chain of non-hydrogen member atoms comprising carbon atoms and at least one heteroatom. Heterogeneous groups typically have 1 to 25 member atoms. More typically, the chain contains 1 to 12 member atoms, 1 to 10, and most typically 1 to 6. The chain may be linear or branched. Typical branched heterogeneous groups have one or two branches, more typically one branch. Typically, heterogeneous groups are saturated. Unsaturated heterogeneous groups may have one or more double bonds, one or more triple bonds, or both. Typical unsaturated heterogeneous groups have one or two double bonds or one triple bond. More typically, the unsaturated heterogeneous group has one double bond.

The term "hydrocarbon group" or "hydrocarbyl group" means a chain of 1 to 25 carbon atoms, typically 1 to 12 carbon atoms, more typically 1 to 10 carbon atoms, and most typically 1 to 8 carbon atoms. Hydrocarbon groups may have a linear or branched chain structure. Typical hydrocarbon groups have one or two branches, typically one branch. Typically, hydrocarbon groups are saturated. Unsaturated hydrocarbon groups may have one or more double bonds, one or more triple bonds, or combinations thereof. Typical unsaturated hydrocarbon groups have one or two double bonds or one triple bond; more typically unsaturated hydrocarbon groups have one double bond.

When the term "unsaturated" is used in conjunction with any group, the group may be fully unsaturated or partially unsaturated. However, when the term "unsaturated" is used in conjunction with a specific group defined herein, the term maintains the limitations of that specific group. For example, an unsaturated "carbocyclic group", based on the limitations of the "carbocyclic group" as defined herein, does not encompass an aromatic group.

The terms "carboxy group" or "carboxyl group", whether used alone or with other terms, such as "carboxyalkyl group", denotes —(C=O)—O—.

The term "carbonyl group", whether used alone or with other terms, such as "aminocarbonyl group", denotes —(C=O)—.

The terms "alkylcarbonyl group" denotes carbonyl groups which have been substituted with an alkyl group. In certain embodiments, "lower alkylcarbonyl group" has lower alkyl group as described above attached to a carbonyl group.

The term "aminoalkyl group" encompasses linear or branched alkyl groups having one to about ten carbon atoms any one of which may be substituted with one or more amino groups. In some embodiments, the aminoalkyl groups are "lower aminoalkyl" groups having one to six carbon atoms and one or more amino groups. Examples of such groups include aminomethyl, aminoethyl, aminopropyl, aminobutyl and aminohexyl.

The term "alkylaminoalkyl group" encompasses aminoalkyl groups having the nitrogen atom independently substituted with an alkyl group. In certain embodiments, the alkylaminoalkyl groups are "loweralkylaminoalkyl" groups having alkyl groups of one to six carbon atoms. In other embodiments, the lower alkylaminoalkyl groups have alkyl groups of one to three carbon atoms. Suitable alkylaminoalkyl groups may be mono or dialkyl substituted, such as N-methylaminomethyl, N,N-dimethyl-aminoethyl, N,N-diethylaminomethyl and the like.

The term "aralkyl group" encompasses aryl-substituted alkyl groups. In embodiments, the aralkyl groups are "lower aralkyl" groups having aryl groups attached to alkyl groups having one to six carbon atoms. In other embodiments, the lower aralkyl groups phenyl is attached to alkyl portions having one to three carbon atoms. Examples of such groups include benzyl, diphenylmethyl and phenylethyl. The aryl in said aralkyl may be additionally substituted with halo, alkyl, alkoxy, haloalkyl and haloalkoxy.

The term "arylalkenyl group" encompasses aryl-substituted alkenyl groups. In embodiments, the arylalkenyl groups are "lower arylalkenyl" groups having aryl groups attached to alkenyl groups having two to six carbon atoms. Examples of such groups include phenylethenyl. The aryl in said arylalkenyl may be additionally substituted with halo, alkyl, alkoxy, haloalkyl and haloalkoxy.

The term "arylalkynyl group" encompasses aryl-substituted alkynyl groups. In embodiments, arylalkynyl groups are "lower arylalkynyl" groups having aryl groups attached to alkynyl groups having two to six carbon atoms. Examples of such groups include phenylethynyl. The aryl in said aralkyl may be additionally substituted with halo, alkyl, alkoxy, haloalkyl and haloalkoxy. The terms benzyl and phenylmethyl are interchangeable.

The term "alkylthio group" encompasses groups containing a linear or branched alkyl group, of one to ten carbon atoms, attached to a divalent sulfur atom. In certain embodiments, the lower alkylthio groups have one to three carbon atoms. An example of "alkylthio" is methylthio, ($CH_3S$—).

The term "alkylamino group" denotes amino groups which have been substituted with one alkyl group and with two alkyl groups, including terms "N-alkylamino" and "N,N-dialkylamino". In embodiments, alkylamino groups are "lower alkylamino" groups having one or two alkyl groups of one to six carbon atoms, attached to a nitrogen atom. In other embodiments, lower alkylamino groups have one to three carbon atoms. Suitable "alkylamino" groups may be mono or dialkylamino such as N-methylamino, N-ethylamino, N,N-dimethylamino, N,N-diethylamino and the like.

The term "arylamino group" denotes amino groups which have been substituted with one or two aryl groups, such as N-phenylamino. The "arylamino" groups may be further substituted on the aryl ring portion of the group.

The term "heteroarylamino" denotes amino groups which have been substituted with one or two heteroaryl groups, such as N-thienylamino. The "heteroarylamino" groups may be further substituted on the heteroaryl ring portion of the group.

The term "aralkylamino group" denotes amino groups which have been substituted with one or two aralkyl groups. In other embodiments, there are phenyl-$C_1$-$C_3$-alkylamino groups, such as N-benzylamino. The "aralkylamino" groups may be further substituted on the aryl ring portion of the group.

The term "alkylaminoalkylamino group" denotes alkylamino groups which have been substituted with one or two alkylamino groups. In embodiments, there are $C_1$-$C_3$-alkylamino-$C_1$-$C_3$-alkylamino groups.

The term "arylthio group" encompasses aryl groups of six to ten carbon atoms, attached to a divalent sulfur atom. An example of "arylthio" is phenylthio. The term "aralkylthio group" encompasses aralkyl groups as described above, attached to a divalent sulfur atom. In certain embodiments there are phenyl-$C_1$-$C_3$-alkylthio groups. An example of "aralkylthio" is benzylthio.

The term "aryloxy group" encompasses optionally substituted aryl groups, as defined above, attached to an oxygen atom. Examples of such groups include phenoxy.

The term "aralkoxy group" encompasses oxy-containing aralkyl groups attached through an oxygen atom to other groups. In certain embodiments, aralkoxy groups are "lower aralkoxy" groups having optionally substituted phenyl groups attached to lower alkoxy group as described above.

The term "cycloalkyl group" includes saturated carbocyclic groups. In certain embodiments, cycloalkyl groups include $C_3$-$C_6$ rings. In embodiments, there are compounds that include, cyclopentyl, cyclopropyl, and cyclohexyl.

The term "cycloalkenyl group" includes carbocyclic groups that have one or more carbon-carbon double bonds; conjugated or non-conjugated, or a combination thereof. "Cycloalkenyl" and "cycloalkyldienyl" compounds are included in the term "cycloalkenyl". In certain embodiments, cycloalkenyl groups include $C_3$-$C_6$ rings. Examples include cyclopentenyl, cyclopentadienyl, cyclohexenyl and cycloheptadienyl. The "cycloalkenyl" group may have 1 to 3 substituents such as lower alkyl, hydroxyl, halo, haloalkyl, nitro, cyano, alkoxy, lower alkylamino, and the like.

The term "suitable substituent", "substituent" or "substituted" used in conjunction with the groups described herein refers to a chemically and pharmaceutically acceptable group, i.e., a moiety that does not negate the therapeutic activity of the inventive compounds. It is understood that substituents and substitution patterns on the compounds of the invention may be selected by one of ordinary skill in the art to provide compounds that are chemically stable and that can be readily synthesized by techniques known in the art, as well as those methods set forth below. If a substituent is itself substituted with more than one group, it is understood that these multiple groups may be on the same carbon/member atom or on different carbons/member atoms, as long as a stable structure results. Illustrative examples of some suitable substituents include, cycloalkyl, heterocyclyl, hydroxyalkyl, benzyl, carbonyl, halo, haloalkyl, perfluoroalkyl, perfluoroalkoxy, alkyl, alkenyl, alkynyl, hydroxy, oxo, mercapto, alkylthio, alkoxy, aryl or heteroaryl, aryloxy or heteroaryloxy, aralkyl or heteroaralkyl, aralkoxy or heteroaralkoxy, HO—(C=O)—, amido, amino, alkyl- and dialkylamino, cyano, nitro, carbamoyl, alkylcarbonyl, alkoxycarbonyl, alkylaminocarbonyl, dialkylaminocarbonyl, arylcarbonyl, aryloxycarbonyl, alkylsulfonyl, and arylsulfonyl. Typical substituents include aromatic groups, substituted aromatic groups, hydrocarbon groups including alkyl groups such as methyl groups, substituted hydrocarbon groups such as benzyl, and heterogeneous groups including alkoxy groups such as methoxy groups.

The term "fused" means in which two or more carbons/member atoms are common to two adjoining rings, e.g., the rings are "fused rings".

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

The present invention includes pharmaceutically acceptable salts, solvates and prodrugs of the compounds of the invention and mixtures thereof.

The terms "comprising", "having" and "including", and various endings thereof, are meant to be open ended, including the indicated component but not excluding other elements.

The thiosemicarbazone of the invention is represented by a compound of Formula I:

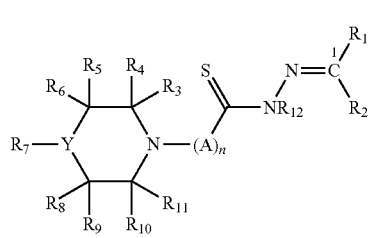

Formula I wherein:

$R_1$ and $R_2$ together form a substituted or unsubstituted polycyclic ring. The ring has at least two ring systems. The two ring systems have a first ring system that is bonded to C1 and a second ring system that is fused to the first ring system.

In one embodiment, the first ring system is a substituted or unsubstituted aromatic group and the second ring system is a substituted or unsubstituted aromatic group, a substituted or unsubstituted heteroaromatic group, a substituted or unsubstituted carbocyclic group, or a substituted or unsubstituted heterocyclic group.

In a second embodiment, the first ring system is a substituted or unsubstituted heteroaromatic group and the second ring system is a substituted or unsubstituted aromatic group, a substituted or unsubstituted heteroaromatic group, a substituted or unsubstituted carbocyclic group, a substituted or unsubstituted heterocyclic group.

In a further embodiment, the first ring system is a substituted or unsubstituted saturated carbocyclic group and the second ring system is a substituted or unsubstituted aromatic group, a substituted or unsubstituted unsaturated carbocyclic group, a substituted or unsubstituted heterocyclic group, or a substituted or unsubstituted ring B:

Ring B wherein $X_1$ to $X_6$ are each independently selected from carbon or a heteroatom.

In another embodiment, the first ring system is a substituted or unsubstituted unsaturated carbocyclic group and the second ring system is a substituted or unsubstituted aromatic group, a substituted or unsubstituted carbocyclic group, a substituted or unsubstituted heterocyclic group, or a substituted or unsubstituted ring B:

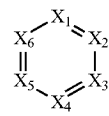

Ring B wherein $X_1$ to $X_6$ are each independently selected from carbon or a heteroatom.

In yet another embodiment, the first ring system is a substituted or unsubstituted heterocyclic group, the second ring system is a substituted or unsubstituted heteroaromatic group, a substituted or unsubstituted carbocyclic group, or a substituted or unsubstituted heterocyclic group.

In another embodiment relating to the above-identified embodiments, the first ring system is a five- or six-membered ring.

In embodiments, the $R_3$ to $R_{11}$ groups are each independently selected from H, a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic. The $R_{12}$ group is selected from H or a hydrocarbyl group and Y is selected from a heteroatom or a carbon atom. "A" is selected from a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic and "n" is an integer.

The thiosemicarbazone described herein can be the compound of Formula I, a pharmaceutically-acceptable salt thereof, a hydrate thereof, a solvate thereof, a tautomer thereof, an optical isomer thereof, or a combination thereof.

In a specific embodiment, the first ring system of the compound of Formula I is a substituted or unsubstituted carbocyclic group and the second ring system is a substituted or unsubstituted ring B:

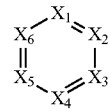

Ring B wherein $X_1$ to $X_6$ are each independently selected from carbon or a heteroatom. In a more specific embodiment, ring B is a pyridine ring, typically fused to the first ring at C2 and C3 of the pyridine ring.

Although a first and second ring system is described herein, the substituted or unsubstituted polycyclic ring may further comprise other ring systems other than the first and second ring systems. For example, a third ring system may also be fused to the first ring system. The third ring system can be, for instance, a substituted or unsubstituted aromatic group, a substituted or unsubstituted heteroaromatic group, a substituted or unsubstituted carbocyclic group, or a substituted or unsubstituted heterocyclic group. Typically, the third ring system is a substituted or unsubstituted heteroaromatic group or a substituted or unsubstituted heterocyclic group.

With respect to the embodiments described above with respect to Formula I, typically "n" is 0 or 1. If "n" is 1, "A" is typically a substituted or unsubstituted heteroaromatic group, in particular, a pyridinyl group.

Also, with respect to the embodiments of Formula I, Y is typically a nitrogen atom. The ring:

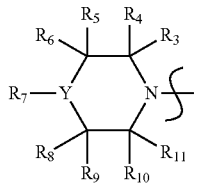

can be a variety of rings. The ring can be a substituted or unsubstituted thiomorpholinyl group, a substituted or unsubstituted morpholinyl group, a substituted or unsubstituted piperidinyl group, or a substituted or unsubstituted piperazinyl group.

In specific embodiments of Formula I, $R_7$ is a substituted or unsubstituted alkyl group or a substituted or unsubstituted heteroaromatic group and $R_3$ to $R_6$ and $R_8$ to $R_{12}$ are each independently selected from H or a substituted or unsubstituted hydrocarbon group. More specifically, $R_7$ can be the substituted or unsubstituted alkyl group or a substituted or unsubstituted pyridyl group and $R_3$ to $R_6$ and $R_8$ to $R_{12}$ are each H.

In specific embodiments, the compound of Formula I can be:

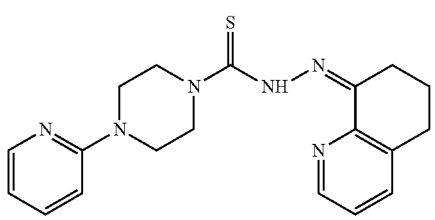

COTI-2

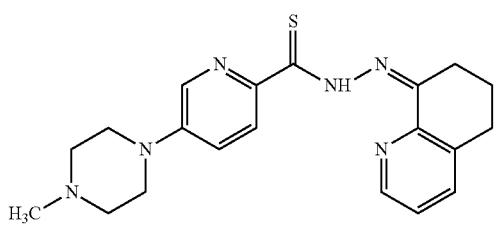

COTI-5

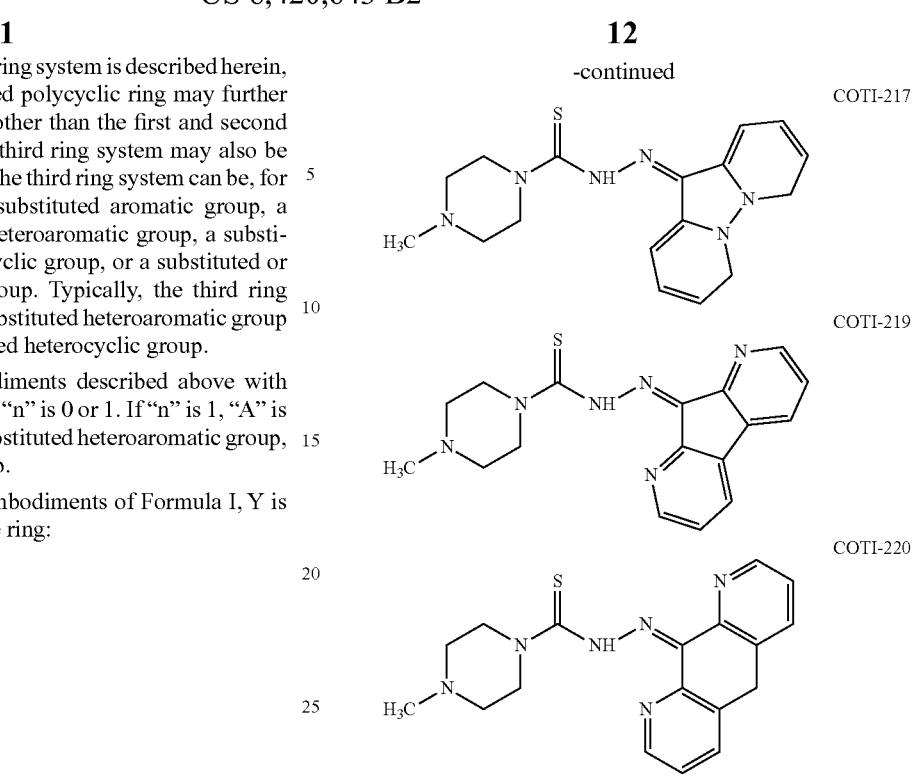

COTI-217

COTI-219

COTI-220

Such compounds may be used and/or in the form of a pharmaceutically-acceptable salt, hydrate, solvate or any combination thereof.

The compounds of Formula I described herein can be prepared as follows:

a) reacting a compound of Formula II:

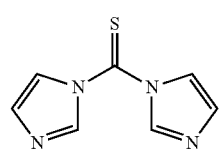

Formula II with a compound of Formula IIA:

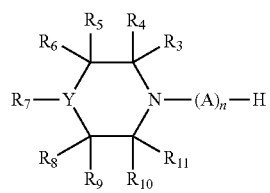

Formula IIA to form an intermediate of Formula III:

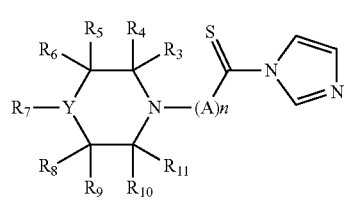

Formula III b) reacting the Intermediate of Formula III with $R_{12}NHNH_2$ to form an Intermediate of Formula IV:

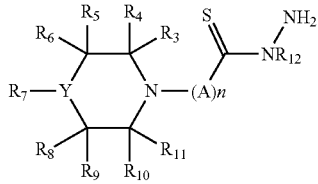

Formula IV c) reacting the Intermediate of Formula IV with a ketone:

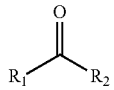

under condensation conditions, to form the compound of Formula I. In specific embodiments, the above-identified synthetic method can be used when "n" is 0 or 1; more typically, when "n" is 0.

The compounds of Formula I described herein can also be prepared as follows:

a) dithioesterifying a halo compound of Formula V:

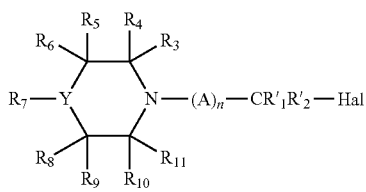

Formula V to form an intermediate of Formula VI, wherein R, $R'_1$ or $R'_2$ is substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic:

Formula VI

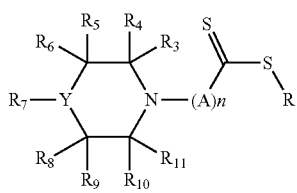

b) reacting the Intermediate of Formula VI with $R_{12}NHNH_2$ to form an Intermediate of Formula IV:

Formula IV

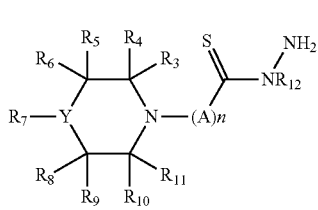

c) reacting the Intermediate of Formula IV with a ketone:

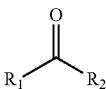

under condensation conditions, to form the compound of Formula I. In specific embodiments, the above-identified synthetic method can be used when "n" is 0 or 1; more typically, when "n" is 1.

The compounds of Formula I described herein can also be prepared as follows:

a) esterifying compound of Formula IIA:

Formula IIA

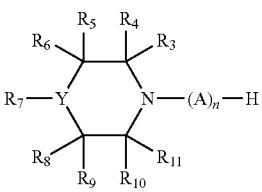

to form an intermediate of Formula VII, wherein R is substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic:

Formula VII

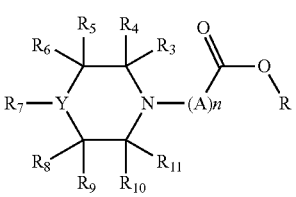

b) reacting the Intermediate of Formula VII with $R_{12}NHNH_2$ to form an Intermediate of Formula VIII:

Formula VIII

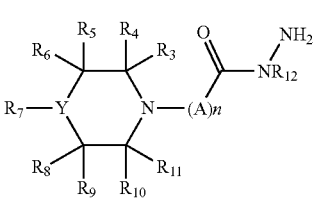

c) reacting the Intermediate of Formula VIII with a thiation agent to form an Intermediate of Formula IV:

Formula IV

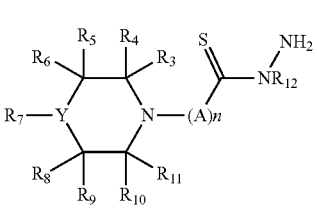

c) reacting the Intermediate of Formula IV with a ketone:

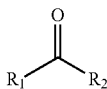

under condensation conditions, to form the compound of Formula I. Examples of a thiation agent include, but are not limited to, phosphorus pentasulfide or Lawesson's reagent. In specific embodiments, the above-identified synthetic method can be used when "n" is 0 or 1; more typically, when "n" is 1.

The compounds of the present invention are useful in the treatment of cancer. High levels of activity for in vitro and in vivo testing have been observed against cancers and cancer models using the compounds of the present invention. This may lead to reduced dosages as compared with conventional therapeutic dosages of known agents.

The cancer treated may be, for example, lung cancer, cervical cancer, ovarian cancer, cancer of CNS, skin cancer, prostate cancer, sarcoma, breast cancer, leukemia, colorectal cancer, head cancer, neck cancer or kidney cancer. More typically, the cancer may be small cell lung cancer, breast cancer, acute leukemia, chronic leukemia, colorectal cancer, or brain cancer. The cancer may be a carcinoma. The carcinoma may be selected from small cell carcinomas, cervical carcinomas, glioma, astrocytoma, prostate carcinomas, ovarian carcinomas, melanoma, breast carcinomas, or colorectal carcinomas. Compounds of the present invention may be even more particularly useful in the treatment of small cell lung cancer (SCLC) carcinomas.

Compounds of the present invention can have an $IC_{50}$ for a cancer cell population of less than about 1000 nM. In specific embodiments, compounds of the present invention show efficacy against SHP77 cells at IC50's of less than about 1000 nM, typically less than about 800 nM, more typically less than about 500 nM, even more typically less than about 200 nM.

Compounds of the present invention show efficacy against DMS144 cells at IC50's of less than about 1000 nM, typically less than about 750 nM, more typically less than about 500 nM, even more typically less than about 300 nM, yet more typically less than about 100 nM.

Compounds of the present invention show efficacy against U87 cells at IC50's of less than about 2500 nM, typically less than about 1000 nM, more typically less than about 480 nM, even more typically less than about 200 nM, yet more typically less than about 75 nM.

Compounds of the present invention show efficacy against SNB-19 cells at IC50's of less than about 2150 nM, typically less than about 1500 nM, more typically less than about 800 nM, even more typically less than about 100 nM, yet more typically less than about 50 nM, still more typically less than about 15 nM.

Compounds of the present invention are effective in reducing the size of malignant human cancer tumors created from SHP77, DMS114, N417 and/or U87 cell lines.

Compounds of the present invention can penetrate the blood brain barrier of a mammal, typically, a human.

Compounds of the present invention may exhibit a reduced tendency to induce cellular resistance to their own anti-cancer effects. Therefore, use of the compounds of the present invention to treat a cancer may inhibit development of a drug resistant form of that cancer. Without wishing to be limited by theory, it is believed that the compounds of the present invention may inhibit development of P-glycoprotein mediated drug resistance.

Certain compounds of the present invention may exhibit reduced toxicity as compared with conventionally administered agents.

The compounds of this invention may be administered to mammals, typically humans, either alone or, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, and subcutaneous routes of administration.

As noted, compounds of the present invention may be administered orally unlike most current cancer therapies, which are administered intravenously. For oral use of a compound or composition according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

At least about 50% of the compound of the present invention can be orally absorbed by a mammal. In specific embodiments, at least about 60%; about 60% to about 85%; about 65%; about 70%; about 72%; about 73%, about 75%; about 80%; about 82%; or about 85% of the compound of the present invention can be orally absorbed by a mammal, more typically, a human. "Oral absorption" is used in the context of how the compound/composition of the present invention are delivered and absorbed into the blood. Typically, the compound/composition is administered orally and crosses a mucosal membrane of the gastro-intestinal tract, typically in the intestines. However, other methods of contacting the compounds/compositions of the present invention with the mucosal membrane of the gastro-intestinal tract may also be used.

The compounds of the present invention may also be combined and/or co-administered with other therapeutic agents that are selected for their particular usefulness against the cancer that is being treated. For example, the compounds of the present invention may be combined and/or co-administered with anti-cancer agent(s).

Examples of anti-cancer agents include, without being limited thereto, the following: estrogen receptor modulators, androgen receptor modulators, retinoid receptor modulators, cytotoxic agents, antiproliferative agents, tyrosine kinase inhibitors, prenyl-protein transferase inhibitors, HMG-CoA reductase inhibitors, HIV protease inhibitors, reverse transcriptase inhibitors, other angiogenesis inhibitors and combinations thereof. The present compounds may also be useful with other therapies such as when co-administered with radiation therapy.

"Estrogen receptor modulators" refers to compounds which interfere or inhibit the binding of estrogen to the receptor, regardless of mechanism. Examples of estrogen receptor modulators include, but are not limited thereto, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide and N-4-carboxyphenyl retinamide.

"Cytotoxic agents" refer to compounds which cause cell death primarily by interfering directly with the cell's functioning or inhibit or interfere with cell myosis, including alkylating agents, tumor necrosis factors, intercalators, microtubulin inhibitors, and topoisomerase inhibitors.

Examples of cytotoxic agents include, but are not limited thereto, cyclophosphamide ifosfamide, hexamethylmelamine, tirapazimine, sertenef, cachectin, ifosfamide, tasonermin, lonidamine, carboplatin, mitomycin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine) platinum, benzylguanine, glufosfamide, GPX100, (trans, trans, trans)-bis-mu-(hexane-1,6-diamine)-mu-[diamine-platinum(II)]bis[diamine (chloro)-platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-1-13-deoxo-10-hydroxycaminomycin, annamycin, galarubicin, elinafide, MEN10755, and 4-demethoxy-3-deamino-3-aziridinyl-4-methylsulphonyl-daunor-ubicin (see International Patent Application No. WO 00/50032).

Examples of microtubulin inhibitors include paclitaxel (Taxol®), vindesine sulfate, 3',4'-didehydro-4'-deoxy-8'-norvincaleukoblastine, docetaxel, rhizoxin, dolastatin, mivobulin isethionate, auristatin, cemadotin, RPR109881, BMS184476, vinflunine, cryptophycin, 2,3,4,5,6-pentafluoro-N-(-3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-1-2-(6H)propanamine, 1-amino-9-ethyl-5-fluoro-2,3-dihydro-9-hydroxy-4-methyl-1H,12H benzo[de]pyrano[3',4':b,7]indolizino[1,2b]quinoline-10,13(9H,15H) dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazo-le-1-carboxamide, asulacrine, (5a, 5aB,8aa,9b)-9-[2-[N-[2-(dimethylamino)-ethyl]-N-methylamino]ethyl]-5-[4-Hydroxy-3,5-dimethoxyphenyl]-5,5a,6,8,8a,-9-hexohydrofuro(3',4':6,7)naphtho(2,3-d)-1,3-dioxol-6-one, 2,3-(methylenedioxy)-5-methyl-7-hydroxy-8-methoxybenzo[c]-phenanthridiniu-m, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-py-razolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl) acrid-ine-4-carboxamide, 6-[[2-(dimethylamino)ethyl] amino]-3-hydroxy-7H-indeno[2-,1-c]quinolin-7-one, and dimesna.

"Antiproliferative agents" includes BCNU, antisense RNA and DNA oligonucleotides such as G3139, ODN698, RVASKRAS, GEM231, and INX3001, and antimetabolites such as floxuridine, enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxy-cytidine, N-[5-(2,3-dihydro-benzofuryl)sulfonyl]-N'-(3,4-dichlorophenyl)urea, N6-[4-deoxy-4-[N2-[2(E),4(E)-tetradecadienoyl]glycylamino]-L-glycer-o-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,1'-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, and 3-aminopyridine-2-carboxaldehyde thiosemicarbazone.

"Antiproliferative agents" also includes monoclonal antibodies to growth factors, other than those listed under "angiogenesis inhibitors", such as trastuzumab, and tumor suppressor genes, such as p53, which can be delivered via recombinant virus-mediated gene transfer (see U.S. Pat. No. 6,069,134, for example).

Some specific examples of tyrosine kinase inhibitors include N-(trifluoromethylphenyl)-5-methylisoxazol-4-carboxamide, 3-[(2,4-dimethylpyrrol-5-yl)methylidenyl]indolin-2-one, 17-(allylamino)-17-demethoxygeldanamycin, 4-(3-chloro-4-fluorophenylamino-)-7-methoxy-6-[3-(4-morpholinyl)propoxyl]-quinazoline, N-(3-ethynylphenyl)-6, 7-bis(2-methoxyethoxy)-4-quinazolinamine, 2,3,9,10,11, 12-hexahydro-10-(hydroxymethyl)-10-hydroxy-9-methyl-9, 12-epoxy-1H-diindolo[1,2,3-fg:3',2',1'-kl]pyrrolo[3,4-i][1, 6]benzodiazocin-1-one, SH1382, genistein, 4-(3-chlorophenylamino)-5,6-dimethyl-7H-pyrrolo[2,3-d] pyrimidinemethane sulfonate, 4-(3-bromo-4-hydroxyphenyl)-amino-6,7-dimethoxyquinazoline, 4-(4'-hydroxyphenyl)amino-6,7-dimethoxyquinazoline, N-4-chlorophenyl-4-(4-pyridylmethyl)-1-phthalazinamine, and Tarceva® (erlotinib).

If formulated as a fixed dose, such combination products employ the compounds of this invention within the dosage range described below and the other pharmaceutically active agent(s) within its approved dosage range. Compounds of the present invention may alternatively be used sequentially with known pharmaceutically acceptable agent(s) when a combination formulation is inappropriate.

The term "administration" (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount from about 0.01 mg/kg of body weight to greater than about 100 mg/kg of body weight per day; from about 0.01 mg/kg of body weight to about 500 mg/kg of body weight per day; from about 0.01 mg/kg of body weight to about 250 mg/kg of body weight per day; or 0.01 mg/kg of body weight to about 100 mg/kg of body weight per day. These dosages can be more particularly used orally.

The compounds of this invention may be prepared by employing reactions and standard manipulations that are known in the literature or exemplified herein.

When introducing elements disclosed herein, the articles "a", "an", "the", and "said" are intended to mean that there are one or more of the elements.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Synthesis of COTI-2

The synthesis of COTI-2, as depicted above, was conducted according to the following synthetic methodology:

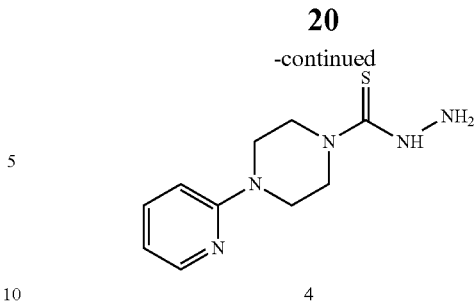

Imidazol-1-yl-(4-pyridin-2-yl-piperazin-1-yl)-methanethione (or intermediate 3 above) was formed as follows. N-(2-pyridyl)piperazine (MW 163.22, 0.91 ml, 6.0 mmoles, 1 eq) 2 was added to a solution of 1,1'-thiocarbonyldiimidazole (MW 178.22, 1.069 g, 6.0 mmoles, 1 eq) 1 in 50 ml of dichloromethane at room temperature. The reaction mixture was stirred overnight at room temperature. The mixture was washed with water, dried over sodium sulfate, filtered and concentrated to provide imidazol-1-yl-(4-pyridin-2-yl-piperazin-1-yl)-methanethione (MW 273.36, 1.354 g, 4.95 mmol, 83% yield) 3, which was used without further purification. TLC ($CH_2Cl_2$/MeOH: 95/5): Rf=0.60, Product UV and Ninhydrin stain active. $^1$H-NMR (400 MHz, $CDCl_3$), δ ppm: 3.72 (s, 4H), 4.02 (s, 4H), 6.67 (d, 1H, J=7 Hz), 6.72 (dd, 1H, J=7 and 5 Hz), 7.11 (s, 1H), 7.24 (s, 1H), 7.54 (t, 1H, J=7 Hz), 7.91 (s, 1H), 8.20 (d, 1H, J=5 Hz).

Hydrazine hydrate (MW 50.06, 0.26 ml, 5.44 mmoles, 1.1 eq) was added to a solution of imidazol-1-yl-(4-pyridin-2-yl-piperazin-1-yl)-methanethione 3 (MW 210.30, 1.040 g, 4.95 mmol, 1 eq) in 30 ml of ethanol at room temperature. The reaction mixture was stirred under reflux for 2 hours. A white precipitate formed. This white solid was filtered off and rinsed with diethyl ether to yield 1-[N-(2-pyridyl)-piperazine)-carbothioic acid hydrazide (MW 237.33, 0.86 g, 3.62 mmol, 73% yield) 4 as a white solid, and used without further purification. TLC ($CH_2Cl_2$/MeOH: 95/5): Rf=0.20, Product UV and Ninhydrin stain active. $^1$H-NMR (400 MHz, DMSO-$d_6$), δ ppm: 3.53 (s, 4H), 3.85 (s, 4H), 6.66 (dd, 1H, J=8 and 5 Hz), 6.82 (d, 1H, J=8 Hz), 7.55 (t, 1H, J=8 Hz), 8.12 (d, 1H, J=5 Hz).

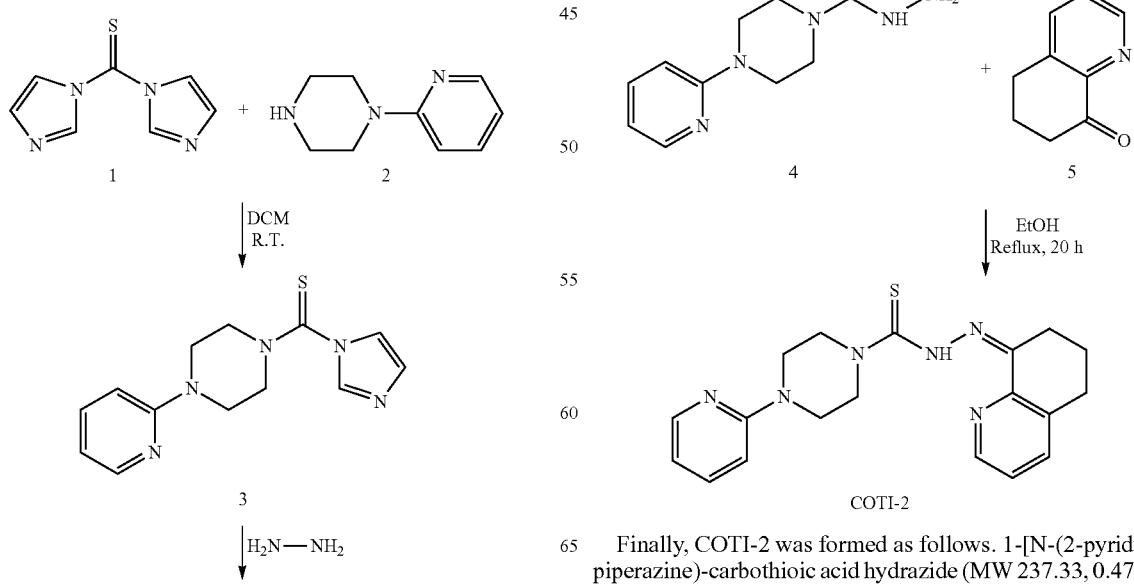

Finally, COTI-2 was formed as follows. 1-[N-(2-pyridyl)-piperazine)-carbothioic acid hydrazide (MW 237.33, 0.475 g, 2.0 mmol, 1 eq) 4 and 6,7-dihydro-5H-quinolin-8-one (MW 147.18, 0.306 g, 2.0 mmol, 1 eq) 5 was dissolved in 15 ml of ethanol at room temperature. The mixture was then stirred under reflux for 20 hours. A yellow solid precipitated out of the solution. This solid was filtered off then rinsed with methanol and diethyl ether to yield COTI-2 (MW 366.48, 0.60 g, 1.64 mmol, 82% yield) as a yellow solid. TLC (CH$_2$Cl$_2$/MeOH: 95/5): Rf=0.75, Product UV and Ninhydrine stain active. HPLC analysis showed a mixture of isomers (approximately in 80/20 ratio), and >98% purity. During the HPLC Method Development, as expected, this product tends to be hydrolyzed in presence of TFA in mobile phase solution. MS (ESI+, 0.025% TFA in 50/50 MeOH/H$_2$O): [M+H]$^+$=367.1, [M+Na]$^+$=389.1; $^1$H-NMR (400 MHz, CDCl$_3$), δ ppm (Major isomer): 2.09 (m, 2H), 2.92 (m, 4H), 3.67 (m, 4H), 4.27 (m, 4H), 6.69 (dd, 1H, J=8 and 5 Hz), 7.25 (dd, 1H, J=8 and 5 Hz), 7.55 (d, 2H, J=8 Hz), 8.23 (d, 1H, J=5 Hz), 8.63 (d, 1H, J=5 Hz), 14.76 (s, 1H). δ ppm (Minor isomer): 2.09 (m, 2H), 3.14 (t, 4H, J=6 Hz), 3.80 (m, 4H), 4.27 (m, 4H), 6.66 (m, 1H), 7.31 (dd, 1H, J=8 and 5 Hz), 7.52 (m, 1H), 7.70 (d, 1H, J=8 Hz), 8.23 (d, 1H, J=5 Hz), 8.53 (d, 1H, J=5 Hz), 15.65 (s, 1H).

Synthesis of COTI-219

The synthesis of COTI-219, as depicted above, was conducted according to the following synthetic methodology:

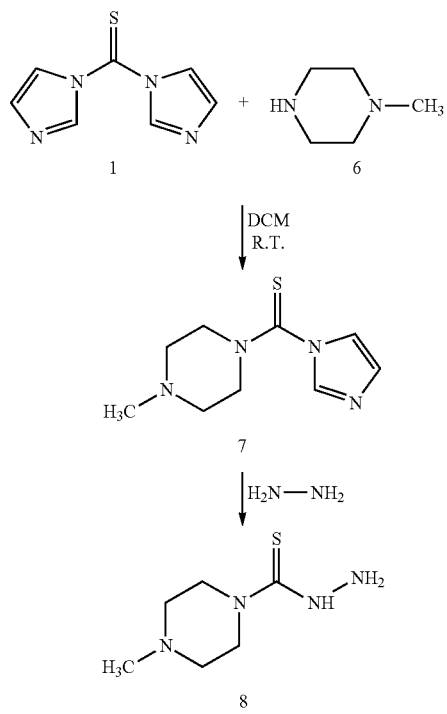

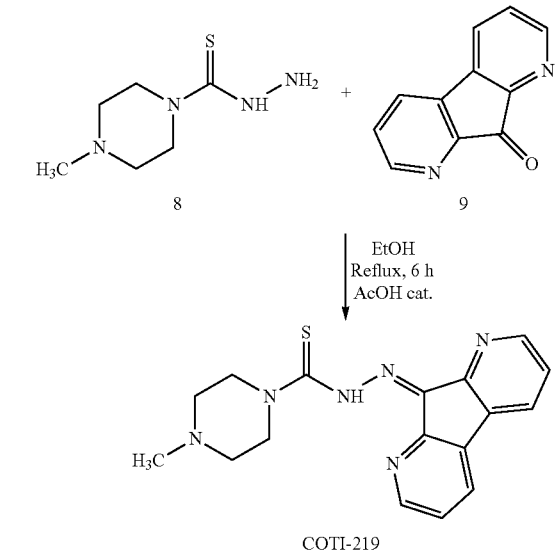

Imidazol-1-yl-(4-methyl-piperazin-1-yl)-methanethione (or intermediate 7 above) was formed as follows. N-Methyl piperazine (MW 100.16, 0.67 ml, 6.0 mmol, 1 eq) 6 was added to a solution of 1,1'-thiocarbonyldiimidazole (MW 178.22, 1.069 g, 6.0 mmol, 1 eq) 1 in 50 ml of dichloromethane at room temperature. The reaction mixture was stirred overnight at room temperature. This mixture was washed with water, dried over sodium sulfate, filtered and concentrated to provide imidazol-1-yl-(4-methyl-piperazin-1-yl)-methanethione (MW 210.30, 1.040 g, 4.95 mmol, 82% yield) 7 and used without further purification. TLC (CH$_2$Cl$_2$/MeOH: 95/5): Rf=0.35, Product UV and Ninhydrine stain active. $^1$H-NMR (400 MHz, CDCl$_3$), δ ppm: 2.37 (s, 3H), 2.56 (s, 4H), 3.94 (s, 4H), 7.11 (s, 1H), 7.21 (s, 1H), 7.88 (s, 1H).

1-(N-Methyl piperazine)-carbothioic acid hydrazide (or intermediate 8 above) was formed as follows. Hydrazine hydrate (MW 50.06, 0.26 ml, 5.44 mmol, 1.1 eq) was added to a solution of imidazol-1-yl-(4-methyl-piperazin-1-yl)-methanethione 7 (MW 210.30, 1.040 g, 4.95 mmol, 1 eq) in 30 ml of ethanol at room temperature. The reaction mixture was stirred under reflux for 2 hours. This mixture was concentrated. The solid thus obtained was triturated with diethyl ether and filtered to yield 1-(N-Methyl piperazine)-carbothioic acid hydrazide (MW 174.27, 0.53 g, 3.04 mmol, 61% yield) 8 as a white solid which was used without further purification. TLC (CH$_2$Cl$_2$/MeOH: 90/10): Rf=0.15, Product UV and Ninhydrin stain active. $^1$H-NMR (400 MHz, DMSO-d$_6$), δ ppm: 2.17 (s, 3H), 2.28 (t, 4H, J=5 Hz), 3.69 (t, 4H, J=5 Hz).

Finally, COTI-219 was made as follows. 1-(N-Methyl piperazine)-carbothioic acid hydrazide (MW 174.27, 0.174 g, 1.0 mmol, 1 eq) 8 and 1,8-diazafluoren-9-one (MW 182.18, 0.182 g, 1.0 mmol, 1 eq) 9 was dissolved in 15 ml of ethanol at room temperature, in the presence of 1% glacial acetic acid (MW 60.05, 0.15 ml, 2.6 mmol, 2.6 eq). The mixture was stirred under reflux for 6 hours. After concentration, the crude thus obtained was taken up in dichloromethane, washed with a potassium carbonate aqueous solution then with water. The organic layer was dried over sodium sulfate, filtered and concentrated. The crude was purified by ISCO CombiFlash™ Companion (Redisep™ cartridge 12 g, Normal phase, Gradient DCM/MeOH: 10/0 to 9/1) and provided COTI-219 (MW 338.43, 0.330 g, 0.975 mmol, 98% yield) as a rust red solid. >95% purity by $^1$H-NMR. MS [ESI+, 90/10 MeOH/H$_2$O (5 mM NH$_4$OAc, 0.2% Acetic acid)]: [M+H]$^+$=339.1, [M+Na]$^+$=361.1; $^1$H-NMR (400 MHz, CDCl$_3$), δ ppm: 2.31 (s, 3H), 2.56 (t, 4H, J=5 Hz), 4.17 (t, 4H, J=5 Hz), 7.23 (dd, 1H, J=8 and 5 Hz), 7.31 (dd, 1H, J=8 and 5 Hz), 7.86 (d, 1H, J=8 Hz), 7.97 (d, 1H, J=8 Hz), 8.47 (d, 1H, J=5 Hz), 8.51 (d, 1H, J=5 Hz), 13.53 (s, 1H).

Synthesis of COTI-5

The synthesis of COTI-5, as depicted above, is conducted according to the following synthetic methodology:

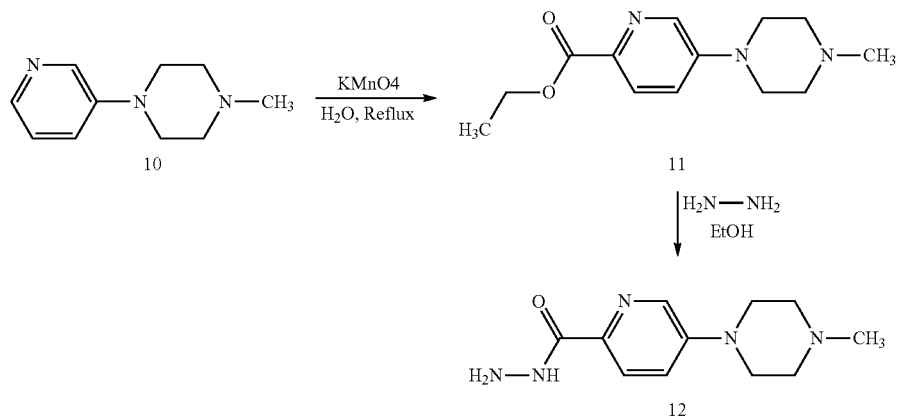

Intermediate 11 is formed by reacting compound 10 with potassium, permanganate under reflux conditions. Intermediate 11 is reacted with hydrazine hydrate in ethanol to form intermediate 12.

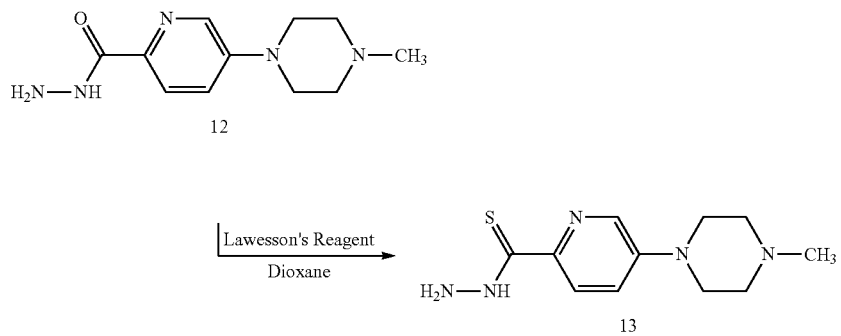

Intermediate 12 is reacted with Lawesson's reagent in dioxane to form intermediate 13.

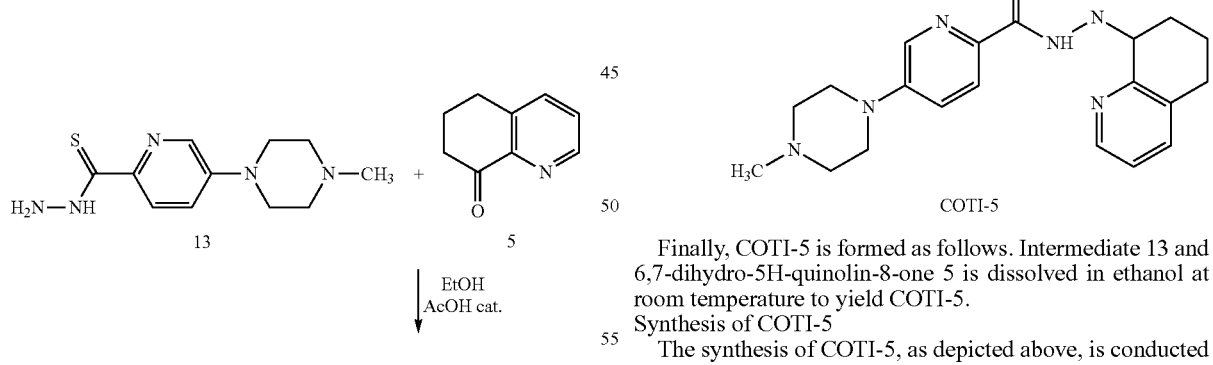

Finally, COTI-5 is formed as follows. Intermediate 13 and 6,7-dihydro-5H-quinolin-8-one 5 is dissolved in ethanol at room temperature to yield COTI-5.

Synthesis of COTI-5

The synthesis of COTI-5, as depicted above, is conducted according to the following synthetic methodology:

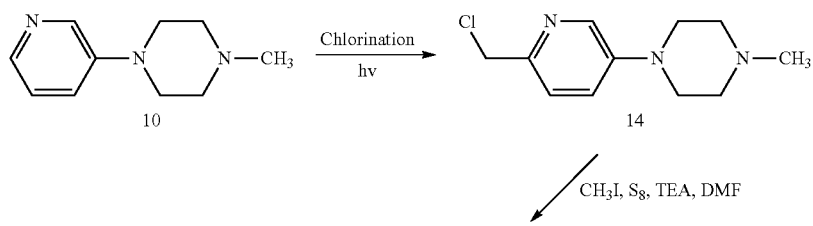

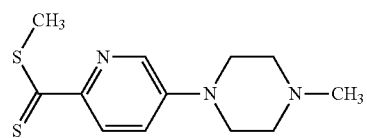

15

H₂N—NH₂
EtOH

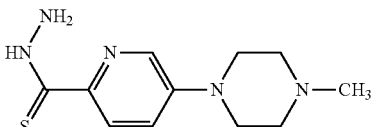

13

Intermediate 14 is formed by irradiating compound 10 in the presence of chlorine (the corresponding bromo compound of intermediate 14 can be formed using N-bromosuccinimide, benzyl peroxide in benzene). Intermediate 14 is reacted with S$_8$ and methyl iodide in TEA and DMF (PhSO$_2$Na, acetonitrile, Pr$_4$NBr at 80° C. for 24 h or S$_8$, t-BuOK at R.T., THF then methyl iodide may also be used) to yield intermediate 15. Intermediate 15 is reacted with hydrazine hydrate in ethanol to form intermediate 13.

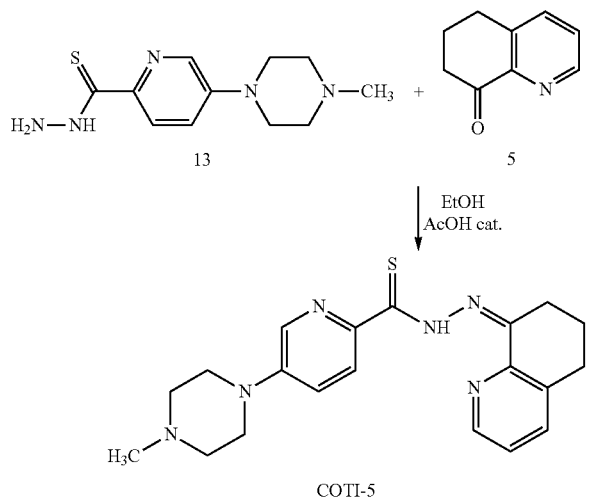

Finally, COTI-5 is formed as follows. Intermediate 13 and 6,7-dihydro-5H-quinolin-8-one 5 is dissolved in ethanol at room temperature to yield COTI-5.

Example 1

In-Silico Assessment of Properties

An in-silico assessment of the properties of compounds according to the present invention was performed using the CHEMSAS® computational platform. CHEMSAS® is a robust proprietary computational platform for accelerated drug discovery, optimization and lead selection based upon a unique combination of traditional and modern pharmacology principles, statistical modeling and machine learning technologies. At the centre of the CHEMSAS® platform is a hybrid machine learning technology that may be used to: find, profile and optimize new targeted lead compounds; find novel uses for known compounds; and, solve problems with existing or potential drugs. In using the CHEMSAS®platform, first a therapeutic target was selected, in this case cancer and more particularly Small Cell Lung Cancer. The second step involved the design of a candidate molecule library containing thousands of potential compounds through the assembly of privileged molecular fragments. Thirdly, the candidate library was profiled and optimized using a combination of validated computational models and traditional expert medicinal chemistry. In this step, the CHEMSAS® platform developed 244 molecular descriptors for each candidate therapeutic compound. For example, molecular properties relating to a candidate compound's therapeutic efficacy, expected human toxicity, oral absorption, cumulative cellular resistance and/or kinetics were assessed. In some instances, comparative properties relating to commercially relevant benchmark compounds were also assessed. Potential lead compounds were then selected from the candidate library using a proprietary decision making tool designed to identify candidates with the optimal physical chemical properties, efficacy, ADME/Toxicity profile, etc. according to a pre-determined set of design criteria. The lead compounds selected from the candidate library were then synthesized for further pre-clinical development.

The properties of certain compounds according to the present invention, specifically COTI-217, COTI-220, COTI-219, COTI-2 and COTI-5, that were assessed in-silico using the CHEMSAS® computational platform are shown in Tables 1 to 13. Some of the predicted properties are validated by the experimental data provided herein, while other properties have been validated elsewhere during the development of other clinical candidates. The CHEMSAS® platform therefore provides a means of determining, predicting and/or testing the properties of a compound, particularly when used to determine the properties of compounds according to the present invention. The CHEMSAS® platform is also particularly useful in comparing the properties of compounds according to the invention with prior art compounds on a relative basis in silico.

Tables 1A and 1B: Physical Chemical Properties

Tables 1A and 1B shows that COTI-217, COTI-220, COTI-219, COTI-2 and COTI-5 are "drug-like" with good drug like physical properties.

TABLE 1A

| MolID | FORMULA | MolWeight | MnLogP | HBndDon | HBndAcc |
|---|---|---|---|---|---|
| COTI217 | C17H22N6S | 342.469 | 1.859199 | 1 | 6 |
| COTI220 | C18H20N6S | 352.464 | 2.078432 | 1 | 6 |
| COTI219 | C17H18N6S | 338.437 | 1.7646 | 1 | 6 |
| COTI2 | C19H22N6S | 366.491 | 3.041311 | 1 | 6 |
| COTI5 | C20H24N6S | 380.518 | 2.22023 | 1 | 6 |

TABLE 1B

| MolID | TPSA | RotBnds | LipinskiAlerts | Veber |
|---|---|---|---|---|
| COTI217 | 37.5435 | 3 | 0 | 0 |
| COTI220 | 53.3605 | 3 | 0 | 0 |
| COTI219 | 53.3605 | 3 | 0 | 0 |
| COTI2 | 53.3605 | 4 | 0 | 0 |
| COTI5 | 53.3605 | 4 | 0 | 0 |

Legend for Table 1:

MolWeight stands for Molecular Weight measured in Daltons and is a size descriptor;

MnLogP is an average of MLogP, ALogP98 and CLogP, all of which are calculated lipophilicity/solubility estimates;

HBndDon stands for Hydrogen Bond Donor and refers to the number of atoms able to donate electrons to potentially form Hydrogen bonds;

HBndAcc stands for Hydrogen Bond Acceptor and refers to the number of atoms able to accept electrons to potentially form Hydrogen bonds;

TPSA stands for Topological Polar Surface Area and is a measure of Molecular Surface Charge/Polarity;

RotBnds stands for Rotatable Bonds which is a count of freely rotatable single bonds in the molecule;

LipinskiAlerts If any 2 of (Molecular weight>500 Daltons, Hydrogen Bond Donors>5, Hydrogen Bond Acceptors>10, MLogP>4.15) are true, then a molecule is likely to have poor bioavailability;

Veber Alerts: If TPSA>140 or number of Rotatable Bonds is >10, then bioavailability is likely to be poor.

Tables 2A and 2B: Solubility Properties

Tables 2A and 2B shows that COTI-217, COTI-220, COTI-219, COTI-2 and COTI-5 are expected to have acceptable solubility values for drug-like compounds.

TABLE 2A

| MolID | FORMULA | MnLogP | LogD (pH 7) | LogS |
|---|---|---|---|---|
| COTI217 | C17H22N6S | 1.859199 | 0.309304 | −3.09009 |
| COTI220 | C18H20N6S | 2.078432 | 0.992417 | −4.20136 |
| COTI219 | C17H18N6S | 1.7646 | 1.067558 | −3.78407 |
| COTI2 | C19H22N6S | 3.041311 | 2.380243 | −4.52904 |
| COTI5 | C20H24N6S | 2.22023 | 1.019701 | −4.49499 |

TABLE 2B

| MolID | FORMULA | Acid pKa 2 | Base pKa 1 | Base pKa 2 |
|---|---|---|---|---|
| COTI217 | C17H22N6S | None | 7.65056 | None |
| COTI220 | C18H20N6S | None | 7.65056 | 4.71559 |
| COTI219 | C17H18N6S | None | 7.65056 | 3.90139 |
| COTI2 | C19H22N6S | None | 5.65356 | 4.882592 |
| COTI5 | C20H24N6S | None | 7.870707 | 5.617688 |

Legend for Table 2:

MnLogP is an average of MLogP, ALogP98 and CLogP, all of which are calculated lipophilicity/solubility estimates;

LogD (7.4) is a measure of relative solubility in octanol vs water at a specific pH, in this case pH=7.4;

LogS is the logarithm of the calculated solubility in pure water usually measured at 25 degrees centigrade;

pKa is a calculated estimate of the pH at which the drug or substructures of the drug is 50% ionized and 50% is unionized.

Table 3: Efficacy (LogGI50)

Table 3 shows that COTI-217, COTI-220, COTI-219, COTI-2 and COTI-5 are predicted to have sub-micromolar in vitro activity vs human SCLC cell lines. Actual measurements obtained in vitro confirm the prediction of activity at sub-micromolar levels for COTI-2 and COTI-219.

| MolID | FORMULA | DMS114 | SHP-77 | Predicted | Actual |
|---|---|---|---|---|---|
| COTI217 | C17H22N6S | <−6 | <−6 | Active | ND |
| COTI220 | C18H20N6S | <−6 | <−6 | Active | ND |
| COTI219 | C17H18N6S | <−6 | <−6 | Active | Active |
| COTI2 | C19H22N6S | <−6 | <−6 | Active | Active |
| COTI5 | C20H24N6S | <−6 | <−6 | Active | ND |

Legend for Table 3:

DMS114 is a "classical" human small cell lung cancer line that is maintained by the National Cancer Institute in the United States;

SHP-77 is a "variant" human small cell lung cancer line that is maintained by the National Cancer Institute in the United States;

Predicted is the predicted in vitro Activity of the drug;

Actual is the actual outcome of in vitro testing in both of the reference human small cell lung cancer lines;

"Active" refers to drugs with predicted or measured GI50<1 µmol/L;

ND means that the drug has not yet been tested in vitro.

Tables 4A and 4B: Oral Absorption and BBB Penetration

Tables 4A and 4B shows that COTI-217, COTI-220, COTI-219, COTI-2 and COTI-5 are expected to be absorbed orally.

TABLE 4A

| MolID | FORMULA | Mn % OrlAbs | Mn % Abs | HIA-T2(MD) |
|---|---|---|---|---|
| COTI217 | C17H22N6S | 82.67412 | 67.67412 | 2.16777 |
| COTI220 | C18H20N6S | 88.79283 | 73.79283 | 0.144973 |
| COTI219 | C17H18N6S | 85.52785 | 70.52785 | 0.314455 |
| COTI2 | C19H22N6S | 87.02755 | 72.02755 | 0.38029 |
| COTI5 | C20H24N6S | 88.43881 | 73.43881 | 0.277855 |

TABLE 4B

| MolID | ProbBBB Pene | LogBBB | BBB-T2 (MD) | Clark LogBBB | SubKit LogBB |
|---|---|---|---|---|---|
| COTI217 | 0.918625 | −0.32584 | 2.280528 | −0.09599 | −0.22923 |
| COTI220 | 0.26949 | −0.24921 | 0.254967 | −0.36111 | −0.20053 |
| COTI219 | 0.331 | −0.39022 | 0.551314 | −0.39876 | −0.31048 |
| COTI2 | 0.710661 | −0.01576 | 0.416152 | −0.19558 | −0.0185 |
| COTI5 | 0.089884 | −0.0646 | 0.315208 | −0.37444 | −0.05658 |

Legend for Table 4:

Mn % OrlAbs is the prediction of the mean percent oral absorption of the drug from an ensemble of 5-7 different models;

Min % Abs is the minimum value for the Mn % OrlAbs at the lower 95% Confidence Interval;

HIA-T2(MD) is the Malanabois distance, which is a measure of the calculated statistical distance from the centre of a population of drugs with optimal oral absorption;

ProbBBBPene is an estimate of the probability that the drug will penetrate the blood brain barrier and enter the central nervous system (CNS);

BBB-T2(MD) is the Malanabois distance, which is a measure of the calculated statistical distance from the centre of a population of drugs with optimal blood brain barrier penetration;

ClarkLogBBB is an estimate of a drugs penetration of the blood brain barrier based on the drugs LogP and TPSA;

SubKitLogBB is another estimate of a drugs penetration of the blood brain barrier based on the drugs LogP and TPSA;

LogBB: if LogBB<=-1 the drug does not pentrate the BBB; if Log BB>0 there is likely to be good BB penetration; if -1<logBB<0 then BBB penetration is likely to be variable and may be poor.

Table 5: Metabolic Stability (Percent Remaining at 60 Minutes and Calculated Half Life in Hours)

Table 5 shows that in vitro metabolic stability is expected to be adequate for COTI-217, COTI-220, COTI-219, COTI-2 and COTI-5. COTI-2 is expected to be metabolized more quickly in human liver microsomes than the other COTI compounds. Both the estimated T1/2 and the T1/2 measured in vitro for COTI-2 and 219 are good.

| MolID | Liver Microsomes | Hepatocytes | T½ hrs | 95% CI in Hrs | In vitro T½ (Hrs) |
|---|---|---|---|---|---|
| COTI217 | 54 | 66.4 | 5.3 | 1.9-8.7 | ND |
| COTI220 | 64.1 | 72.5 | 3.9 | 1.4-6.4 | ND |
| COTI219 | 66.7 | 74.18 | 4 | 1.4-6.6 | ~6.8(5.0, 7.0, 8.5) |
| COTI2 | 23.7 | 55.94 | 8.7 | 3.1-14.3 | ~6.0(1.7, 4.8, 11.4) |
| COTI5 | 50.9 | 64.42 | 6.1 | 2.2-10 | ND |

Legend for Table 5:

Liver Microsomes is the estimated percent remaining at 60 minutes after introduction of a dose of the drug into an in vitro/human liver microsomal enzyme system;

Hepatocytes is the estimated percent remaining at 60 minutes after introduction of a dose of the drug into an in vitro/human hepatocyte cellular system;

T1/2 hrs is a calculated estimate of the half life of the drug measured in hours; 95% Cl in Hrs is the calculated 95% confidence interval estimate of the half life of the drug measured in hours;

In vitro T1/2(Hrs) is the actual half life in hours obtained from 3 in vitro experiments carried out at doses of 1 μmol, 10 μmol and 100 μmol (in brackets).

Table 6: Probability (CYP450 Isoenzyme Substrate)

Table 6 shows that COTI-217, COTI-220, COTI-219, COTI-2 and COTI-5 are likely to be metabolized by the CYP450 enzyme system. COTI-217, COTI-220, COTI-219, COTI-2 and COTI-5 are expected to undergo at least some CYP3A457 metabolism and COTI-2 may also undergo some CYP2D6 metabolism.

| MolID | FORMULA | CYP1A2 | CYP2B6 | CYP2C8/9 | CYP2C19 | CYP2D6 | CYP2E1 | CYP3A457 |
|---|---|---|---|---|---|---|---|---|
| COTI217 | C17H22N6S | 0.57 | 0.03 | 0.08 | 0.05 | 0.84 | 0.03 | 0.51 |
| COTI220 | C18H20N6S | 0.07 | 0.02 | 0.12 | 0.05 | 0.22 | 0.02 | 0.93 |
| COTI219 | C17H18N6S | 0.34 | 0.03 | 0.15 | 0.06 | 0.52 | 0.03 | 0.6 |
| COTI2 | C19H22N6S | 0.05 | 0.03 | 0.13 | 0.06 | 0.8 | 0.03 | 0.93 |
| COTI5 | C20H24N6S | 0.21 | 0.03 | 0.2 | 0.07 | 0.58 | 0.04 | 0.87 |

Legend for Table 6:

Table 6 represents the estimated probabilities that the drug in question will undergo at least 20% of its phase 1 metabolism by one or more of the 7 major isoenzyme forms of Cytochrome P450 (CYP450). The isoenzyme forms of CYP450 in Table 6 are: 1A2, 2B6, 2C8 or 9, 2C19, 2D6, 2E1 and 3A4, 5 or 7; these 7 isoenzyme forms account for >80% of phase 1 metabolism of all drugs that are orally administered to humans. The majority of all orally administered drugs are metabolized by the CYP3A family of isoenzymes.

Table 7: Probability (CYP450 Iso Enzyme Inhibitor)

Table 7 shows that COTI-217, COTI-220, COTI-219, COTI-2 and COTI-5 are not expected to significantly inhibit any CYP450 isoenzyme.

| MolID | FORMULA | CYP1A2 | CYP2B6 | CYP2C8/9 | CYP2C19 | CYP2D6 | CYP2E1 | CYP3A457 |
|---|---|---|---|---|---|---|---|---|
| COTI217 | C17H22N6S | 0.1 | 0.06 | 0.08 | 0.07 | 0.22 | 0.07 | 0.22 |
| COTI220 | C18H20N6S | 0.09 | 0.06 | 0.33 | 0.12 | 0.16 | 0.06 | 0.12 |
| COTI219 | C17H18N6S | 0.11 | 0.06 | 0.22 | 0.08 | 0.12 | 0.06 | 0.1 |
| COTI2 | C19H22N6S | 0.09 | 0.06 | 0.33 | 0.18 | 0.37 | 0.07 | 0.4 |
| COTI5 | C20H24N6S | 0.11 | 0.06 | 0.23 | 0.16 | 0.31 | 0.07 | 0.37 |

Legend for Table 7:

Table 7 represents the estimated probabilities that the drug in question will inhibit a given CYP isoenzyme activity by at least 20%; the isoenzyme forms of CYP450 in table 7 are: 1A2, 2B6, 2C8 or 9, 2C19, 2D6, 2E1 and 3A4, 5 or 7; these 7 isoenzyme forms account for >80% of phase 1 metabolism of all drugs that are orally administered to humans.

Table 8: Probability (CYP450 Iso Enzyme Inducer)

Table 8 shows that COTI-217, COTI-220, COTI-219, COTI-2 and COTI-5 are not expected to induce any of the CYP450 isoenzymes.

| MolID | FORMULA | CYP1A2 | CYP2B6 | CYP2C8/9 | CYP2C19 | CYP2D6 | CYP2E1 | CYP3A457 |
|---|---|---|---|---|---|---|---|---|
| COTI217 | C17H22N6S | 0.06 | 0.05 | 0.05 | 0.05 | 0.05 | 0.05 | 0.05 |
| COTI220 | C18H20N6S | 0.23 | 0.05 | 0.05 | 0.05 | 0.05 | 0.05 | 0.05 |
| COTI219 | C17H18N6S | 0.06 | 0.05 | 0.05 | 0.05 | 0.05 | 0.05 | 0.07 |
| COTI2 | C19H22N6S | 0.07 | 0.05 | 0.05 | 0.05 | 0.05 | 0.05 | 0.09 |
| COTI5 | C20H24N6S | 0.07 | 0.05 | 0.05 | 0.05 | 0.05 | 0.05 | 0.07 |

Legend for Table 8:

Table 8 represents the estimated probabilities that the drug in question will induce a given CYP isoenzyme activity by at least 20%. The isoenzyme forms of CYP450 in table 8 are: 1A2, 2B6, 2C8 or 9, 2C19, 2D6, 2E1 and 3A4, 5 or 7; these 7 isoenzyme forms account for >80% of phase 1 metabolism of all drugs that are orally administered to humans.

Table 9: Probability of any Hepatic Toxicity

Table 9 shows that COTI-217, COTI-220, COTI-219, COTI-2 and COTI-5 are not expected to cause Hepatic Toxicity.

| MolID | FORMULA | ProbHepTox1 | ProbHepTox2 |
|---|---|---|---|
| COTI217 | C17H22N6S | 0.146 | 0.086 |
| COTI220 | C18H20N6S | 0.082 | 0.47 |
| COTI219 | C17H18N6S | 0.079 | 0.457 |
| COTI2 | C19H22N6S | 0.065 | 0.371 |
| COTI5 | C20H24N6S | 0.099 | 0.252 |

Legend for Table 9:

ProbHepTox1 is the average calculated probability from an ensemble of models that the drug in question will cause liver toxicity;

ProbHepTox2 is the average calculated probability from a second, different ensemble of models that the drug in question will cause liver toxicity.

Table 10: Probability of P-glycoprotein Interaction

Table 10 shows that COTI-217, COTI-220, COTI-219, COTI-2 and COTI-5 are expected to inhibit P-glycoprotein (P-gp) enzyme activity. COTI-2 and COTI-5 may also be substrates for P-gp, whereas COTI-219 is relatively unlikely to be a substrate for P-gp. P-gp is a protein expressed by many cancer cells and is felt to contribute to cellular resistance to many cancer drugs. Ideally, an effective cancer drug would either not be a substrate for P-gp or would inhibit P-gp activity, thereby reducing the likelihood of P-gp related drug resistance.

| MolID | FORMULA | Substrate | Inhibitor |
|---|---|---|---|
| COTI217 | C17H22N6S | 0.57 | 0.81 |
| COTI220 | C18H20N6S | 0.62 | 0.87 |
| COTI219 | C17H18N6S | 0.19 | 0.75 |
| COTI2 | C19H22N6S | 0.79 | 0.9 |
| COTI5 | C20H24N6S | 0.82 | 0.9 |

Legend for Table 10:

Table 10 represents the calculated probabilities from an ensemble of models that the drug in question will interact with P-glycoprotein (P-gp) as a substrate or inhibitor.

Table 11: Animal and Human Toxicity Predictions

Table 11 shows that COTI-217, COTI-220, COTI-219, COTI-2 and COTI-5 are expected to have low to moderate acute toxicity as measured by LD50 when given by the oral and intraperitoneal route.

| MolID | FORMULA | ORL-LD50 | Lower ORL-LD50 | IPR-LD50 | Lower IPR-LD50 | MRTD mg/kg/day | MRTD mg/day |
|---|---|---|---|---|---|---|---|
| COTI217 | C17H22N6S | 609.7 | 192.8 | 139.6 | 44.2 | 2 | 120.5 |
| COTI220 | C18H20N6S | 761.1 | 240.7 | 175.5 | 55.5 | 1.3 | 79.9 |
| COTI219 | C17H18N6S | 1022 | 323.2 | 227.8 | 72 | 1.2 | 70.4 |
| COTI2 | C19H22N6S | 842.8 | 266.5 | 195.3 | 61.8 | 1.6 | 99 |
| COTI5 | C20H24N6S | 773.9 | 244.7 | 151.5 | 47.9 | 1.1 | 67 |

Legend for Table 11:

ORL-LD50 is the calculated point estimate of the dose of the drug in mg/kg that would cause death in 50% of healthy test lab rats when the drug is given orally;

LowerORL-LD50 is the calculated lower 95% confidence interval point estimate of the dose of the drug in mg/kg that would cause death in 50% of healthy test lab rats when the drug is given orally;

IPR-LD50 is the calculated point estimate of the dose of the drug in mg/kg that would cause death in 50% of healthy test lab mice when the drug is given intraperitoneally;

LowerORL-LD50 is the calculated lower 95% confidence interval point estimate of the dose of the drug in mg/kg that would cause death in 50% of healthy test lab mice when the drug is given intraperitoneally;

MRTDmg/kg/day is the calculated maximum recommended therapeutic daily dose of the drug in milligrams per kg per day for the average 60 Kg human adult;

MRTDmg/day is the calculated maximum recommended therapeutic daily dose of the drug in milligrams per day for the average 60 Kg human adult.

Table 12: Predicted hERG Interaction

Table 12 shows that COTI-217, COTI-220, COTI-219, COTI-2 and COTI-5 are expected to have hERG IC50 values of >1 μmol/l in keeping with a decreased risk of cardiac toxicity. In general, a hERG IC50 of <1 μmol/L would be associated with an increased probability of potential drug induced cardiac toxicity.

| MolID | FORMULA | IC50 (μmol) | ProbIC50 > 1 μmol | ProbIC50 > 10 |
|---|---|---|---|---|
| COTI217 | C17H22N6S | 2.6 | 0.88 | 0.06 |
| COTI220 | C18H20N6S | 1.8 | 0.9 | 0.03 |
| COTI219 | C17H18N6S | 2.2 | 0.92 | 0.04 |
| COTI2 | C19H22N6S | 1.6 | 0.92 | 0.02 |
| COTI5 | C20H24N6S | 0.6 | 0.79 | 0.04 |

Legend for Table 12:

IC50 (μmol) is the calculated concentration of the drug that inhibits 50% of the activity of the hERG potassium channel and is an estimate of potential cardiac toxicity;

ProbIC50>1 μmol is the calculated probability that the IC50 for the drug with regards to the hERG potassium channel is greater than 1 μmol/L;

ProbIC50>10 μmol is the calculated probability that the IC50 for the drug with regards to the hERG potassium channel is greater than 10 μmol/L;

Table 13: Predicted Genotoxicity

Table 13 shows that COTI-2 and 219 are expected to have a negative AMES test and that COTI-217, COTI-220, COTI-219, COTI-2 and COTI-5 are not expected to cause Polyploidicity in the Guinea Pig cell model.

| MolID | FORMULA | ProbAMES+ | PolyPldy |
|---|---|---|---|
| COTI217 | C17H22N6S | 0.94 | 0.15 |
| COTI220 | C18H20N6S | 0.06 | 0.16 |
| COTI219 | C17H18N6S | 0.06 | 0.15 |
| COTI2 | C19H22N6S | 0.06 | 0.16 |
| COTI5 | C20H24N6S | 0.06 | 0.23 |

Legend for Table 13:

ProbAMES+ is the probability that the drug will induce a recognized gene mutation in a standard strain of cultured bacteria;

PolyPldy is the probability that the drug will induce polyploidicity (i.e. an increased/abnormal number of chromosomes) in cultured guinea pig cells.

Example 2

In Vitro Efficacy Against Various Cancer Cell Lines

To assess the efficacy of compounds according to the present invention in the treatment of cancer, in vitro activity expressed as IC50 (represents the concentration of an inhibitor that is required for 50% inhibition of its target, in nmol) was measured for several cancer cell lines using standard methods for such tests known to persons skilled in the art. Briefly, cells were plated in plastic tissue culture plates and grown under standard conditions for each cell line, in carbon dioxide/oxygen atmosphere in plastic tissue culture plates, in the presence of COTI-2 or COTI-219 compounds at 35° C. for 3 days. Control cultures were treated with vehicle minus compound. Cells were counted after 3 days in culture and at a cell density of no more than 80%. The following cell lines, obtained from the National Cancer Institute, were tested: human SCLC cell lines DMS 153, DMS114, SHP77; human NSCLC cell lines H226, A460, A560; human breast cancer cell lines T47D, MCF7; human colon cancer cell line HT29; and, human Leukemia cell lines K562, HL60. The results of these assays are presented in Table 14.

TABLE 14 in vitro IC50 against cancer cell lines

| Cell Line | Tumor Type | COTI-2 IC50 (nM) | COTI-219 IC50 (nM) |
|---|---|---|---|
| SHP77 | SCLC | 156 +/− 8 | 787 +/− 61 |
| DMS153 | SCLC | 73 +/− 9 | 233 +/− 39 |
| DMS114 | SCLC | 51 +/− 9 | 267 +/− 40 |
| H226 | NSCLC | 15000 +/− 1129 | Not tested |
| A460 | NSCLC | 7900 +/− 620 | Not tested |
| A549 | NSCLC | 6300 +/− 671 | Not tested |
| T47D | Breast Cancer | 221 +/− 12 | 367 +/− 44 |
| MCF7 | Breast Cancer | 101 +/− 8 | 421 +/− 31 |
| HT29 | Colorectal Cancer | 121 +/− 11 | 403 +/− 32 |
| K562 | Leukemia | 176 +/− 22 | 222 +/− 28 |
| HL60 | Leukemia | 236 +/− 9 | 374 +/− 46 |

Table 14 shows that both COTI-2 and COTI-219 possess potent activity in the low nanomolar range against SCLC tumor cell types, as well as several other tumor cell types such as breast cancer, colorectal cancer and Leukemia. Both drugs had an IC50 of less than 850 nM for the SHP77 cell line, which is known to be resistant to several conventional therapeutic agents. COTI-2 did not possess nanomolar level activity against NSCLC cell types and COTI-219 was not tested against those cell types. At least COTI-2 therefore exhibits selectivity in lung cancer treatment towards SCLC cell types. The in vitro data also confirms the in-silico predictions of efficacy, which estimated that less than 1 μM (1000 nM) would be required for efficacy in the SHP 77 and DMS 114 cell lines.

Example 3

In Vivo Efficacy in SCLC Treatment

The nude mouse model of human SCLC was used to evaluate the in vivo efficacy of compounds of the present invention in comparison with several known chemotherapeutic agents. Nude mice were obtained form the National Cancer Institute and the SHP-77 human SCLC cell line was chosen for metastatic tumor xenografts. The control group consisted of 10 animals, each of which were administered bilateral thigh injections of a prescribed volume of tumor cells. There were 6 treatment groups, each containing 5 animals: COTI-2, COTI-4, COTI-219, Taxotere® (docetaxel), Cisplatin® (cis-diamminedichloroplatinum) and Tarceva® (erlotinib) The therapeutic agent was administered by intraperitoneal (IP) injection on alternate days beginning on Day 3 post tumor cell injection. Each animal in a treatment group was administered bilateral thigh injections with the same prescribed volume of tumor cells as the control animals. Treatment continued for 31 days, following which the animals were euthanized and tissues were collected for subsequent analysis. The final tumor size in $mm^3$ is reported in FIG. 1 and the number of tumors is reported in FIG. 2.

Referring to FIG. 1, compounds according to the invention showed a marked decrease in tumor growth as compared with both the control and conventional agents. Control animals produced tumors having a mean volume of 260+/−33 $mm^3$. Animals treated with COTI-2 produced tumors of mean volume 9.9 $mm^3$, while those treated with COTI-219 produced tumors having mean volume 53+/−28 $mm^3$. This compared well with those treated with Cisplatin®, which produced tumors having means volume 132+/−26 $mm^3$ and those treated with Taxotere®, which produced tumors having mean volume 183 $mm^3$. Animals treated with Tarceva® died before study conclusion at 31 days.

Figure 2:
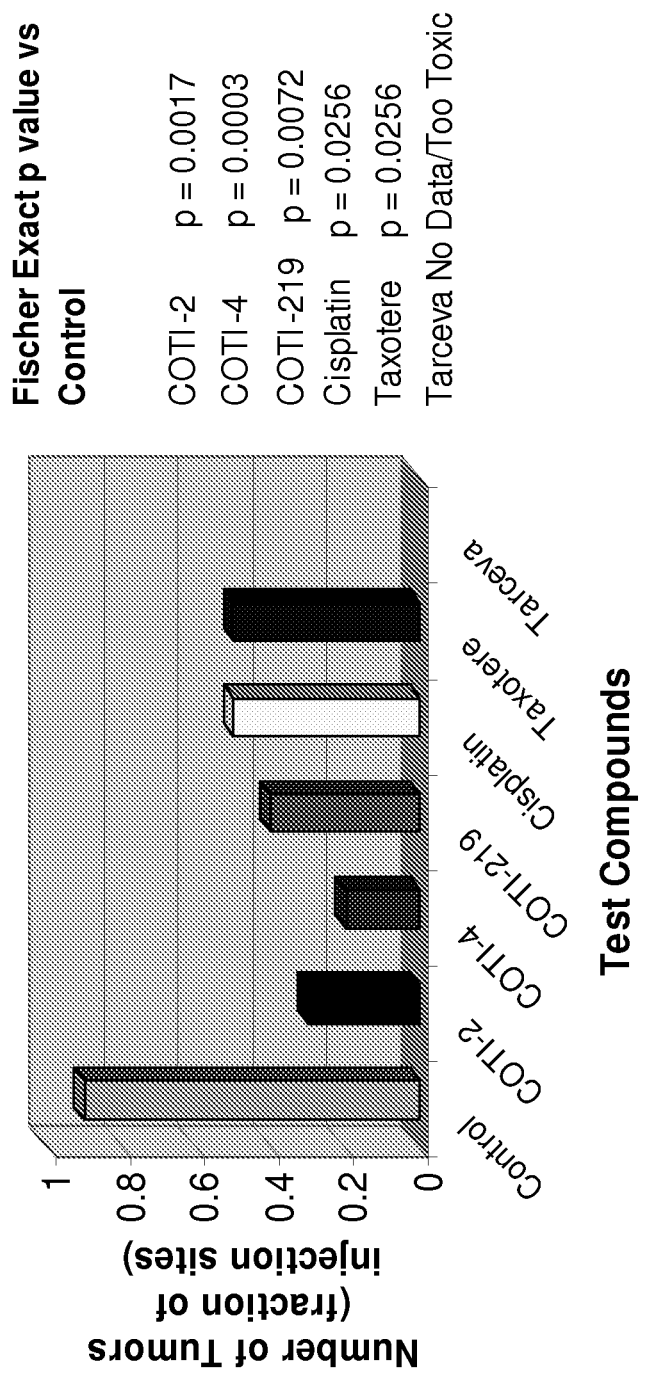
FIG. 2 shows number of SHP77 human SCLC tumours in nude mice treated with test compounds.

Referring to FIG. 2, compounds according to the invention showed a marked decrease in number of tumors as compared with both the control and conventional agents. Control animals produced an average of 0.9 tumors per injection site, whereas those treated with COTI-2 produced 0.28, those treated with COTI-219 produced 0.38, those treated with Cisplatin® produced 0.48 and those treated with Taxotere® produced 0.48. Animals treated with Tarceva® died before study conclusion at 31 days.

The above data show the efficacy of compounds according to the invention in vivo against SCLC cell lines. Furthermore, compounds according to the invention show better efficacy compared to conventionally administered therapeutic agents.

Example 4

In Vivo Effect of COTI-2 in SCLC Treatment on N417 Tumor xenografts

Malignant N417 human SCLC cells in Matrigel™ were injected subcutaneously into hind legs of nude mice and xenograft tumors were allowed to grow to about 100 $mm^3$. Mice were then administered daily intraperitoneal injections with indicated concentrations of COTI-2 (in isotonic saline, as a cloudy liquid, total volume of 1 ml per injection) for one week. Tumor volumes were estimated by caliper measurement. The results are shown in FIG. 3.

Figure 3:
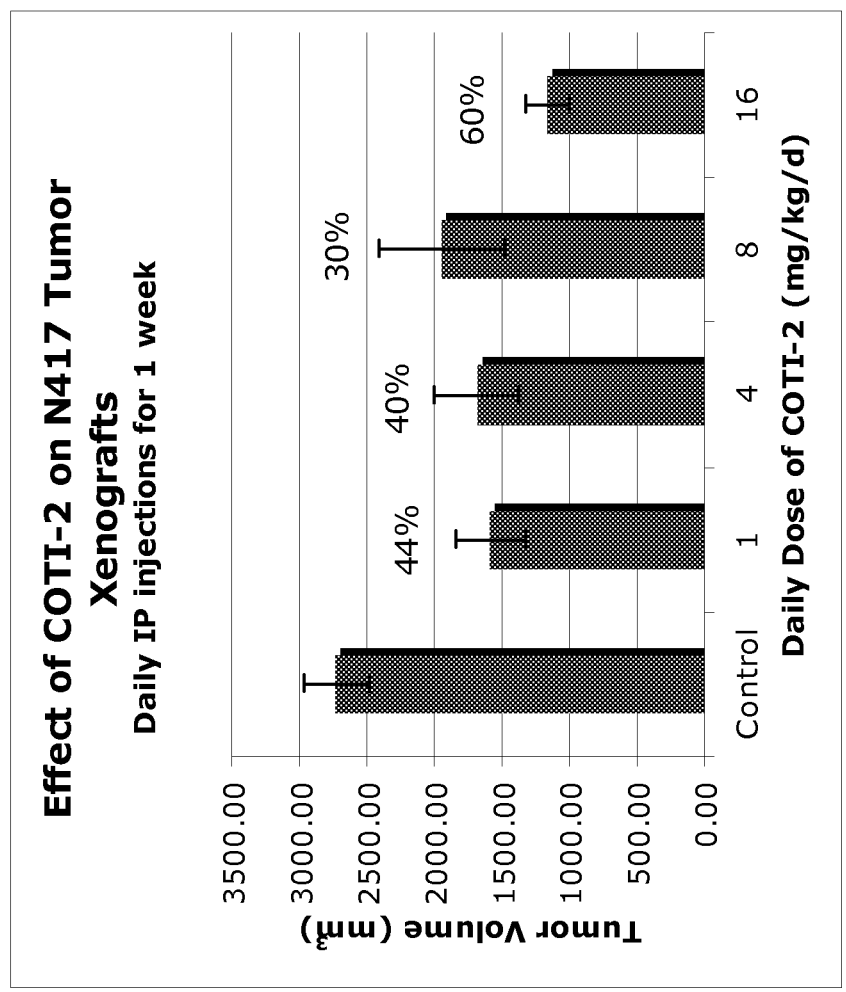
FIG. 3 shows the volume of N417 human SCLC tumour in nude mice treated with COTI-2 and control.

Referring to FIG. 3, tumor volumes were graphed as means±standard error (SE).

A significant difference in tumor growth was observed at all dosage levels. The decrease in efficacy seen at the 8 mg/kg level relative to other treatment levels is attributed to an error in solubilizing the compound, since a small amount of undissolved material was observed at the bottom of the treatment vial. Percentage values reported on FIG. 3 are for efficacy of the compound expressed in terms of inhibition of tumor growth according to the following formula:

(1−(Tf−Ti)/(Cf−Ci))*100 wherein Tf is the final tumor volume, Ti is the initial tumor volume at the onset of treatment, Cf is the final control tumor volume and Ci is the initial control tumor volume at the onset of treatment. Even when the 8 mg/kg dose is included, tumor growth inhibition of 30% or more was observed across all dosage levels. It is noted that the N417 cell line is generally regarded as the hardest SCLC cell line to treat. The compounds according to the invention therefore exhibit in vivo efficacy against a number of different SCLC cell lines.

Example 5

Resistance Testing

In order to evaluate the induction of resistance in vitro, compounds according to the invention were tested in head to head comparisons against conventional therapeutic agents Cisplatin® and Taxotere®. The compound designated COTI-4 (which is the subject of Applicant's co-pending U.S. provisional patent application entitled "Composition and Method for Treatment" filed Dec. 26, 2007) was also tested. The structure for COTI-4 is:

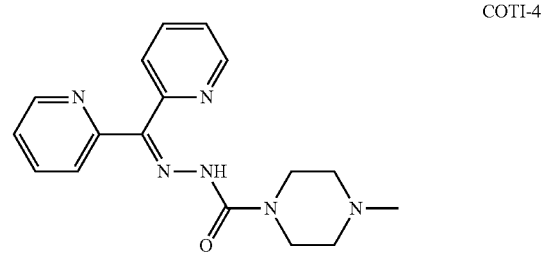 [SMILES: CN1CCN(C(=O)NN=C(c2ccccn2)c2ccccn2)CC1]

COTI-4

IC50 values were obtained using methods known to persons skilled in the art with two different human SCLC cell lines (DMS153 and SHP77) obtained from the National Cancer Institute. The surviving 50% of cells from the initial IC50 tested were harvested and cultured for 5 days, after which time this new generation of cells was re-treated with the same agent and a new IC50 value was established. The procedure was repeated for a total of 5 generations. Emerging resistance was identified by increasing IC50 values in successive generations. The results are shown in FIGS. 4 and 5 (DMS153 and SHP77 cell lines, respectively), where the ordinate axis is provided in terms of the ratio of the IC50 value to the IC50 value of the parental generation.

Figure 4:
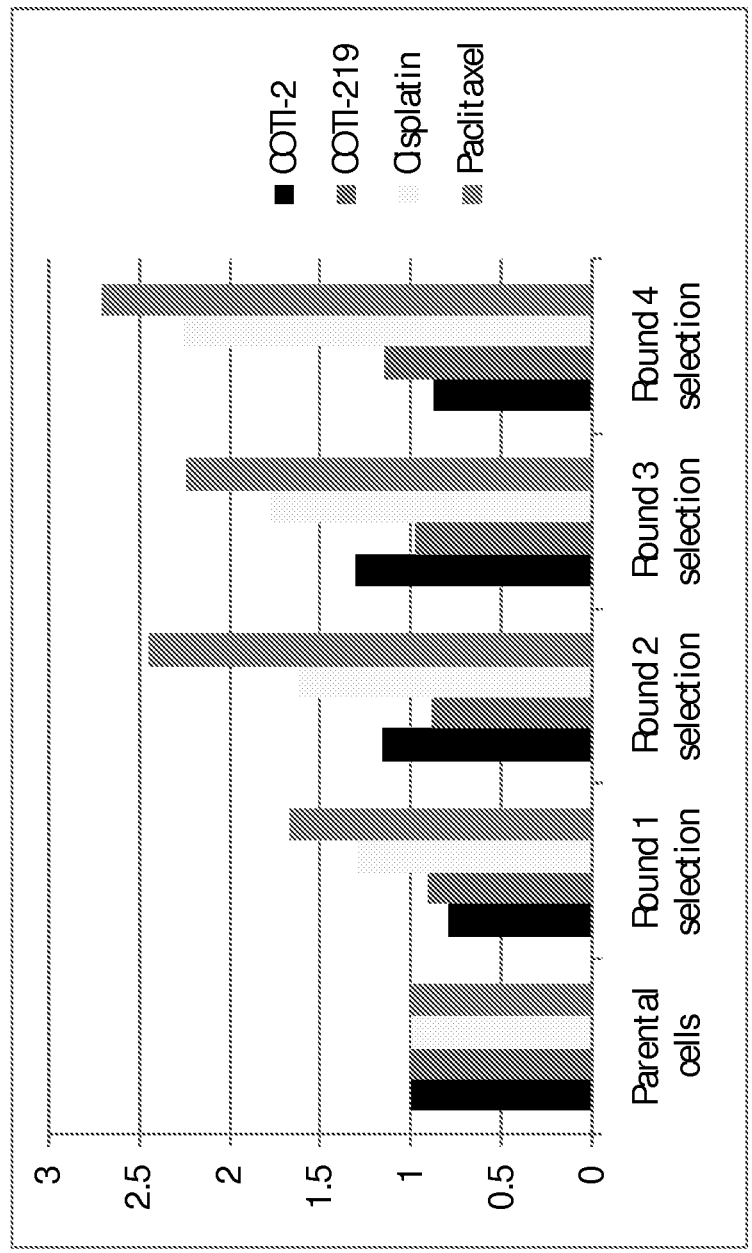
FIG. 4 shows lack of emerging resistance in DMS153 cells treated with COTI-2 and COTI-219.
Figure 5:
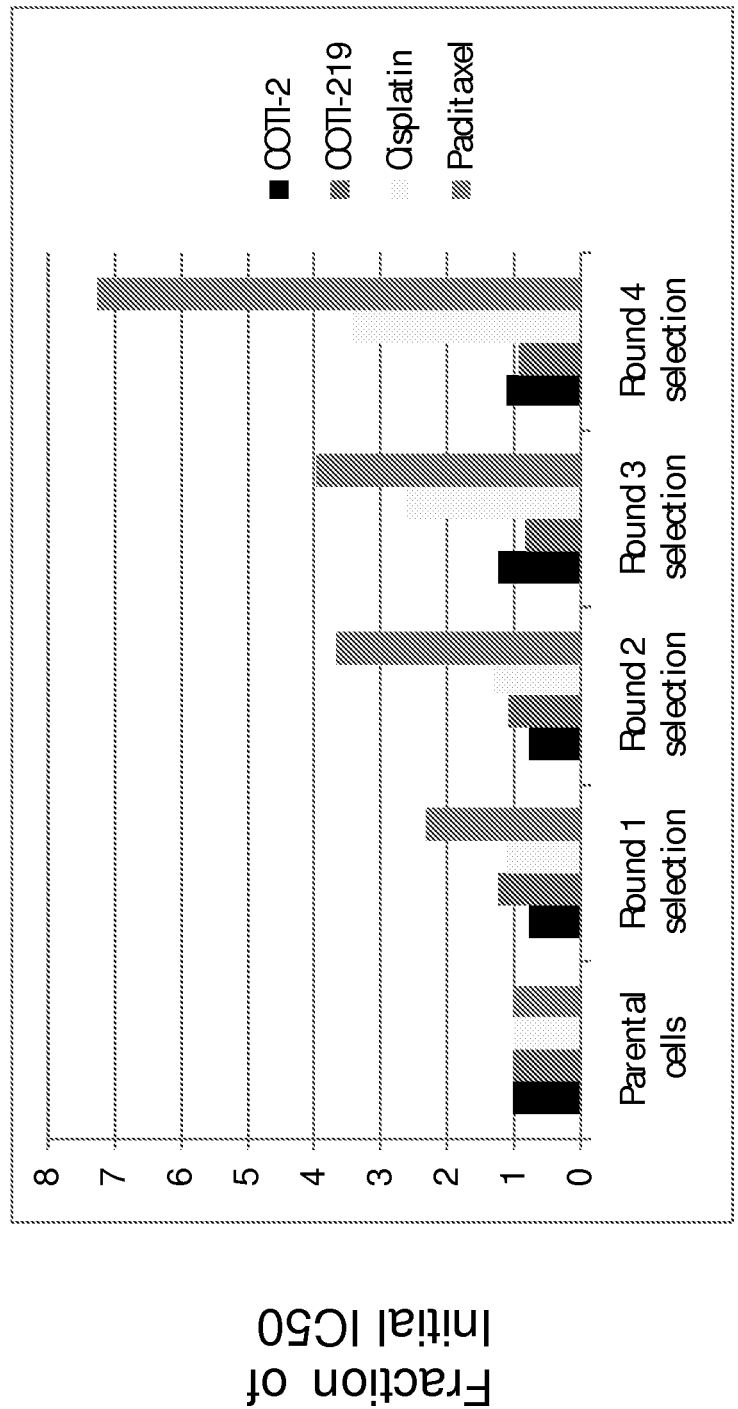
FIG. 5 lack of emerging resistance in SHP77 cells treated with COTI-2 and COTI-219.

Referring to FIGS. 4 and 5, both COTI-2 and 219 exhibited little to no emerging resistance over 5 generations. This was in marked contrast to the conventional therapies Cisplatin® and Taxotere® (labeled Paclitaxel in the figures), which showed significant increases in IC50 for both cell lines. The SHP77 cell line in particular is known to be resistant to conventional agents; however, neither COTI 2 nor 219 showed any tendency towards resistance in this cell line. In fact, COTI-2 demonstrated a statistically significant tendency to decrease resistance (IC50's less than 1 for successive generations) in both cell lines. COTI-2 therefore exhibits a collateral sensitivity whereby the resistance of cells is decreased over successive generations and the drug might actually become more effective over time against these cell lines. This corroborates the in-silico predictions for COTI-2 and 219; COTI-2 was predicted to be a strong P-glycoprotein inhibitor, which is consistent with decreasing the tendency towards drug resistance, whereas COTI-219 was predicted to be both a P-glycoprotein inhibitor and/or a weak substrate for P-glycoprotein, also consistent with minimal accumulation in resistance over successive generations. The in-silico predictions for resistance profile of compounds according to the invention are therefore confirmed by these assays.

Example 6

In Vitro Efficacy in Brain Cancer

In order to determine the efficacy of the present invention against human Glioma and Astrocytoma cell lines, IC50 values were determined by in vitro assay of four malignant human brain cancer cell lines (U87MG, grade III glioblastoma/astrocytoma; SNB-19, glioma/astrocytoma Grade IV, glioblastoma multiforme; SF-268, glioma; SF-295, glioma). Human brain cancers are notoriously difficult to treat.

Cell lines were obtained from the Human Tissue Culture Collection (ATCC), grown and maintained under ATCC-specified conditions, and tested to ensure viability and lack of contaminating mycoplasma and common viruses. Healthy cells were plated in 96-well culture plates in medium plus fetal bovine serum and allowed to adhere for 16 h, followed by addition of COTI-2, COTI-219, Cisplatin®, or BCNU (1,3-Bis(2-chloroethyl)-1-nitrosourea) at multiple concentrations ranging from those that had no effect on proliferation to those that inhibited proliferation by 90% or more. A viability stain (alamar Blue) was added to cells after 4-7 days of drug exposure (approximately 4 doublings of control cells; maximum cell density in wells approximately 80%), and assayed for total cellular metabolic activity (a function of population density of live cells) by absorbance. Concentrations of the agent required to inhibit proliferation by 50% (IC50 value) were derived by interpolation of plotted data (mean values derived from 3 independent experiments ±standard error). Results are reported in Table 15.

TABLE 15

| IC50 values for Human Glioma/Astrocytoma cell Lines | | | | |
| --- | --- | --- | --- | --- |
| Cell Line | COTI-2 (nM) | COTI-219 (nM) | Cisplatin (nM) | BCNU (nM) |
| U87 | 48 +/− 9 | 2370 +/− | 490 +/− 9 | 1520 +/− 130 |
| SNB-19 | 8 +/− 3 | 1990 +/− | 870 +/− 40 | 2250 +/− 700 |
| SF-268 | 66 +/− 8 | 1170 +/− | Not tested | Not tested |
| SF-295 | 184 +/− 23 | 2390 +/− | Not tested | Not tested |

At least the COTI-2 compounds were shown to have better efficacy against glioma/astrocytoma cell lines as compared with the conventional agents Cisplatin® and BCNU. COTI-2 showed an order of magnitude greater efficacy than Cisplatin® against U87 and two orders of magnitude greater efficacy against SNB-19. These results show that at least COTI-2 compounds have efficacy against glioma/astrocytoma cell lines.

Example 7

In Vivo Effect of COTI-2 on Cancerous Brain Tumours

Malignant U87 human glioma (brain tumour) cells in Matrigel™ were injected sub-cutaneously into hind legs of nude mice, allowed to grow to 200-300 mm$^3$, then treated 3 times per week (Mon, Wed, Fri) with indicated concentrations of COTI-2 (in isotonic saline, as a cloudy liquid, total volume of 1 ml per injection). Tumour volumes were estimated by caliper measurement. The results are shown in FIGS. 6A and 6B.

Figure 6A:
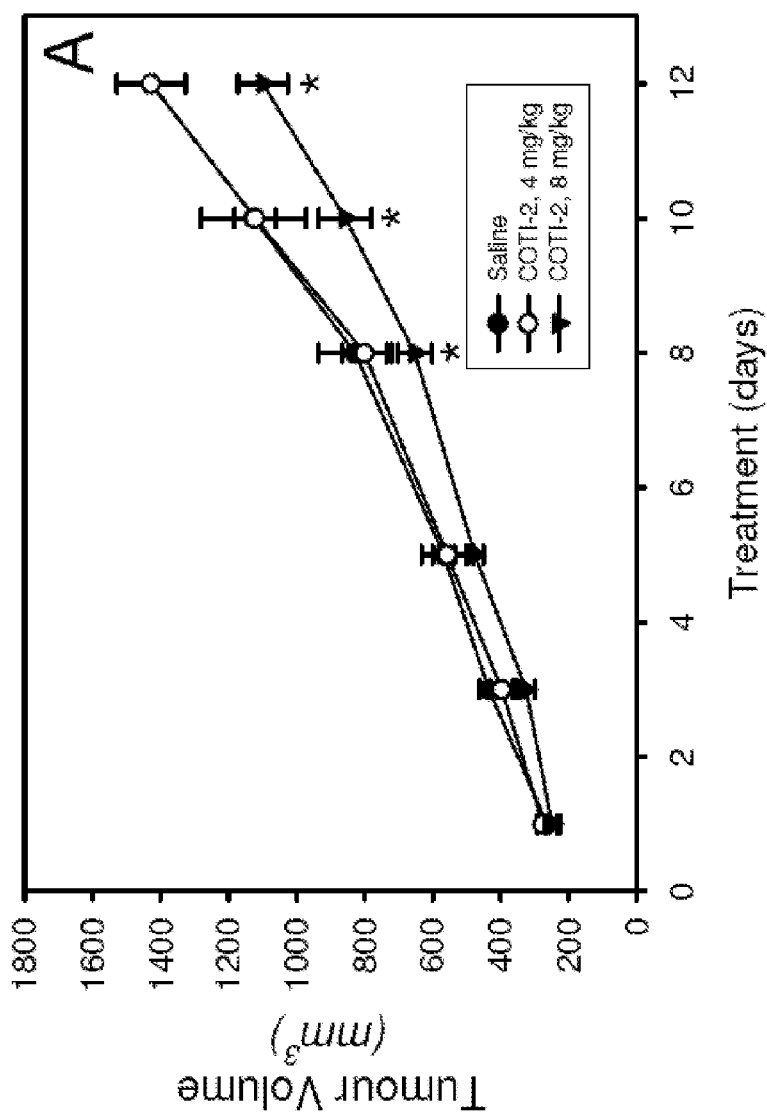
FIGS. 6A and 6B show volume of U87 human glioma tumours in nude mice treated with two different concentrations of COTI-2.

In FIG. 6A, tumour volumes were graphed as means±standard error (SE) (n=11-14 for each data point). The asterisk indicates a significant difference (p<0.05) between the 8 mg/kg treatment group and both the saline control and 4 mg/kg treatment groups. There was no significant difference between the 4 mg/kg group and the saline control group.

Figure 6B:
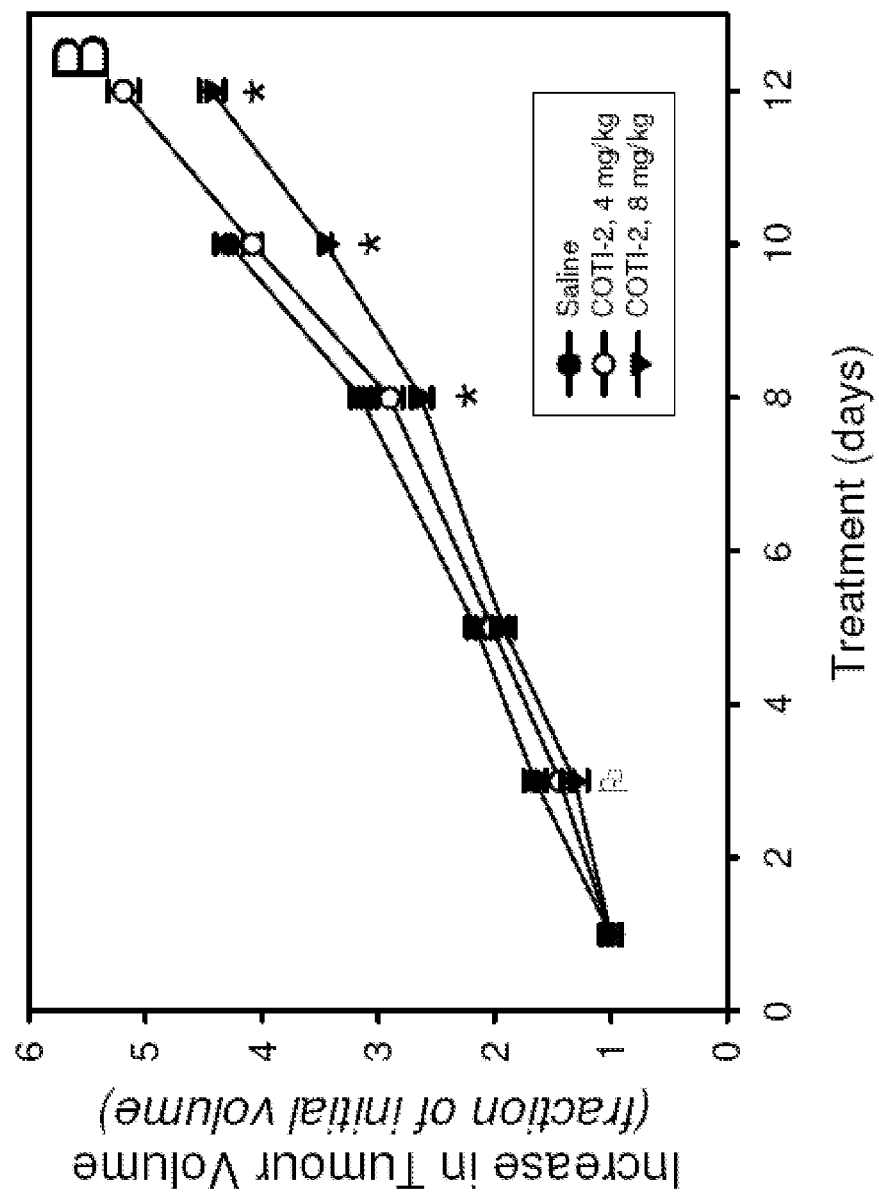

In FIG. 6B, tumour volumes were graphed as fractional increase in volume, to correct for differences in starting volume, ±SE. The asterisk indicates a significant difference (p<0.05) between the 8 mg/kg treatment group and both the saline control and 4 mg/kg treatment groups. There was no significant difference between the 4 mg/kg group and the saline control group. The flag (⊬) indicates a significant difference between the 8 mg/kg group and the saline group, but not between the 8 mg/kg group and the 4 mg/kg group.

FIGS. 6A and 6B show that compounds of the present invention are effective in the treatment of established human brain tumors. The compounds delayed tumor growth by about 25% at a dosage of 8 mg/kg given just three times per week. Although no significant effect was observed at a dosage of 4 mg/kg, more frequent administration may have produced a significant effect at this dosage.

Example 8

Toxicity Testing

An escalating dose acute toxicity study was conducted with COTI-2, COTI-4 and COTI-219. Standard lab mice were divided into four treatment groups (control, 4, 8, 16 mg/kg) with four animals per group. It should be noted that the highest dose was approximately 10 times the estimated effective dose. Mice were given alternate day IP injections for 28 days. Weight loss/gain of the mice was measured and the mice were observed for adverse effects such as vomiting, diarrhea, seizures, etc. Blood and tissue samples were harvested for histopathology. None of the drugs produced any weight loss at any of the administered doses over the entire 28 day period. No evidence of acute toxicity was obtained and no adverse effects were observed. The compounds according to the present invention are therefore believed to be safe and non-toxic.

Example 9

In Vitro Metabolic Stability in Human Liver Microsomes

To evaluate the stability of these compounds in terms of clearance by the liver, human liver microsomes (HLM) at a concentration of 0.5 mg/ml were incubated with 0.823 mM NADPH, 5 mM UDPGA, 1 mM MgCl$_2$ and COTI-2 or 219 at concentrations of 1, 10 and 100 µM. Sampling was conducted at 1, 20, 40, 60, 120, 180 and 240 minutes and the remaining concentration of each compound was evaluated. A half life ($T_{1/2}$) was calculated at each concentration, along with the rate of clearance by the liver ($C_L$). The results are provided in Table 16 for each compound. The $C_L$ values compare favorably with published values for other marketed therapeutic agents under identical conditions. The half life of compounds according to the invention is therefore likely to be long enough to permit convenient dosing, while not being so long as to lead to accumulation in patients with potential long term toxicity effects.

TABLE 16

Half-life and Liver Clearance Rate by HLM at 0.5 mg/mL

| Compound | Concentration (μM) | $T_{1/2}$ (min) | $C_L$ (μL/min/mg) |
|---|---|---|---|
| COTI-2 | 1 | 102.1 | 12 |
| | 10 | 285.7 | 4 |
| | 100 | 683.1 | 2 |
| COTI-219 | 1 | 301.2 | 4.2 |
| | 10 | 420.7 | 3 |
| | 100 | 508.5 | 2.5 |

The average half life for COTI-2 was 6 hours and for COTI-219 was 6.8 hours. The in-silico prediction for CL in the 95% confidence interval was from 3.1-14.3 for COTI-2 and from 1.4-6.6 for COTI-219; this compares well with the data presented in Table 3.

Example 10

Mechanism of Action

Without wishing to be limited by theory, it is believed that molecules according to the present invention, particularly COTI-2, act in the treatment of cancer in a manner consistent with the following mechanistic observations. The following observations were obtained using gene expression profiling techniques and targeted in vitro testing. Molecules of the present invention are believed to function as kinase inhibitors. Molecules of the present invention are also believed to function as promoters of apoptosis. Promotion of apoptosis is achieved by decreasing phosphorylation of Caspase 9; this has the effect of increasing active Caspase 9 and inducing apoptosis via Caspase 3.

Figure 7:
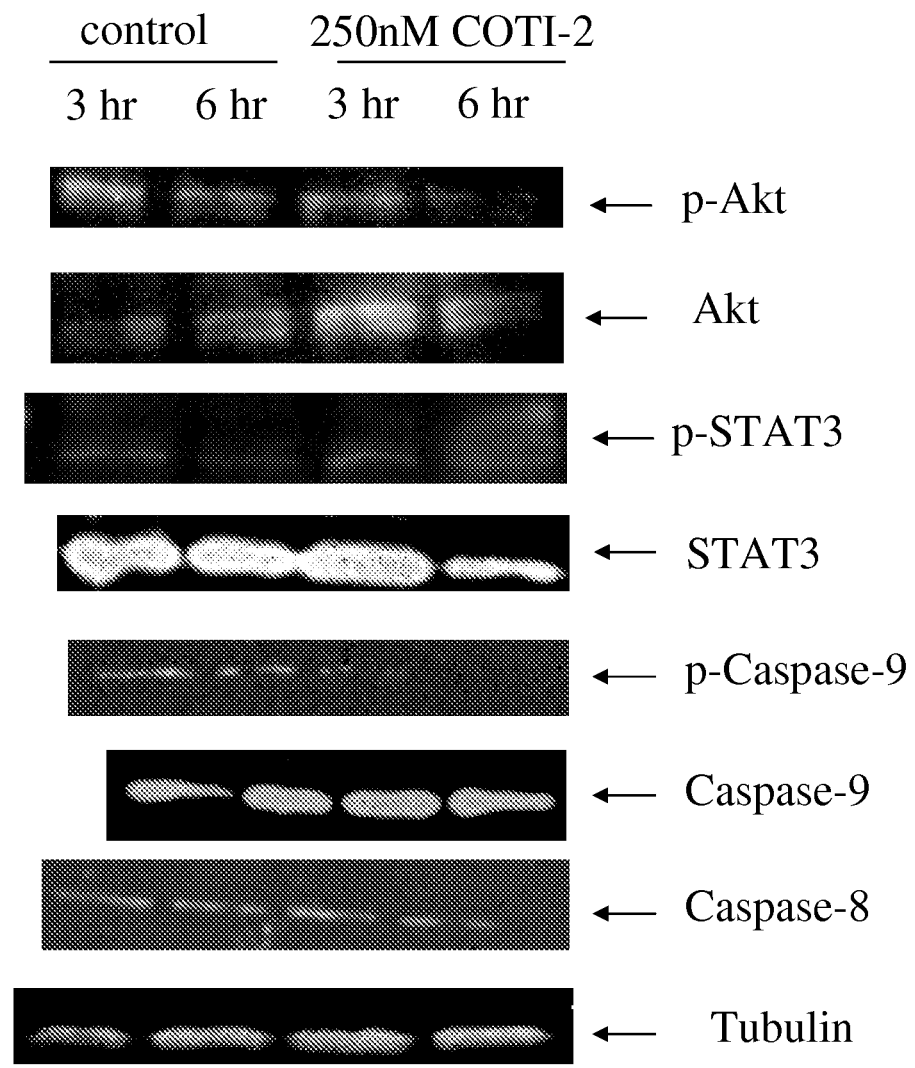
FIG. 7 shows Western blot analysis of cellular lysates of SHP77 cells that have been treated with COTI-2.

To confirm this mechanism SHP77 cells were treated with 250 nM of COTI-2 and incubated for 3 and 6 hours. Western blots of the cellular lysates are presented in FIG. 7. Phospho-Akt expression was decreased as compared to control at both 3 and 6 hours, with corresponding increases in Akt levels. There was no change in phospho-STAT3 expression, although a slight decrease in total STAT3 (~30%) was observed at 6 hrs. There was no observed reactivation of Caspase 8; its level of expression remained constant in treated and control cells. However, the most dramatic change was a profound suppression of phospho-Caspase 9 at both 3 and 6 hrs of incubation. These results confirm the proposed mechanism of action.

Example 11

In-Silico Comparative Data

The in-silico model was used to test properties of compounds described in PCT Publication No. WO2006/009765: NSC716768, NSC73306, NSC73303, NSC668496, and NSC693323. Compounds JBC271A, JBC271B (Journal of Biological Chemistry 271, 13515-13522 (1996)) and JICS75 (Journal of the Indian Chemical Society, 75, 392-394 (1998) and Journal of the Indian Chemical Society, 72, 403-405 (1995)) are as follows:

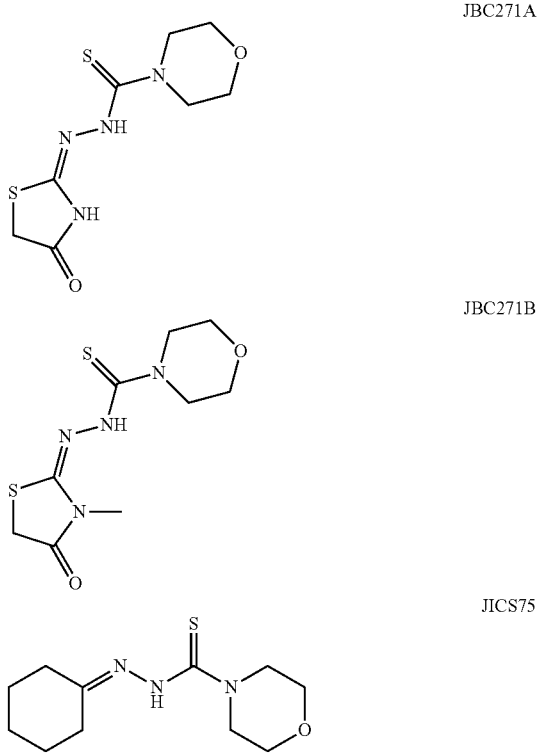

Results of in-silico testing are shown in Tables 17 to 20. The legends for these tables correspond to those of Example 1, except where indicated, and the methodology used to create the Tables was identical.

Tables 17A and 17B: Physical Chemical Properties

Table 17 shows that all tested compounds are drug like with no alerts for poor absorption or bioavailability.

TABLE 17A

| MolID | FORMULA | MolWeight | MnLogP | HBnd Don | HBnd Acc |
|---|---|---|---|---|---|
| NSC716768 | C17H20N6O4S | 404.449 | 2.082079 | 2 | 10 |
| NSC73306 | C16H12Cl2N4O2S | 395.268 | 3.155598 | 3 | 6 |
| NSC73303 | C15H12N4OS | 296.352 | 2.564086 | 3 | 5 |
| NSC668496 | C15H18N4OS | 302.4 | 2.541123 | 2 | 5 |
| NSC693323 | C14H24N6S2 | 340.516 | 2.39891 | 2 | 6 |
| JBC271A | C8H12N4O2S2 | 260.338 | 0.257966 | 2 | 6 |
| JBC271B | C9H14N4O2S2 | 274.365 | 0.542592 | 1 | 6 |
| JICS75 | C11H19N3OS | 241.357 | 1.600519 | 1 | 4 |

TABLE 17B

| MolID | FORMULA | TPSA | RotBnds | Lipinski Alerts | Veber |
|---|---|---|---|---|---|
| NSC716768 | C17H20N6O4S | 112.7027 | 7 | 0 | 0 |
| NSC73306 | C16H12Cl2N4O2S | 75.9848 | 5 | 0 | 0 |
| NSC73303 | C15H12N4OS | 67.0547 | 4 | 0 | 0 |
| NSC668496 | C15H18N4OS | 57.597 | 3 | 0 | 0 |
| NSC693323 | C14H24N6S2 | 54.972 | 7 | 0 | 0 |
| JBC271A | C8H12N4O2S2 | 66.5271 | 3 | 0 | 0 |
| JBC271B | C9H14N4O2S2 | 57.0694 | 3 | 0 | 0 |
| JICS75 | C11H19N3OS | 36.4161 | 3 | 0 | 0 |

Table 18: Solubility Properties

Table 18 shows that all tested compounds have acceptable and comparable solubility with the COTI compounds except for NSC73306 which would be expected to have very poor water solubility.

| MolID | FORMULA | MnLogP | LogS |
|---|---|---|---|
| NSC716768 | C17H20N6O4S | 2.082079 | −3.46551 |
| NSC73306 | C16H12Cl2N4O2S | 3.155598 | −5.76993 |
| NSC73303 | C15H12N4OS | 2.564086 | −3.7869 |
| NSC668496 | C15H18N4OS | 2.541123 | −3.87371 |
| NSC693323 | C14H24N6S2 | 2.39891 | −3.27041 |
| JBC271A | C8H12N4O2S2 | 0.257966 | −1.76143 |
| JBC271B | C9H14N4O2S2 | 0.542592 | −1.83773 |
| JICS75 | C11H19N3OS | 1.600519 | −2.45438 |

Table 19: Efficacy (LogGI50)

Table 19 shows that all tested compounds except for NSC693323 are predicted to be inactive against human SCLC cell lines DMS114 and SHP-77 in vitro. Therefore, there is no rationale for use of any of the tested compounds except for NSC693323 as therapeutic agents in the treatment of SCLC. NSC693323 has an average G150 of −6.3. By comparison, COTI-2 has LOG (G150) for DMS114 determined in vitro of −7.2 to −7.4, representing ~10 times better in vitro efficacy than the predictions for NSC693323

| MolID | FORMULA | DMS 114 | SHP-77 | Predicted | Mean Over NCI/DTP 60 cell line panel |
|---|---|---|---|---|---|
| NSC716768 | C17H20N6O4S | <−6 | <−6 | Inactive | −4.7 |
| NSC73306 | C16H12Cl2N4O2S | <−6 | <−6 | Inactive | −4.9 |
| NSC73303 | C15H12N4OS | <−6 | <−6 | Inactive | ND |
| NSC668496 | C15H18N4OS | <−6 | <−6 | Inactive | −6.1 |
| NSC693323 | C14H24N6S2 | <−6 | <−6 | Active | −6.3 |
| JBC271A | C8H12N4O2S2 | <−6 | <−6 | Inactive | ND |
| JBC271B | C9H14N4O2S2 | <−6 | <−6 | Inactive | ND |
| JICS75 | C11H19N3OS | <−6 | <−6 | Inactive | ND |

Legend for Table 19:

Mean Over NCI/DTP 60 cell line panel is the mean of the G150's for all 60 cell lines NOT including DMS114 and SHP-77;

ND means not done/not available.

Table 20: Oral Absorption and BBB Penetration

Table 20 shows that all tested compounds are predicted to have good oral absorption with variable to poor CNS penetration. The only potentially active drug, NSC693323, likely penetrates into the CNS poorly.

TABLE 20A

| MolID | FORMULA | Mn % OrlAbs | Min % Abs | HIA-T2 (MD) |
|---|---|---|---|---|
| NSC716768 | C17H20N6O4S | 86.33807 | 71.33807 | 3.556507 |
| NSC73306 | C16H12Cl2N4O2S | 73.43512 | 58.43512 | 2.075257 |
| NSC73303 | C15H12N4OS | 88.14632 | 73.14632 | 0.078544 |
| NSC668496 | C15H18N4OS | 87.81207 | 72.81207 | 0.055115 |
| NSC693323 | C14H24N6S2 | 84.59752 | 69.59752 | 0.097439 |
| JBC271A | C8H12N4O2S2 | 80.28443 | 65.28443 | 2.273772 |
| JBC271B | C9H14N4O2S2 | 84.04259 | 69.04259 | 2.267253 |
| JICS75 | C11H19N3OS | 91.74003 | 76.74003 | 2.023605 |

TABLE 20B

| MolID | FORMULA | ProbBBBPene | LogBBB | BBB-T2 (MD) |
|---|---|---|---|---|
| NSC716768 | C17H20N6O4S | 0.009519 | <<−1.00 | 9.681481 |
| NSC73306 | C16H12Cl2N4O2S | 0.051291 | −0.1554 | 4.758413 |
| NSC73303 | C15H12N4OS | 0.359669 | −0.41974 | 1.216003 |
| NSC668496 | C15H18N4OS | 0.306419 | −0.26927 | 0.426904 |
| NSC693323 | C14H24N6S2 | 0.265543 | −0.24742 | 0.294411 |
| JBC271A | C8H12N4O2S2 | 0.818135 | −1.12483 | 3.888207 |
| JBC271B | C9H14N4O2S2 | 0.806343 | −0.91155 | 3.439832 |
| JICS75 | C11H19N3OS | 0.840636 | −0.25614 | 1.981566 |

What is claimed is:

1. A compound of Formula I or IA:

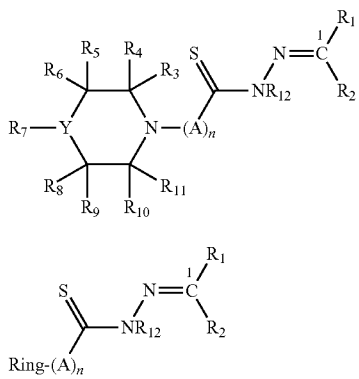

Formula I

Formula IA

Ring-(A)$_n$ a pharmaceutically-acceptable salt, tautomer, optical isomer, and/or combination thereof;

wherein:

R$_1$ and R$_2$ together form a substituted or unsubstituted polycyclic ring comprising at least two ring systems, said at least two ring systems comprising a first ring system bonded to C1 and a second ring system fused to the first ring system, wherein:

the first ring system is a substituted or unsubstituted aromatic group, the second ring system is a substituted or unsubstituted aromatic group, a substituted or unsubstituted heteroaromatic group, a substituted or unsubstituted carbocyclic group, or a substituted or unsubstituted heterocyclic group; or the first ring system is a substituted or unsubstituted heteroaromatic group, the second ring system is a substituted or unsubstituted aromatic group, a substituted or unsubstituted heteroaromatic group, a substituted or unsubstituted carbocyclic group, or a substituted or unsubstituted heterocyclic group; or the first ring system is a substituted or unsubstituted saturated carbocyclic group, the second ring system is a substituted or unsubstituted aromatic group, a substituted or unsubstituted unsaturated carbocyclic group, a substituted or unsubstituted heterocyclic group, or a substituted or unsubstituted ring B:

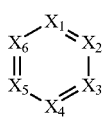

Ring B wherein X$_1$ to X$_6$ are each independently selected from carbon or a heteroatom; or the first ring system is a substituted or unsubstituted unsaturated carbocyclic group, the second ring system is a substituted or unsubstituted aromatic group, a substituted or unsubstituted carbocyclic group, a substituted or unsubstituted heterocyclic group, or a substituted or unsubstituted ring B:

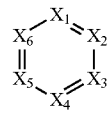

Ring B wherein X$_1$ to X$_6$ are each independently selected from carbon or a heteroatom; or the first ring system is a substituted or unsubstituted heterocyclic group, the second ring system is a substituted or unsubstituted heteroaromatic group, a substituted or unsubstituted carbocyclic group, or a substituted or unsubstituted heterocyclic group; and R$_3$ to R$_{11}$ are each independently selected from H, a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic;

R$_{12}$ is selected from H or a hydrocarbyl group;

Y is a heteroatom;

Ring is selected from a substituted or unsubstituted thiomorpholinyl group, a substituted or unsubstituted morpholinyl group, or a substituted or unsubstituted piperidinyl group, wherein the nitrogen in the Ring is bonded to A;

A is selected from a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic; and n is 0 or 1, when n is 1 and the Ring is selected from a substituted or unsubstituted morpholinyl group, or a substituted or unsubstituted piperidinyl group, A is selected from a substituted or unsubstituted hydrocarbon group, a substituted or unsubstituted carbocyclic group, a substituted or unsubstituted heterocyclic group, substituted or unsubstituted aromatic, or a substituted or unsubstituted heteroaromatic.

2. The compound according to claim 1, wherein the first ring system is a substituted or unsubstituted heterocyclic group, the second ring system is a substituted or unsubstituted heteroaromatic group, a substituted or unsubstituted carbocyclic group, or a substituted or unsubstituted heterocyclic group.

3. The compound according to claim 1, wherein the first ring system is a substituted or unsubstituted unsaturated carbocyclic group, the second ring system is a substituted or unsubstituted aromatic group, a substituted or unsubstituted carbocyclic group, a substituted or unsubstituted heterocyclic group; or a substituted or unsubstituted ring B:

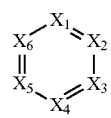

Ring B wherein X$_1$ to X$_6$ are each independently selected from carbon or a heteroatom.

4. The compound according to claim 1, wherein the first ring system is a substituted or unsubstituted carbocyclic group and the second ring system is a substituted or unsubstituted ring B:

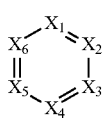

Ring B wherein $X_1$ to $X_6$ are each independently selected from carbon or a heteroatom.

5. The compound according to claim 3, wherein $X_1$ is N and $X_2$ to $X_6$ is carbon.

6. The compound according to claim 4, wherein $X_1$ is N and $X_2$ to $X_6$ is carbon.

7. The compound according to claim 5, wherein the ring B is fused to the first ring system at $X_2$ and $X_3$.

8. The compound according to claim 6, wherein the ring B is fused to the first ring system at $X_2$ and $X_3$.

9. The compound according to claim 1, wherein the first ring is a five-membered ring.

10. The compound according to claim 1, wherein the first ring is a six-membered ring.

11. The compound according to claim 1, wherein the substituted or unsubstituted polycyclic ring further comprises a third ring system fused to the first ring system.

12. The compound according to claim 11, wherein the third ring system is a substituted or unsubstituted aromatic group, a substituted or unsubstituted heteroaromatic group, a substituted or unsubstituted carbocyclic group, or a substituted or unsubstituted heterocyclic group.

13. The compound according to claim 12, wherein the third ring system is a substituted or unsubstituted heteroaromatic group or a substituted or unsubstituted heterocyclic group.

14. The compound according to claim 1, wherein n is 0.

15. The compound according to claim 1, wherein n is 1 and A is a substituted or unsubstituted heteroaromatic group.

16. The compound according to claim 15, wherein A is a pyridinyl group.

17. The compound according to claim 1, wherein Y is a nitrogen atom.

18. The compound according to claim 17, wherein $R_7$ is a substituted or unsubstituted alkyl group or a substituted or unsubstituted heteroaromatic group and $R_3$ to $R_6$ and $R_8$ to $R_{12}$ are each independently selected from H or a substituted or unsubstituted hydrocarbon group.

19. The compound according to claim 17, wherein $R_7$ is the substituted or unsubstituted alkyl group or a substituted or unsubstituted pyridyl group and $R_3$ to $R_6$ and $R_8$ to $R_{12}$ are each H.

20. The compound according to claim 1, wherein the compound penetrates the blood brain barrier of a mammal.

21. The compound according to claim 1, wherein at least about 50% of the compound is orally absorbed by a mammal.

22. The compound according to claim 1, wherein the compound has an $IC_{50}$ for a cancer cell population of less than about 1000 nM.

23. The compound according to claim 1 for treatment of a cancer.

24. The compound according to claim 23, wherein the cancer is selected from lung cancer, cervical cancer, ovarian cancer, cancer of CNS, skin cancer, prostate cancer, sarcoma, breast cancer, leukemia, colorectal cancer, head cancer, neck cancer or kidney cancer.

25. The compound according to claim 23, wherein the cancer is selected from small cell lung cancer, breast cancer, acute leukemia, chronic leukemia, colorectal cancer, or brain cancer.

26. The compound according to claim 23, wherein the cancer is a carcinoma.

27. The compound according to claim 26, wherein the carcinoma is selected from small cell carcinomas, cervical carcinomas, glioma, astrocytoma, prostate carcinomas, ovarian carcinomas, melanoma, breast carcinomas, or colorectal carcinomas.

28. The compound according to claim 26, wherein the carcinoma is small cell lung carcinoma.

29. A pharmaceutical composition comprising the compound according to claim 1 and at least one pharmaceutically acceptable carrier and/or diluent.

30. A pharmaceutical composition comprising an anti-cancer agent and the compound according to claim 1.

31. A method for treating a cancer in a mammal, comprising administering to the mammal a therapeutically effective amount of a compound of Formula I or IA:

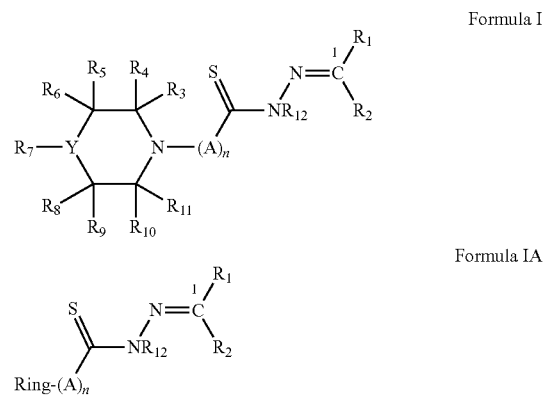

a pharmaceutically-acceptable salt, tautomer, optical isomer, and/or combination thereof;

wherein:

$R_1$ and $R_2$ together form a substituted or unsubstituted polycyclic ring comprising at least two ring systems, said at least two ring systems comprising a first ring system bonded to C1 and a second ring system fused to the first ring system, wherein:

the first ring system is a substituted or unsubstituted aromatic group, the second ring system is a substituted or unsubstituted aromatic group, a substituted or unsubstituted heteroaromatic group, a substituted or unsubstituted carbocyclic group, or a substituted or unsubstituted heterocyclic group; or the first ring system is a substituted or unsubstituted heteroaromatic group, the second ring system is a substituted or unsubstituted aromatic group, a substituted or unsubstituted heteroaromatic group, a substituted or unsubstituted carbocyclic group, or a substituted or unsubstituted heterocyclic group; or the first ring system is a substituted or unsubstituted saturated carbocyclic group, the second ring system is a substituted or unsubstituted aromatic group, a substituted or unsubstituted unsaturated carbocyclic group, a substituted or unsubstituted heterocyclic group, or a substituted or unsubstituted ring B:

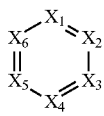

Ring B wherein $X_1$ to $X_6$ are each independently selected from carbon or a heteroatom; or the first ring system is a substituted or unsubstituted unsaturated carbocyclic group, the second ring system is a substituted or unsubstituted aromatic group, a substituted or unsubstituted carbocyclic group, a substituted or unsubstituted heterocyclic group, or a substituted or unsubstituted ring B:

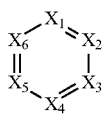

Ring B wherein $X_1$ to $X_6$ are each independently selected from carbon or a heteroatom; or the first ring system is a substituted or unsubstituted heterocyclic group, the second ring system is a substituted or unsubstituted heteroaromatic group, a substituted or unsubstituted carbocyclic group, or a substituted or unsubstituted heterocyclic group; and $R_3$ to $R_{11}$ are each independently selected from H, a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic;

$R_{12}$ is selected from H or a hydrocarbyl group;

Y is a heteroatom;

Ring is selected from a substituted or unsubstituted thiomorpholinyl group, a substituted or unsubstituted morpholinyl group, or a substituted or unsubstituted piperidinyl group, wherein the nitrogen in the Ring is bonded to A;

A is selected from a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic; and n is 0 or 1, when n is 1 and the Ring is selected from a substituted or unsubstituted morpholinyl group, or a substituted or unsubstituted piperidinyl group, A is selected from a substituted or unsubstituted hydrocarbon group, a substituted or unsubstituted carbocyclic group, a substituted or unsubstituted heterocyclic group, substituted or unsubstituted aromatic, or a substituted or unsubstituted heteroaromatic, wherein the cancer is selected from small cell lung cancer, non-small cell lung cancer, breast cancer, acute leukemia, chronic leukemia, colorectal cancer, or brain cancer.

32. The method according to claim 31, wherein the compound is co-administered with radiation therapy.

33. A method for treating a cancer in a mammal, comprising administering to the mammal a therapeutically effective amount of the composition according to claim 29, wherein the cancer is selected from small cell lung cancer, non-small cell lung cancer, breast cancer, acute leukemia, chronic leukemia, colorectal cancer, or brain cancer.

34. A method for treating a cancer in a mammal, comprising administering to the mammal a therapeutically effective amount of the composition according to claim 30, wherein the cancer is selected from small cell lung cancer, non-small cell lung cancer, breast cancer, acute leukemia, chronic leukemia, colorectal cancer, or brain cancer.

35. The method according to claim 33, wherein the composition is co-administered with radiation therapy.

36. The method according to claim 31, wherein the mammal is a human.

37. The method according to claim 31, wherein the compound inhibits development of a drug resistant form of the cancer.

38. The method according to claim 31, wherein the cancer is a carcinoma.

39. The method according to claim 38, wherein the carcinoma is selected from small cell lung carcinomas, breast carcinomas, or colorectal carcinomas.

40. The method according to claim 39, wherein the carcinoma is small cell lung carcinoma.

41. The method according to claim 31, wherein the compound is administered orally and/or parenterally.

42. A method for preparing the compound of claim 1, the method comprising:

a) reacting a compound of Formula II:

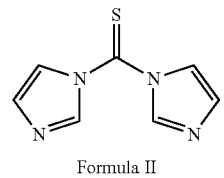

Formula II with:

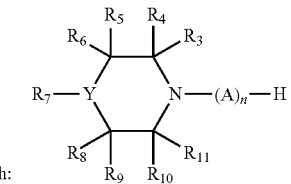

to form an intermediate of Formula III:

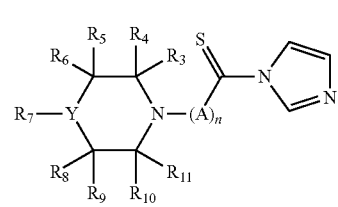

Formula III b) reacting the Intermediate of Formula III with $R_{12}NHNH_2$ to form an Intermediate of Formula IV:

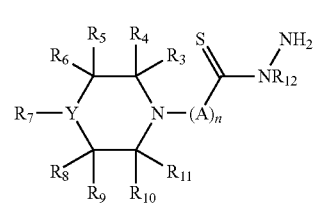

Formula IV c) reacting the Intermediate of Formula IV with a ketone:
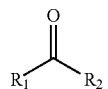
under condensation conditions, to form the compound of Formula I.
43. The method according to claim 42, wherein n is 0.
44. The method according to claim 31, wherein A is a substituted or unsubstituted heteroaromatic group.
* * * * *